US011667840B2

(12) United States Patent
Manabe et al.

(10) Patent No.: US 11,667,840 B2
(45) Date of Patent: *Jun. 6, 2023

(54) LIQUID-CRYSTALLINE MEDIUM

(71) Applicant: Merck Patent GmbH, Darmstadt (DE)

(72) Inventors: Atsutaka Manabe, Bensheim (DE); Christian Jasper, Seligenstadt (DE); Volker Reiffenrath, Rossdorf (DE); Constanze Brocke, Gross-Gerau (DE); Detlef Pauluth, Ober-Ramstadt (DE); Dagmar Klass, Darmstadt (DE); Michael Wittek, Erzhausen (DE); Renate Seeger, Riedstadt (DE); Dmitry Ushakov, Muenster (DE); Beate Schneider, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 118 days.

This patent is subject to a terminal disclaimer.

(21) Appl. No.: 16/344,463

(22) PCT Filed: Oct. 23, 2017

(86) PCT No.: PCT/EP2017/076933
§ 371 (c)(1),
(2) Date: Apr. 24, 2019

(87) PCT Pub. No.: WO2018/077765
PCT Pub. Date: May 3, 2018

(65) Prior Publication Data
US 2019/0330530 A1    Oct. 31, 2019

(30) Foreign Application Priority Data

Oct. 24, 2016 (EP) .................... 16195264

(51) Int. Cl.
*C09K 19/16* (2006.01)
*C07C 331/28* (2006.01)
*H01Q 21/00* (2006.01)
*C09K 19/32* (2006.01)
*C09K 19/18* (2006.01)
*C09K 19/30* (2006.01)
*H01Q 1/38* (2006.01)
*C09K 19/04* (2006.01)

(52) U.S. Cl.
CPC .......... *C09K 19/322* (2013.01); *C07C 331/28* (2013.01); *C09K 19/16* (2013.01); *C09K 19/18* (2013.01); *C09K 19/3003* (2013.01); *H01Q 1/38* (2013.01); *C09K 2019/0448* (2013.01); *C09K 2019/0459* (2013.01); *C09K 2019/161* (2013.01); *C09K 2019/163* (2013.01); *C09K 2019/181* (2013.01); *C09K 2019/3004* (2013.01); *H01Q 21/00* (2013.01)

(58) Field of Classification Search
CPC .................. C07C 331/28; C09K 19/16; C09K 2019/0459
See application file for complete search history.

(56) References Cited

U.S. PATENT DOCUMENTS

| 5,380,461 | A | * | 1/1995 | Sato .................... C07C 43/1747 |
| | | | | 252/299.61 |
| 8,129,002 | B2 | * | 3/2012 | Kirsch .................. C09K 19/02 |
| | | | | 428/1.1 |
| 8,283,001 | B2 | | 10/2012 | Kawamata et al. |
| 8,940,185 | B2 | * | 1/2015 | Tanaka ............... C09K 19/3458 |
| | | | | 252/299.6 |
| 9,593,279 | B2 | * | 3/2017 | Wittek ............... H01Q 21/0006 |
| 10,711,197 | B2 | * | 7/2020 | Wittek ................. C09K 19/12 |
| 11,254,874 | B2 | * | 2/2022 | Wittek ................ C09K 19/586 |
| 2008/0149891 | A1 | | 6/2008 | Klasen-Memmer et al. |
| 2012/0267571 | A1 | | 10/2012 | Jasper et al. |
| 2014/0217325 | A1 | * | 8/2014 | Manabe ............ C09K 19/2007 |
| | | | | 560/118 |
| 2016/0280996 | A1 | | 9/2016 | Okumura et al. |

FOREIGN PATENT DOCUMENTS

CN      104140825 A  *  11/2014
DE      102011117048 A1     5/2012
(Continued)

OTHER PUBLICATIONS

English translation of WO2012069133. (Year: 2012).*
English translation of JP2002012871. (Year: 2002).*
English translation of CN 104140825. (Year: 2014).*
International Search Report WO2017EP76933 dated Jan. 4, 2018 (pp. 1-2).
Notification of Reasons for Refusal in corresponding JP Pat. Appl. No 2019-521762 dispatched Nov. 17, 2021 (English translation—pp. 1-6).

*Primary Examiner* — Chanceity N Robinson
*Assistant Examiner* — Anna Malloy
(74) *Attorney, Agent, or Firm* — Millen White Zelano and Branigan, PC; Csaba Henter

(57) ABSTRACT

The present invention relates to liquid-crystalline media comprising one or more compounds of formula DFS

DFS

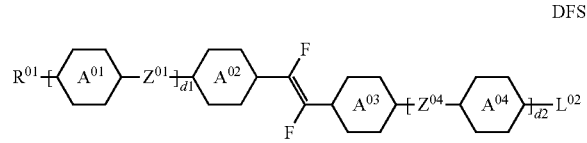

in which the groups and parameters occurring have the meanings indicated in claim 1, to high-frequency components comprising same, especially microwave components for high-frequency devices, such as devices for shifting the phase of microwaves, in particular for microwave phased-array antennas. The present invention further relates to novel mesogenic compounds.

8 Claims, No Drawings

(56) References Cited

FOREIGN PATENT DOCUMENTS

| | | | |
|---|---|---|---|
| EP | 2351727 B1 | 7/2014 | |
| EP | 2522649 B1 | 4/2016 | |
| JP | 2002012871 A * | 1/2002 | |
| JP | 2002357801 A | 12/2002 | |
| JP | 2008143902 A | 6/2008 | |
| JP | 2014040499 A | 3/2014 | |
| JP | 2017002160 A | 1/2017 | |
| WO | 12069133 A1 | 5/2012 | |
| WO | WO-2012069133 A1 * | 5/2012 | ............. C09K 19/42 |
| WO | 13139176 A1 | 9/2013 | |

* cited by examiner

LIQUID-CRYSTALLINE MEDIUM

The present invention relates to liquid-crystalline media and to high-frequency components comprising same, especially microwave components for high-frequency devices, such as devices for shifting the phase of microwaves, in particular for microwave phased-array antennas. In addition, the present invention relates to novel mesogenic compounds.

Liquid-crystalline media have long been utilised in electro-optical displays (liquid crystal displays-LCDs) in order to display information.

Difluorostilbenes useful for liquid crystal electro-optical devices are described for example in U.S. Pat. No. 5,380,461 and EP 2522649 A1.

Liquid-crystalline media have recently also been proposed for use in components for microwave technology, as described, for example, in DE 10 2004 029 429 A.

In WO 2012/069133 A1, alkynyl derivatives of difluorostilbene as for example of the following formula

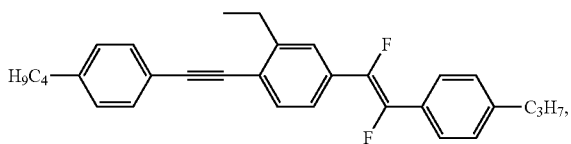

are disclosed as component in liquid crystal mixtures for microwave applications.

Phenylethynyltolane derivatives, also known as bistolanes, having an additional alkyl substituent on the central phenylene ring are known to the person skilled in the art.

For example, Wu, S.-T., Hsu, C.-S. and Shyu, K.-F., Appl. Phys. Lett., 74 (3), (1999), pages 344-346, discloses various liquid-crystalline bistolane compounds containing a lateral methyl group, of the formula

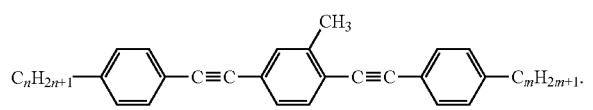

Besides liquid-crystalline bistolane compounds of this type containing a lateral methyl group, Hsu, C. S., Shyu, K. F., Chuang, Y. Y. and Wu, S.-T., Liq. Cryst., 27 (2), (2000), pages 283-287, also discloses corresponding compounds containing a lateral ethyl group and proposes the use thereof, inter alia, in liquid crystal optically phased arrays.

Dabrowski, R., Kula, P., Gauza, S., Dziadiszek, J., Urban, S. and Wu, S.-T., IDRC 08, (2008), pages 35-38, mentions dielectrically neutral bistolane compounds with and without a lateral methyl group on the central ring besides the strongly dielectrically positive isothiocyanatobistolan compounds of the formula

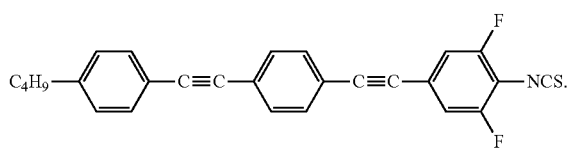

An industrially valuable application of liquid-crystalline media in high-frequency technology is based on their property that their dielectric properties can be controlled, particularly for the gigahertz region and the terahertz region, by a variable voltage. This enables the construction of tunable antennas which contain no moving parts (Gaebler, A., Moessinger, A., Goelden, F., et al., "Liquid Crystal-Reconfigurable Antenna Concepts for Space Applications at Microwave and Millimeter Waves", International Journal of Antennas and Propagation, Volume 2009, Article ID 876989, (2009), pages 1-7, DOI: 10.1155/2009/876989).

Penirschke, A., Müller, S., Scheele, P., Weil, C., Wittek, M., Hock, C. and Jakoby, R.: "Cavity Perturbation Method for Characterisation of Liquid Crystals up to 35 GHz", 34th European Microwave Conference—Amsterdam, pp. 545-548, describe, inter alia, the properties of the known single liquid-crystalline substance K15 (also called 4-n-pentyl-4'-cyanobiphenyl or PP-5-N, Merck KGaA, Germany) at a frequency of 9 GHz.

For use in high-frequency technology, liquid-crystalline media having particular, hitherto rather unusual, unconventional properties, or combinations of properties, are required.

The already mentioned DE 10 2004 029 429 A describes the use of liquid-crystal media in microwave technology, inter alia in phase shifters. DE 10 2004 029 429 A has already investigated liquid-crystalline media with respect to their properties in the corresponding frequency range. In addition, it mentions liquid-crystalline media which comprise compounds of the formulae

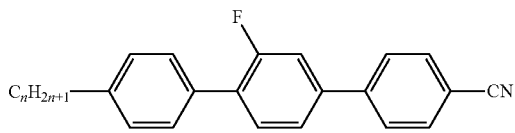

besides compounds of the formulae

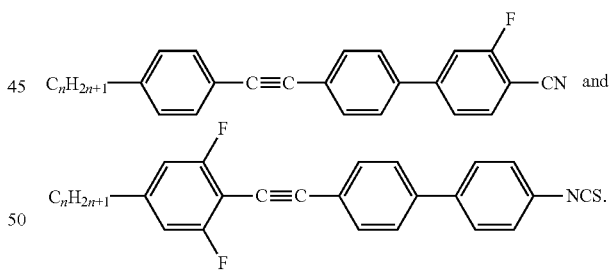

However, the compositions known to date are afflicted with several more or less serious disadvantages. Besides other deficiencies, most of them result in disadvantageously high losses and/or inadequate phase shift or inadequate material quality ($\eta$).

Novel liquid-crystalline media having improved properties are thus necessary. In particular, the loss in the microwave region and/or millimetre wave region must be reduced and the material quality improved.

In addition, there is a demand for an improvement in the low-temperature behaviour of the liquid-crystalline media and thus, also of the components. Both an improvement in the operating properties and also in the shelf life are necessary here.

Thus, there is a considerable demand for liquid-crystalline media having suitable properties for corresponding practical applications.

Surprisingly, it has now been found that it is possible to achieve liquid-crystal media for the use in components for high-frequency technology which do not have the disadvantages of the prior-art materials, or at least only do so to a considerably reduced extent, if compounds of formula DFS are employed.

Object of the present invention is a liquid crystal mixture comprising one or compounds of formula DFS

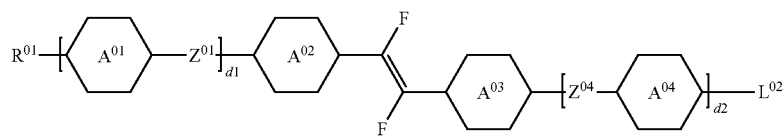

DFS wherein $L^{02}$ denotes $R^{02}$ or $X^{02}$, $R^{01}$ and $R^{02}$ denote alkyl, which is straight chain or branched having 1 to 20 C-atoms, is unsubstituted, mono- or poly-substituted by F, Cl or CN, and in which one or more $CH_2$ groups are optionally replaced, in each case independently from one another, by —O—, —S—, —$SiR^aR^b$—, —CO—, —COO—, —OCO—, —OCO—O—, —S—CO—, —CO—S—, —$CY^{01}$=$CY^{02}$— or —C≡C— in such a way that O and/or S atoms are not linked directly to one another, $Y^{01}$ and $Y^{02}$ identically or differently, denote H, F Cl, or CN, alternatively one of $Y^{01}$ and $Y^{02}$ may also denote H, $R^a$ and $R^b$ identically or differently, denote alkyl having 1 to 6 C atoms, $X^{02}$ denotes H, F, Cl, —CN, —NCS, —$SF_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably F, Cl, $CF_3$, $OCF_3$, or —NCS, $Z^{01}$ and $Z^{04}$ on each occurrence, identically or differently, denote —C≡C—, —CF=CF—, —$CF_2$O—, —$OCF_2$—, —$CH_2$O—, —$OCH_2$—, —$CH_2CH_2$—, —$CF_2CF_2$—, —$CH_2CF_2$—, —$CF_2CH_2$—, or a single bond,

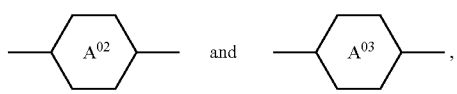

independently of one another, denote

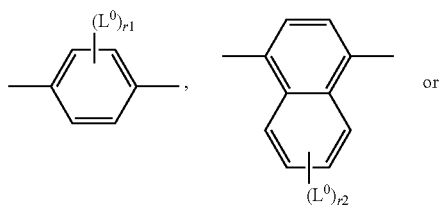

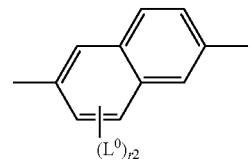

wherein, one or more of CH groups, preferably one CH group or two CH groups, preferably non-adjacent, particularly preferably one CH group, may be replaced by N, and,

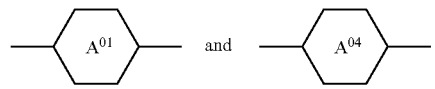

on each occurrence, independently of one another, are defined as $A^{02}$ and $A^{03}$, or alternatively denote

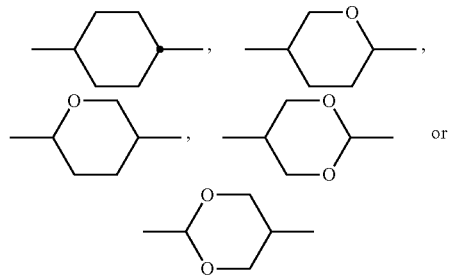

$L^0$ denotes halogen, alkyl, alkenyl or alkoxy having up to 6 C atoms, cycloalkyl or cycloalkenyl having 3 to 6 C atoms, where one or more H atoms can be substituted by fluorine, preferably alkyl having 1 to 3 C atoms, F or Cl, r1 is an integer from 0 to 4, r2 is an integer from 0 to 6, d1 and d2 are, independently from one another, 0, 1 or 2, and preferably (d1+d2) is 0, 1 or 2.

The compounds of formula DFS allow to realize media with an acceptably high clearing point and/or a comparatively high stability of the voltage holding ratio against temperature and/or UV-load and in particular against the latter. The media according to the invention show high "low temperature stability" which means that no crystallisation occurs upon cooling to −20° C., preferably to −30° C., more preferably to −40° C.

The media furthermore show high tunability, low dielectric loss and high figures-of-merit in devices for microwave applications, e.g. antennae.

The compounds of formula DFS are preferably selected from the compounds of formulae DFS-1 and DFS-2.

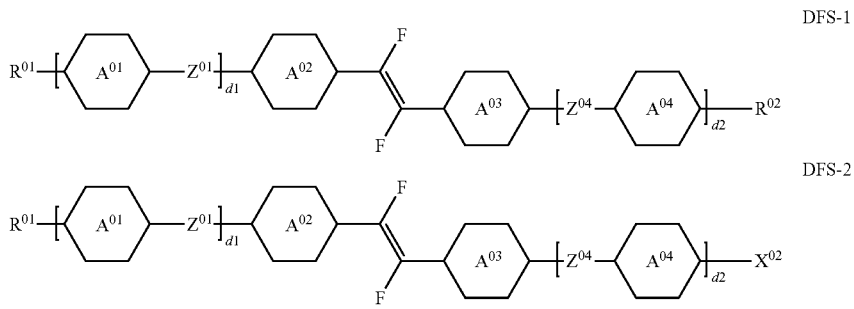

wherein the occurring groups and parameters have the meaning indicated above and preferably

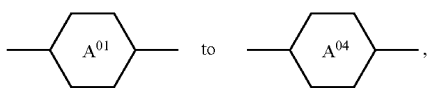

independently of one another, denote

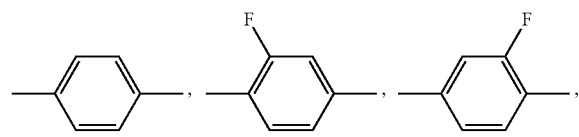

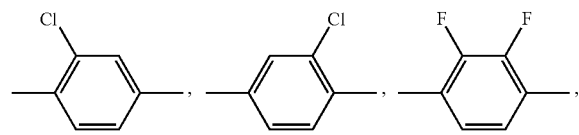

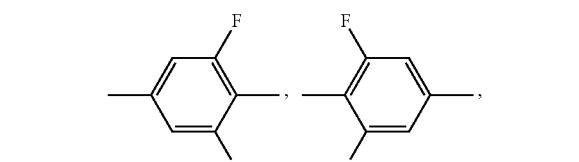

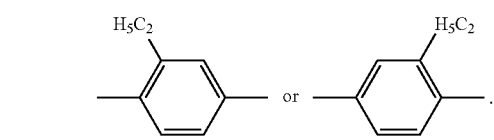

Preferred compounds of formula DFS-1 are selected from the following subformulae:

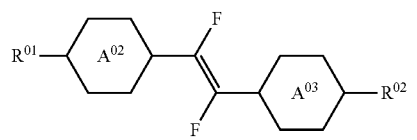

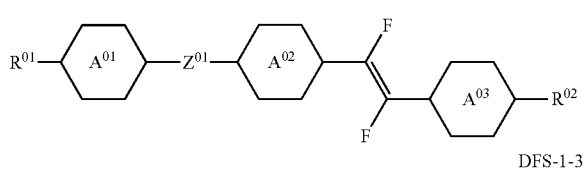

-continued

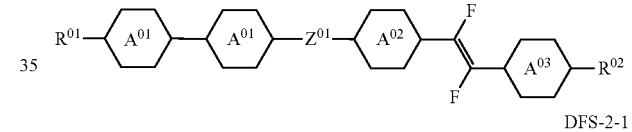

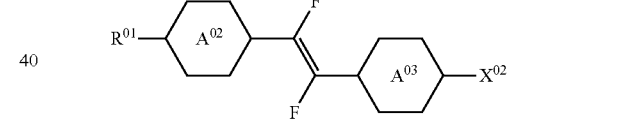

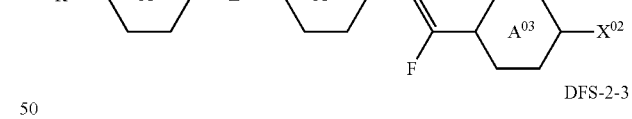

wherein $A^{01}$, $A^{02}$, $A^{03}$, $R^{01}$, $R^{02}$, $X^{02}$, $Z^{01}$, and $Z^{04}$ independently of one another, have the meanings indicated above, and preferably $Z^{01}$ and $Z^{04}$ denotes —C≡C—, trans-—CF=CF—, —CF$_2$O— or a single bond, $R^{01}$ and $R^{02}$ identically or differently, denote unfluorinated alkyl having 1 to 7 C atoms or unfluorinated alkenyl having 2 to 7 C atoms, or unfluorinated alkoxy having 1 to 7 C atoms, $X^{02}$ denotes F, CF$_3$, —OCF$_3$, or —NCS, particularly preferably —NCS.

The compounds of formula DFS-1-1 are preferably selected from the following sub-formulae
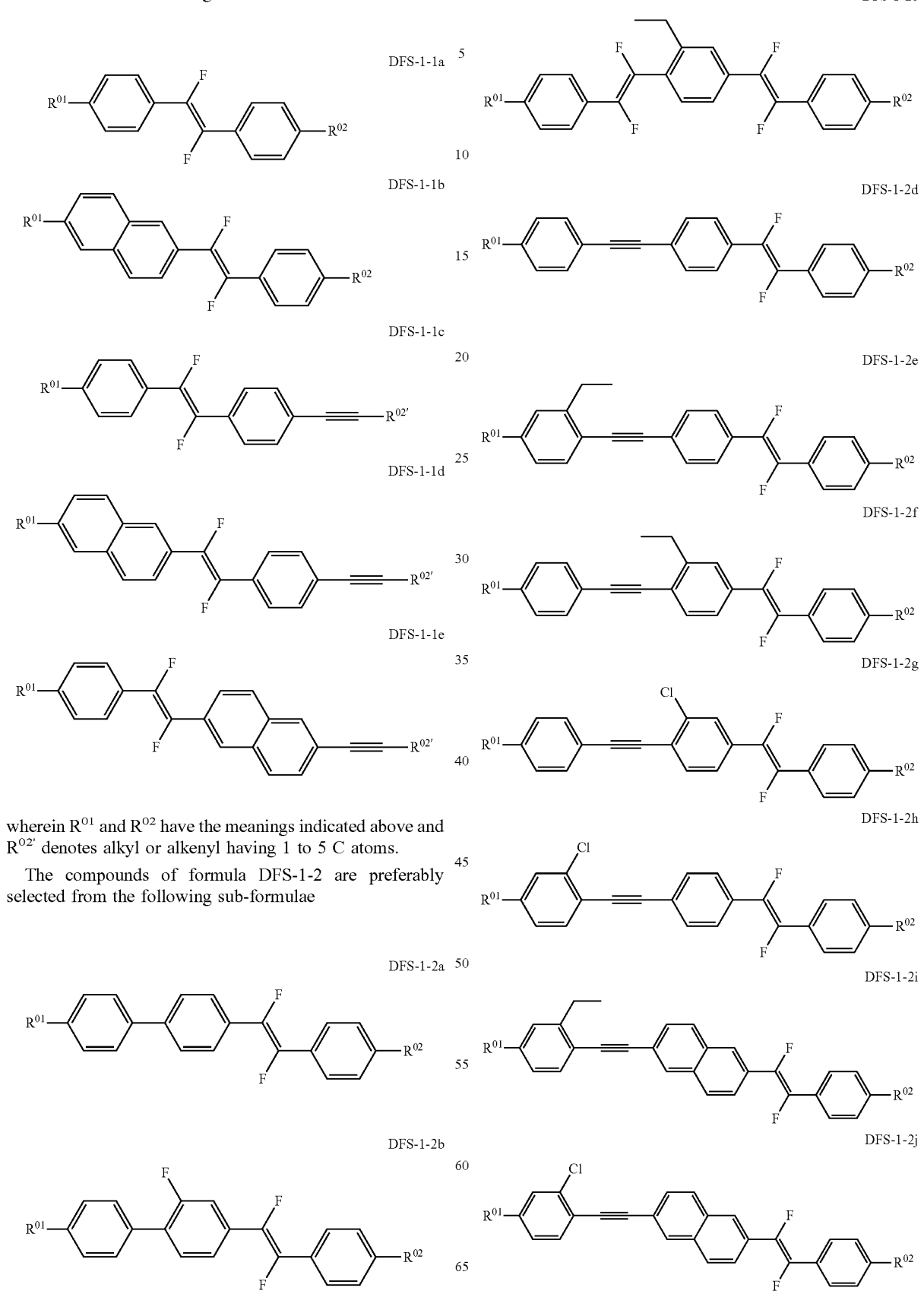
wherein $R^{01}$ and $R^{02}$ have the meanings indicated above and $R^{02\prime}$ denotes alkyl or alkenyl having 1 to 5 C atoms.
The compounds of formula DFS-1-2 are preferably selected from the following sub-formulae -continued

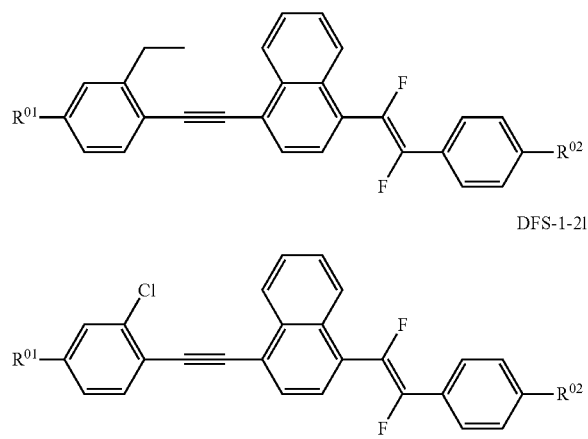

wherein R$^{01}$ and R$^{02}$ have the meanings indicated above.

The compounds of formula DFS-2-1 are preferably selected from the following sub-formulae

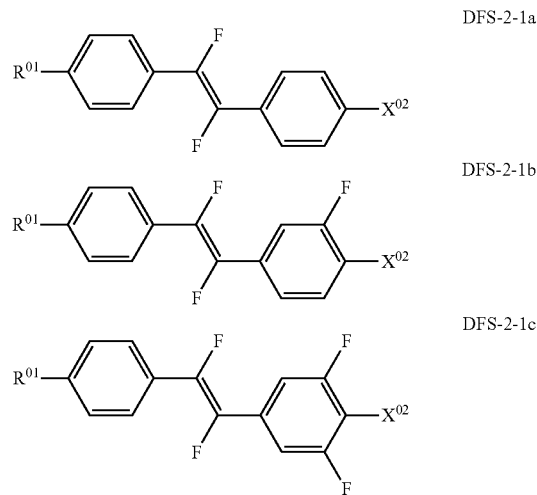

wherein R$^{01}$ and X$^{02}$ have the meanings indicated above.

Very particularly preferred sub-formulae of formula DFS-2-1 are the following sub-formulae

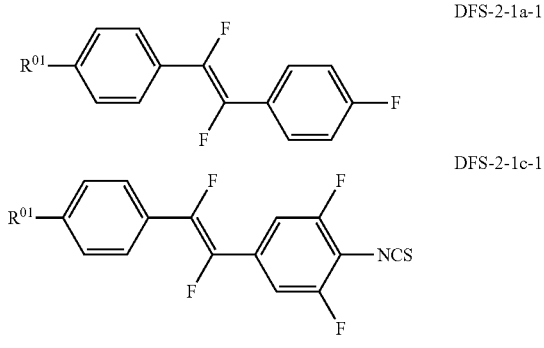

The compounds of formula DFS-3-2 are preferably selected from the following sub-formulae wherein R$^{01}$ and X$^{02}$ have the meaning indicated above, L$^{01}$ and L$^{02}$, identically or differently, denote H or F, and L$^{03}$ and L$^{04}$, identically or differently, denote alkyl having 1 to 6 C atoms, H, F or Cl.

Particularly preferred compounds of formulae DFS-2-2a to DFS-2-2c are selected from the following sub-formulae:

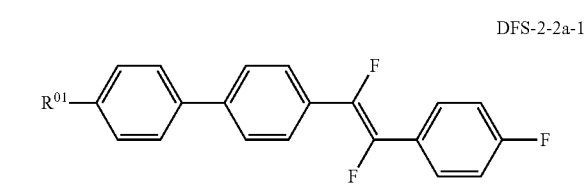

DFS-2-2a-2
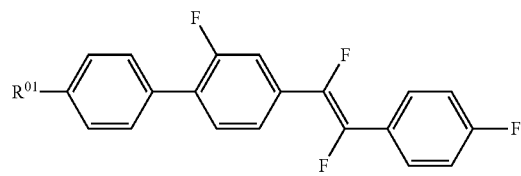
DFS-2-2a-3
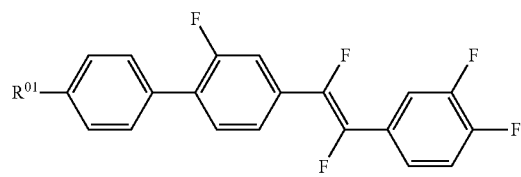
DFS-2-2a-4
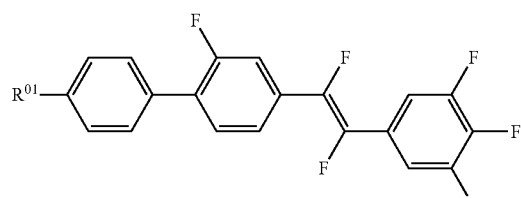
DFS-2-2a-5
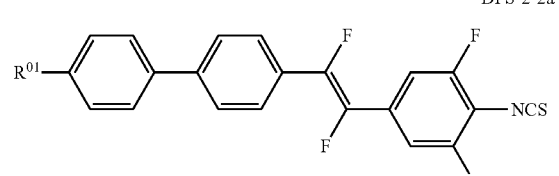
DFS-2-2a-6
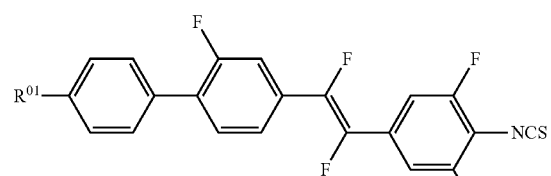
DFS-2-2a-7
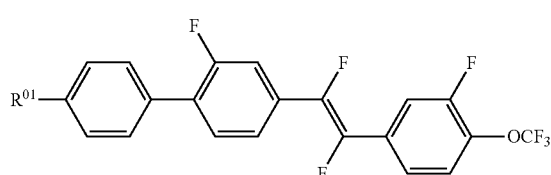
DFS-2-2b-1
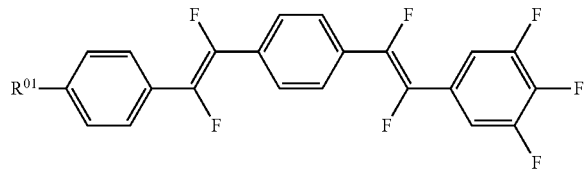
DFS-2-2b-2
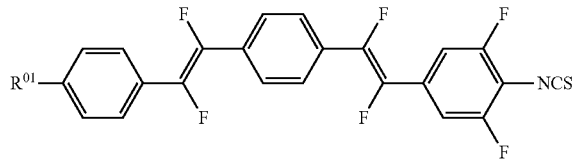
DFS-2-2c-1
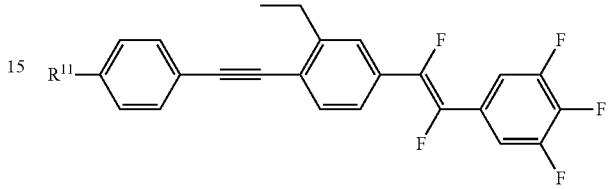
DFS-2-2c-2
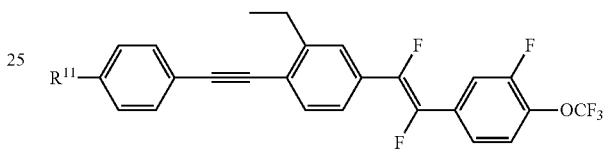
DFS-2-2c-3
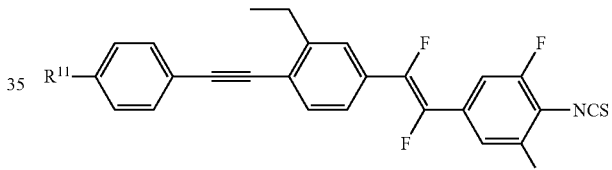
DFS-2-2c-4
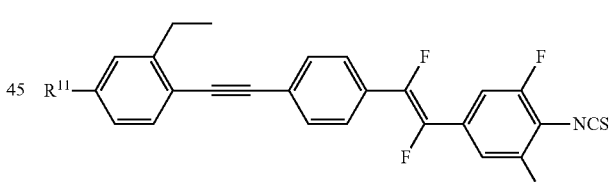
DFS-2-2c-5
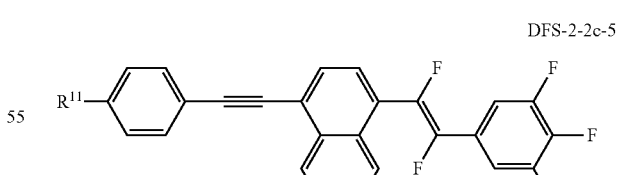
DFS-2-2c-6
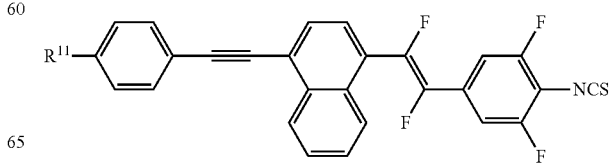

Preferred compounds of formula DFS-2-3 are selected from the following sub-formulae:

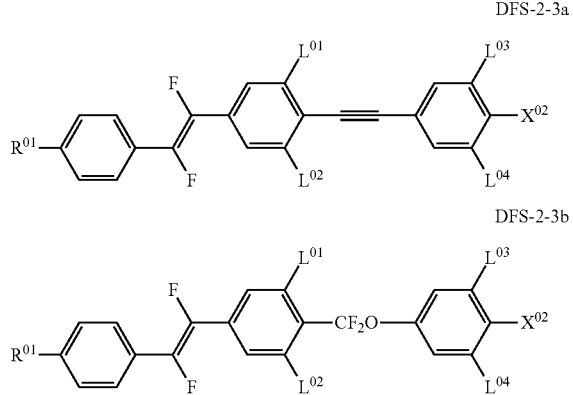

wherein the groups occurring have the meanings given above.

Preferred compounds of the formulae DFS-2-3a and DFS-2-3b are selected from the following sub-formulae:

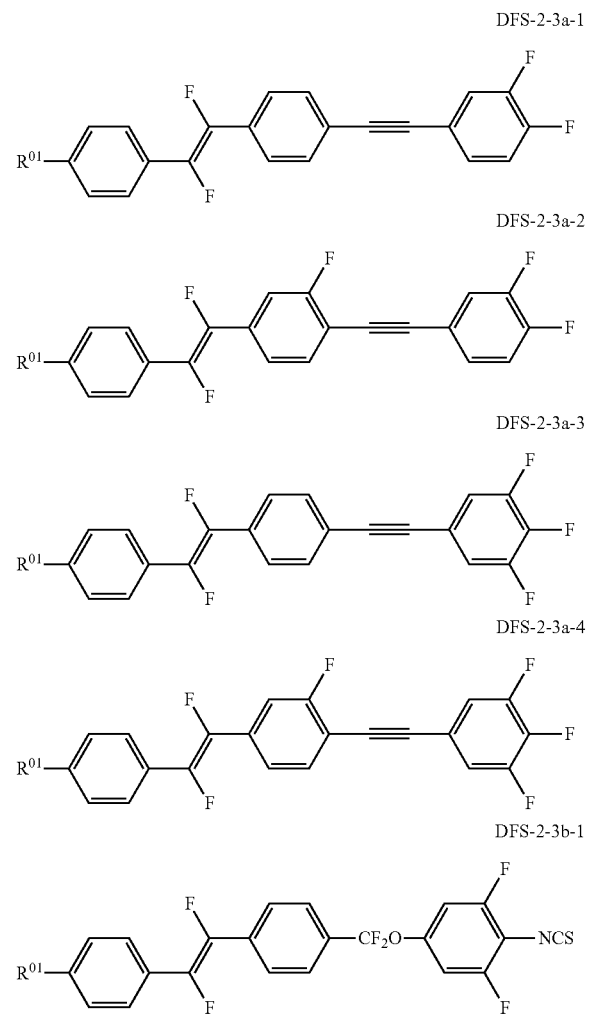

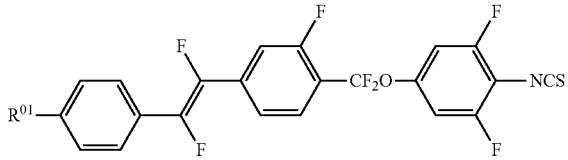

In a preferred embodiment of the present invention the group $R^{O1}$ or $R^{O2}$ in formula DFS-1 denotes —C≡C—$R^{O1*}$ wherein $R^{O1*}$ denotes alkyl having 1 to 5 C atoms.

In a preferred embodiment, the liquid crystalline medium comprises one or more compounds of formula T

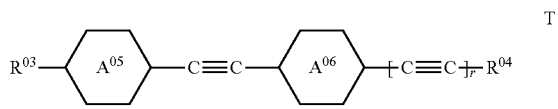

wherein $R^{O3}$ and $R^{O4}$ independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl, and in case r is 0, $R^{O4}$ may also denote F, Cl, CN, SCN, $CF_3$, $SF_5$, preferably F;

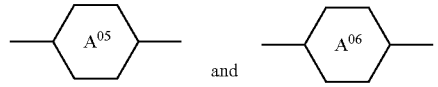

independently of one another, denote

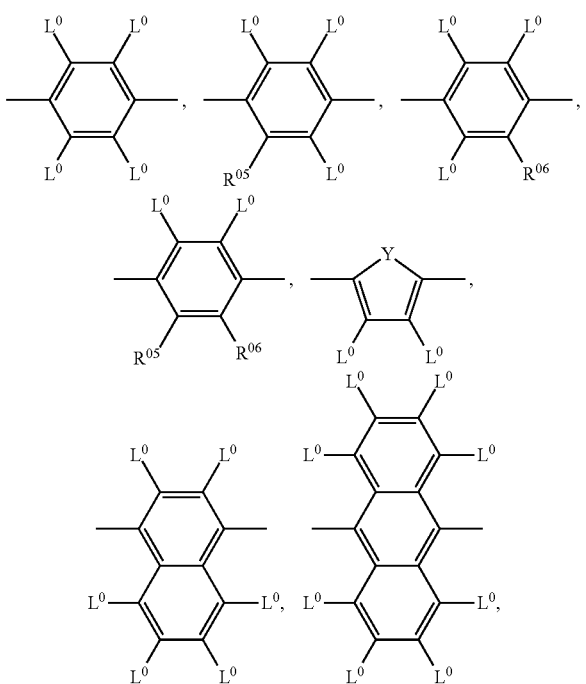

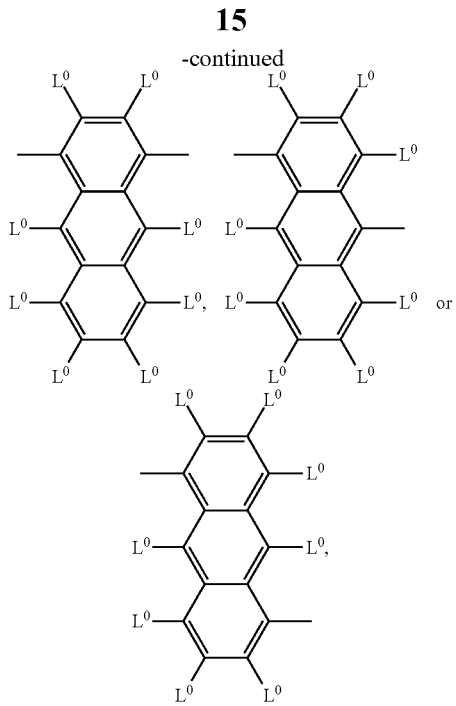

wherein Y denotes S or O,
and wherein in the 1,4-phenylene groups, one or more C—H groups may be replaced by N, and
$L^0$ on each occurrence, independently of one another, denotes H, Br, Cl, F, —CN, —NCS, —SCN, $SF_5$, $C_1$-$C_{10}$ alkyl, $C_1$-$C_{10}$ alkoxy, $C_3$-$C_6$ cycloalkyl or a mono- or polyfluorinated $C_1$-$C_{10}$ alkyl or alkoxy group,
$R^{05}$ and $R^{06}$ each, independently of one another, denote a halogenated or unsubstituted alkyl or alkoxy radical having 1 to 6 C atoms,
r is 0 or 1.

The compounds of formula T are preferably selected from compounds of the formulae T-1 to T-10:

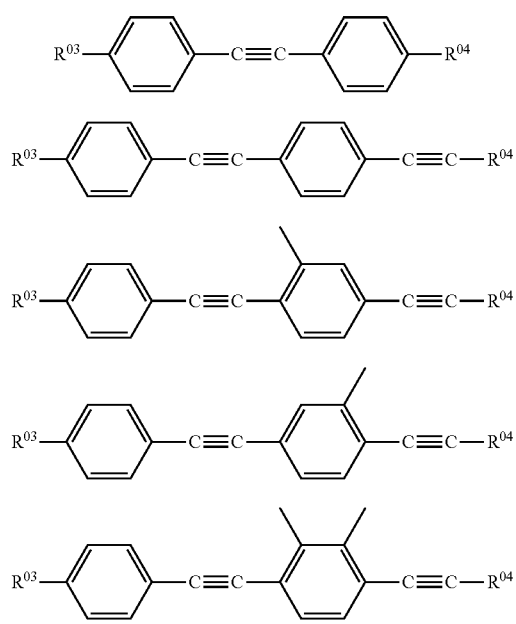

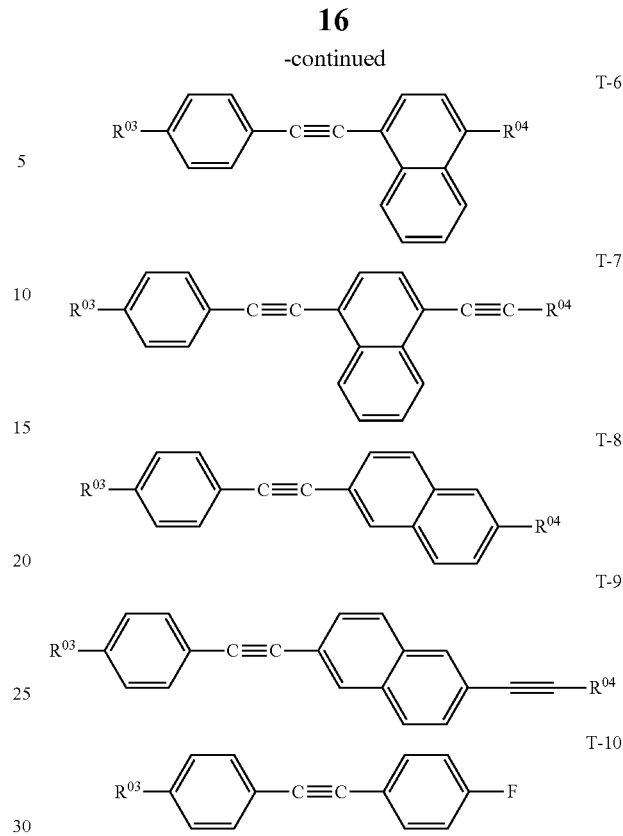

wherein $R^{03}$ and $R^{04}$ have the meaning indicated above and preferably, independently of one another other, denote alkyl or alkenyl having 2 to 7 C atoms.

In a preferred embodiment, the liquid crystalline medium comprises one or more compounds of formula U

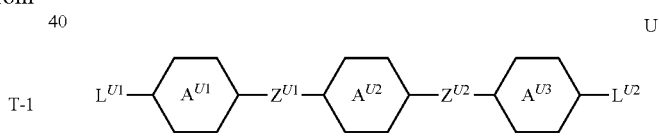

wherein
$L^{U1}$ denotes $R^{U1}$ and, in the case where $Z^{U1}$ and/or $Z^{U2}$ denote trans-CH=CH— or trans-CF=CF—, alternatively also denotes $X^{U1}$,
$R^{U2}$ denotes $R^{U2}$ and, in the case where $Z^{U1}$ and/or $Z^{U2}$ denote trans-CH=CH— or trans-CF=CF—, alternatively also denotes $X^{U2}$,
$R^{U1}$ and $R^{U2}$, independently of one another, denote H, unfluorinated alkyl or unfluorinated alkoxy having 1 to 17 C atoms or unfluorinated alkenyl, unfluorinated alkenyloxy or unfluorinated alkoxyalkyl having 2 to 15 C atoms,
$X^{U1}$ and $X^{U2}$, independently of one another, denote F or Cl, —CN, —NCS, —$SF_5$, fluorinated alkyl or alkoxy having 1 to 7 C atoms or fluorinated alkenyl, alkenyloxy or alkoxyalkyl having 2 to 7 C atoms,
one of
$Z^{U1}$ and $Z^{U2}$ denotes trans-CH=CH—, trans-CF=CF— or —C≡C— and the other denotes trans-CH=CH—, trans-CF=CF— or a single bond, preferably a single bond, and

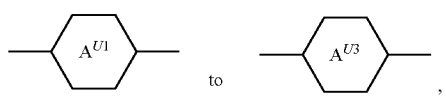

independently of one another, denote

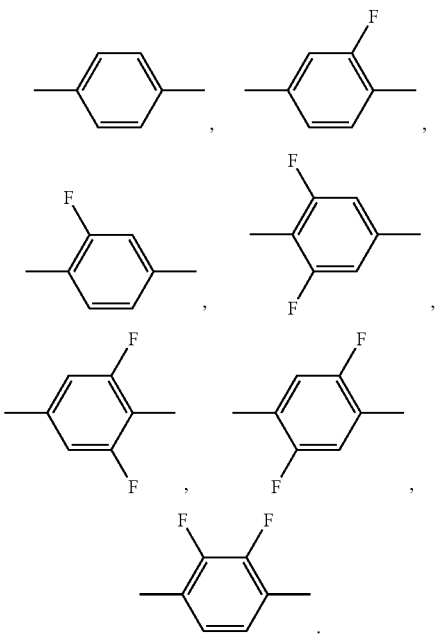

The compounds of the formula U are preferably selected from the group of the compounds of the formulae U-1 to U-3:

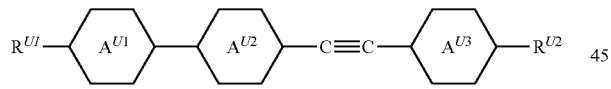   U-1

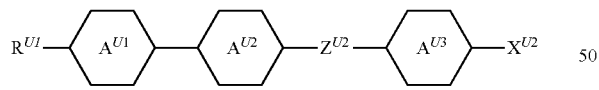   U-2

   U-3 in which $Z^{U1}$ and $Z^{U2}$ denote trans-CH=CH—, trans-CF=CF—, or —C≡C—, preferably trans-CH=CH— or —C≡C—, and the other parameters have the meaning given above under formula U and preferably $R^{U1}$ and $R^{U2}$, independently of one another, denote H, unfluorinated alkyl or alkoxy having 1 to 7 C atoms or unfluorinated alkenyl having 2 to 7 C atoms, $X^{U2}$ denotes F, Cl, —CN or —NCS, preferably —NCS, and one of

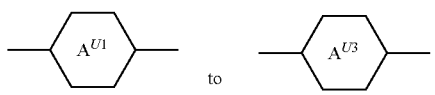

denotes

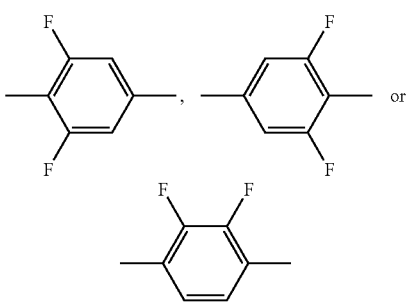

and the others, independently of one another, denote

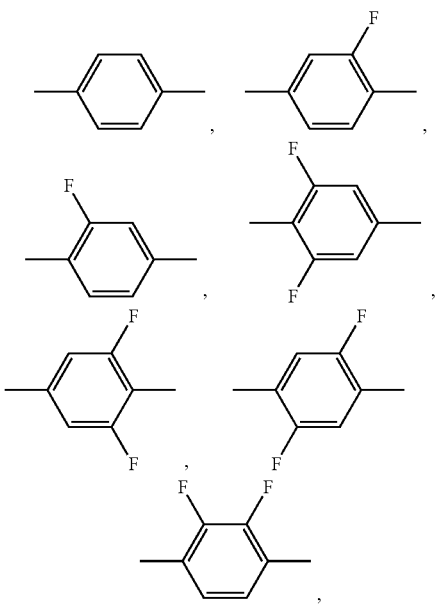

preferably

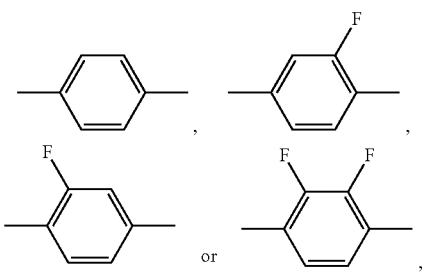

and preferably $R^{U1}$ denotes $C_nH_{2n+1}$ or $CH_2=CH-(CH_2)_Z$, and
$R^{U2}$ denotes $C_mH_{2m+1}$ or $O-C_mH_{2m+1}$ or $(CH_2)_Z-CH=CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The compounds of the formula U-1 are preferably selected from the group of the compounds of the formulae U-1a and U-1b, more preferably selected from compounds of the formula U-1a:

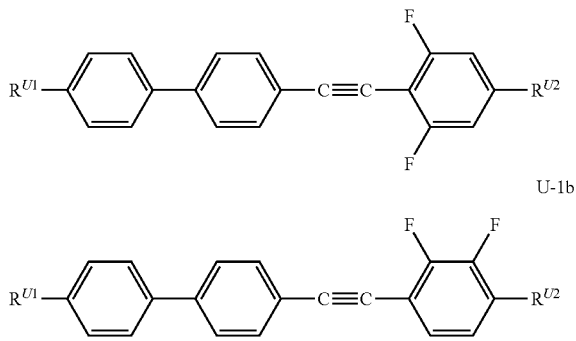

U-1a

U-1b in which $R^{U1}$ has the meaning indicated above and preferably denotes $C_nH_{2n+1}$ or $CH_2=CH-(CH_2)_Z$, and $R^{U2}$ has the meaning indicated above and preferably denotes $C_mH_{2m+1}$ or $O-C_mH_{2m+1}$ or $(CH_2)_Z-CH=CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{U1}$ and $R^{U2}$) here are, in particular, ($C_nH_{2n+1}$ and $C_mH_{2m+1}$) and ($C_nH_{2n+1}$ and $O-C_mH_{2m+1}$), in the case of formula U-1a particularly preferably ($C_nH_{2n+1}$ and $C_mH_{2m+1}$) and in the case of formula U-1b particularly preferably ($C_nH_{2n+1}$ and $O-C_mH_{2m+1}$).

The compounds of the formula U-2 are preferably selected from the compounds of the formula U-2a to U-2c:

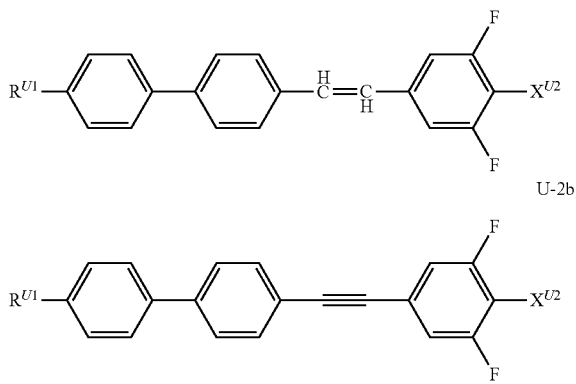

U-2a

U-2b

U-2c

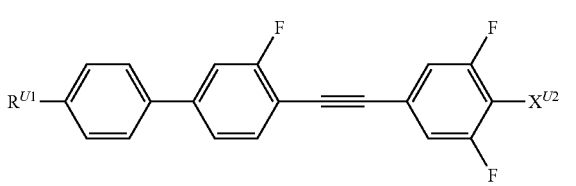

U-2d

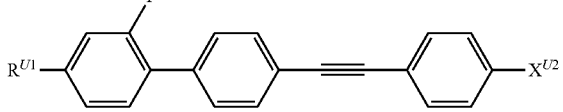

in which the parameters have the meaning given above under formula U-2 and preferably $R^{U1}$ has the meaning indicated above and preferably denotes $C_nH_{2n+1}$, in which n denotes an integer in the range from 0 to 7, preferably in the range from 1 to 5, and $X^{U2}$ denotes —F, —Cl, —OCF$_3$, —CN or —NCS, particularly preferably —NCS.

The compounds of the formula U-3 are preferably selected from compounds of the formulae U-3a to U-3c:

U-3a

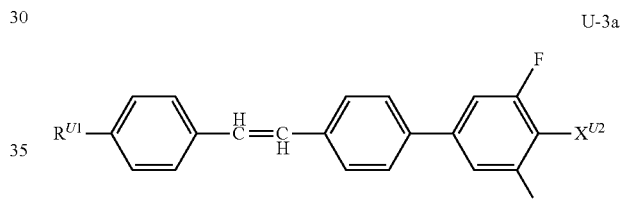

U-3b

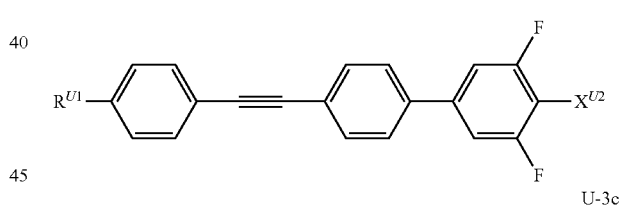

U-3c

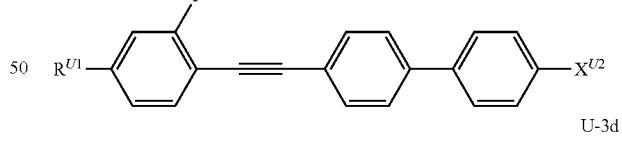

U-3d

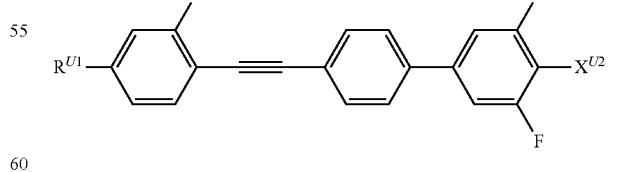

in which the parameters have the meaning given above under formula U-3 and preferably $R^{U1}$ has the meaning indicated above and preferably denotes $C_nH_{2n+1}$, in which n denotes an integer in the range from 0 to 7, preferably in the range from 1 to 5, and $X^{U2}$ denotes F, Cl, OCF$_3$, —CN or —NCS, particularly preferably —NCS.

In a preferred embodiment, the liquid crystalline medium comprises one or more compounds of formula I

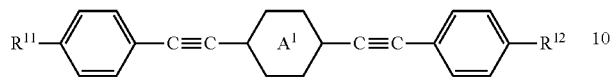

I wherein $R^{11}$ and $R^{12}$, independently of one another, denote unfluorinated alkyl or unfluorinated alkoxy, each having 1 to 15 C atoms, unfluorinated alkenyl, unfluorinated alkenyloxy or unfluorinated alkoxyalkyl, each having 2 to 15 C atoms, or cycloalkyl, alkylcycloalkyl, cycloalkenyl, alkylcycloalkenyl, alkylcycloalkylalkyl or alkylcycloalkenylalkyl, each having up to 15 C atoms;

denotes

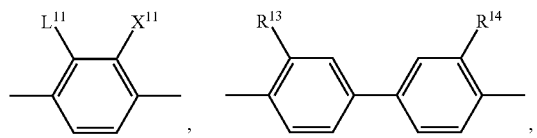

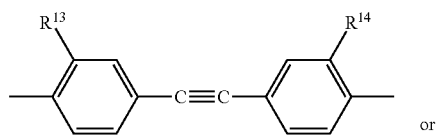

or

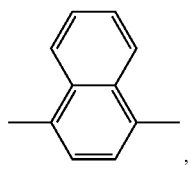

$L^{11}$ denotes H, alkyl having 1 to 6 C atoms, cycloalkyl having 3 to 6 C atoms or cycloalkenyl having 4 to 6 C atoms, $X^{11}$ denotes H, alkyl having 1 to 3 C atoms or halogen, $R^{13}$ and $R^{14}$, independently of one another, have the meaning given for $R^{11}$ and $R^{12}$, and alternatively one of $R^{13}$ and $R^{14}$ or both also denote H.

In the compounds of the formula I, the group

preferably denotes

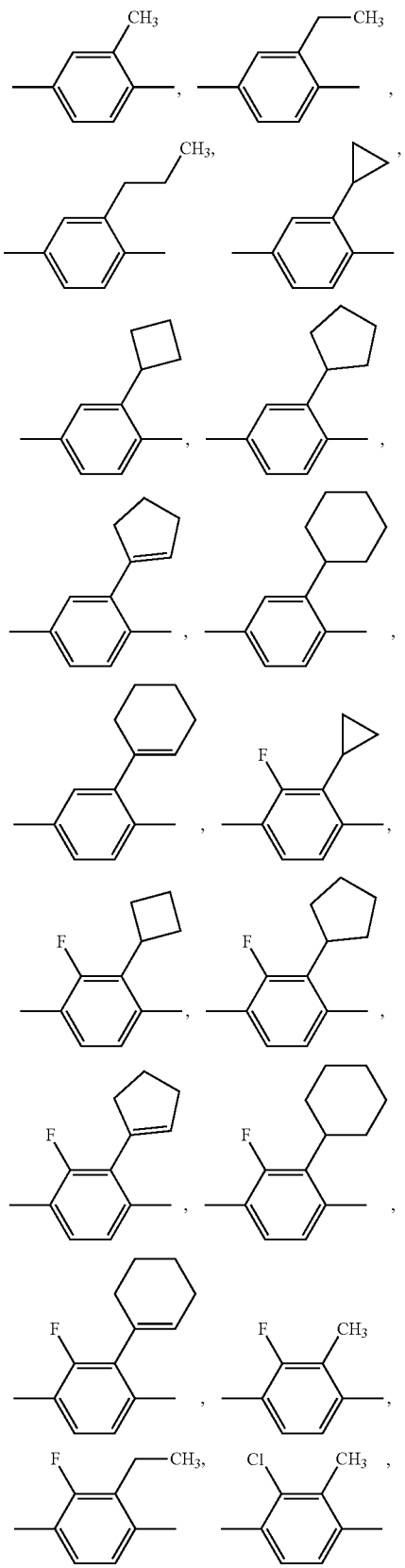

-continued

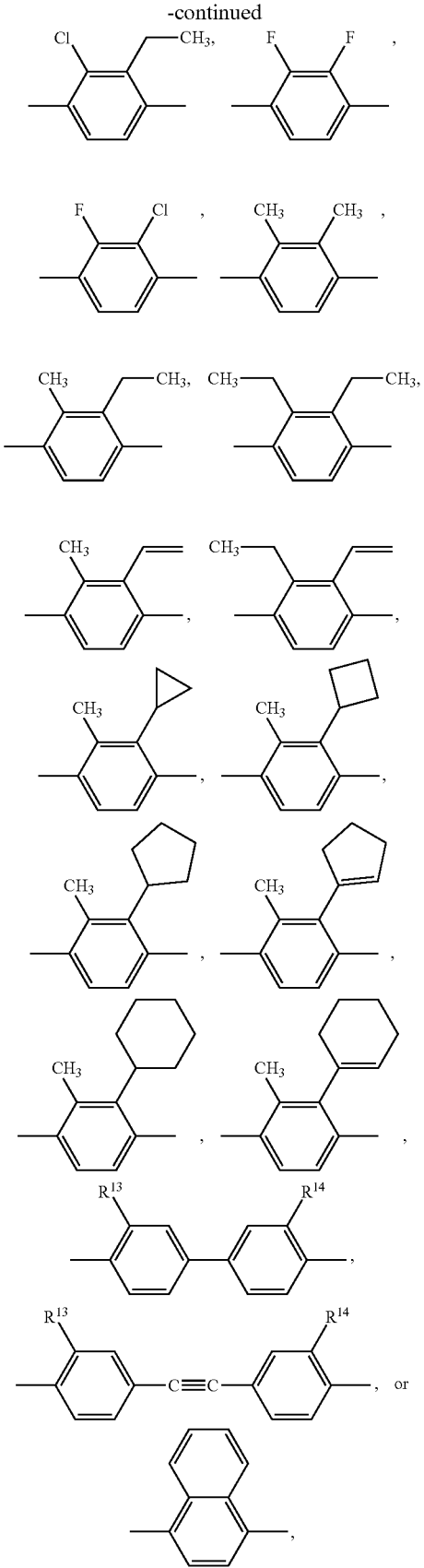

particularly preferably

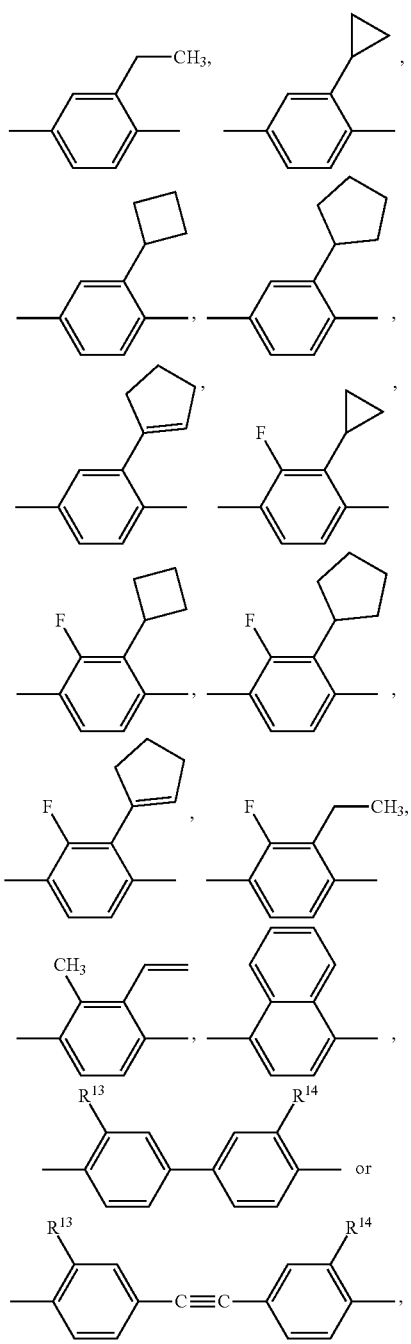

wherein $R^{13}$ and $R^{14}$ have the meaning given above and preferably $R^{13}$ and $R^{14}$ denote H, unfluorinated alkyl having 1 to 5 C atoms, unfluorinated cycloalkyl or cycloalkenyl having 3 to 7 C atoms, unfluorinated alkylcyclohexyl or unfluorinated cyclohexylalkyl, each having 4 to 12 C atoms, or unfluorinated alkylcyclohexylalkyl having 5 to 15 C atoms, particularly preferably cyclopropyl, cyclobutyl or cyclohexyl, and very particularly preferably at least one of $R^{13}$ and $R^{14}$ denotes n-alkyl, particularly preferably methyl, ethyl or n-propyl, and the other denotes H or n-alkyl, particularly preferably H, methyl, ethyl or n-propyl.

Furthermore, in formula I, $L^{11}$ preferably denotes $CH_3$, $C_2H_5$, n-$C_3H_7$ (—$(CH_2)_2CH_3$), i-$C_3H_7$ (—$CH(CH_3)_2$), cyclopropyl, cyclobutyl, cyclohexyl, cyclopent-1-enyl or cyclohex-1-enyl, and particularly preferably $CH_3$, $C_2H_5$, cyclopropyl or cyclobutyl, $X^{11}$ preferably denotes H, F or Cl, and particularly preferably H or F and very particularly preferably F, $R^{11}$ and $R^{12}$, independently of one another, denote unfluorinated alkyl or unfluorinated alkoxy, each having 1 to 7 C atoms, or unfluorinated alkenyl, unfluorinated alkenyloxy or unfluorinated alkoxyalkyl, each having 2 to 7 C atoms, particularly preferably $R^{11}$ denotes unfluorinated alkyl having 1 to 7 C atoms or unfluorinated alkenyl, unfluorinated alkenyloxy or unfluorinated alkoxyalkyl, each having 2 to 7 C atoms, and particularly preferably $R^{12}$ denotes unfluorinated alkyl or unfluorinated alkoxy, each having 1 to 7 C atoms, and In a preferred embodiment of the present invention, the compounds of the formula I are selected from the group of the compounds of the formulae I-1 to I-4, preferably of the formulae I-1 and/or I-2 and/or I-3 and/or I-4, preferably of the formulae I-1 and I-2:

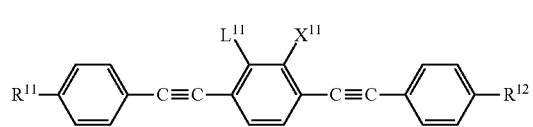

I-1

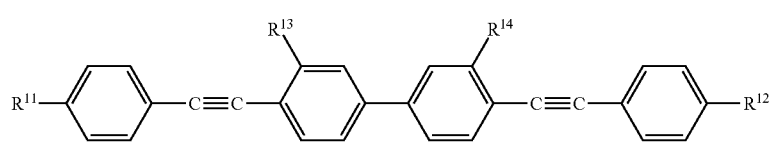

I-3

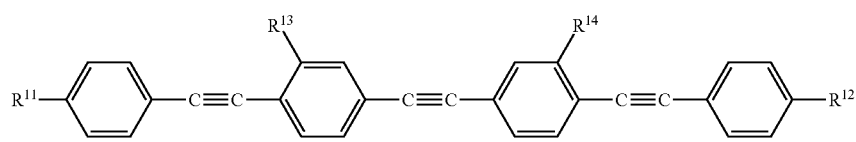

in which $L^{11}$ denotes alkyl having 1 to 6 C atoms, alkenyl having 2 to 6 C atoms, cycloalkyl having 3 to 6 C atoms or cycloalkenyl having 4 to 6 C atoms, preferably $CH_3$, $C_2H_5$, n-$C_3H_7$, (—$(CH_2)_2CH_3$), i-$C_3H_7$ (—$CH(CH_3)_2$), —$CH=CH_2$, cyclopropyl, cyclobutyl, cyclopentyl, cyclohexyl, cyclopent-1-enyl or cyclohex-1-enyl, and particularly preferably $CH_3$, $C_2H_5$, cyclopropyl or cyclobutyl, $X^{11}$ denotes H, alkyl having 1 to 3 C atoms or halogen, preferably H, F or Cl, and particularly preferably H, F or $CH_3$, even more preferably H or F and very particularly preferably F, and the other parameters have the respective meanings indicated above for formula I, and preferably $R^{11}$ denotes unfluorinated alkyl having 1 to 7 C atoms, and $R^{12}$ denotes unfluorinated alkyl having 1 to 7 C atoms or unfluorinated alkoxy having 1 to 7 C atoms.

In a particularly preferred embodiment of the present invention, the compounds of the formula I-1 are selected from the group of the compounds of the formulae I-1a-1 to I-1a-12 and I-1b-1 to I-1b-12

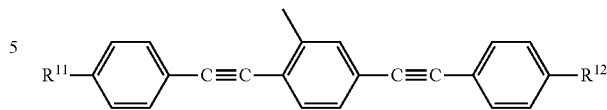

I-1a-1

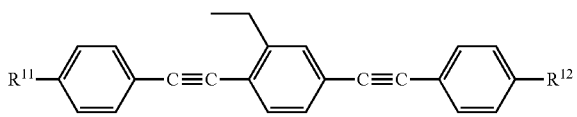

I-1a-2

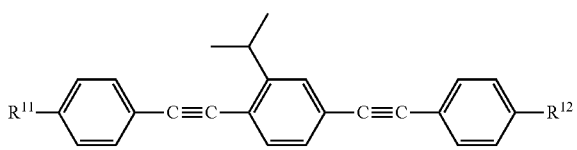

I-1a-3

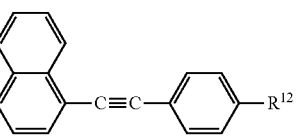

I-2

I-4

-continued

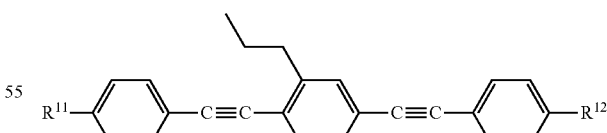

I-1a-4

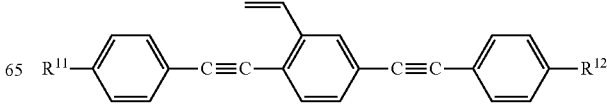

I-1a-5

-continued
I-1a-6
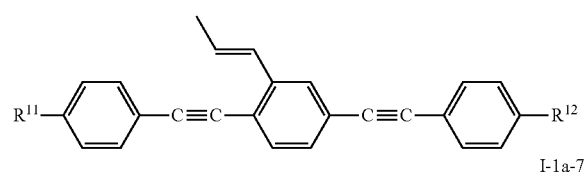
I-1a-7
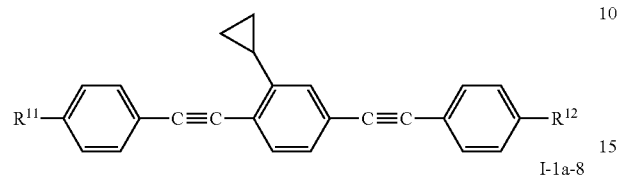
I-1a-8
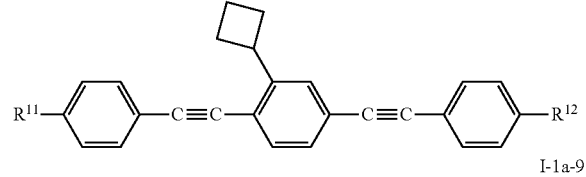
I-1a-9
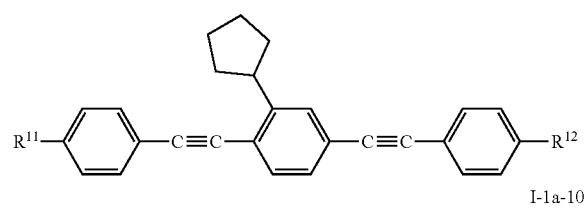
I-1a-10
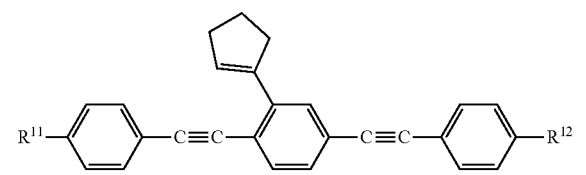
I-1a-11
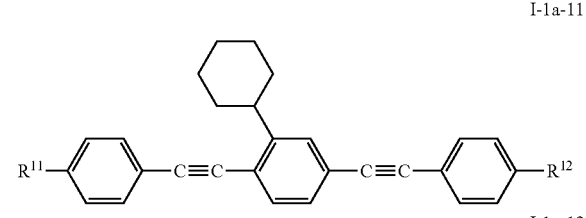
I-1a-12
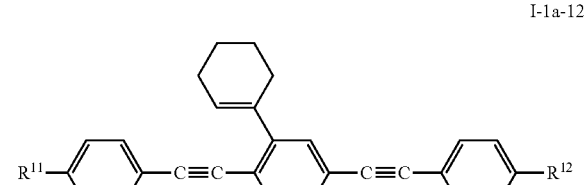
I-1b-1
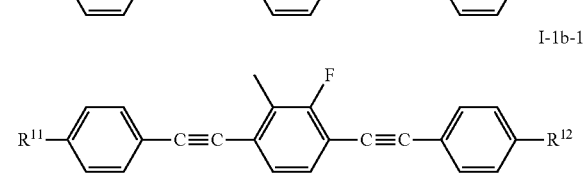
I-1b-2
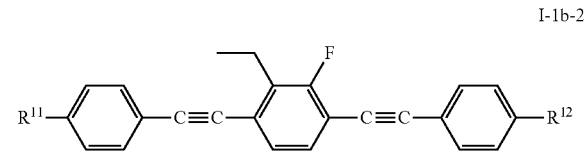
-continued
I-1b-3
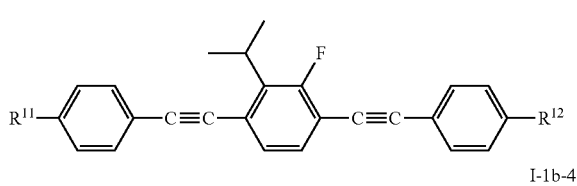
I-1b-4
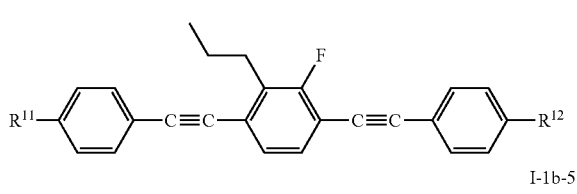
I-1b-5
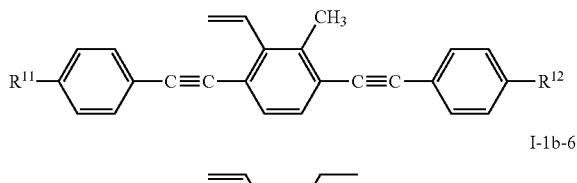
I-1b-6
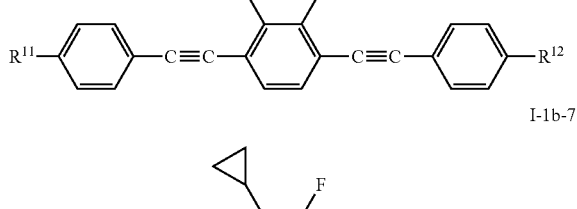
I-1b-7
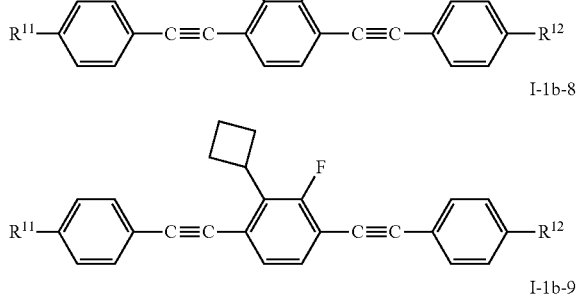
I-1b-8
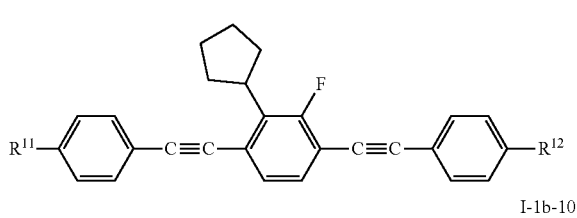
I-1b-9
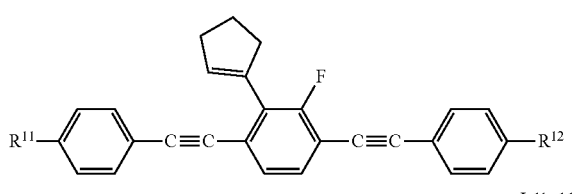
I-1b-10
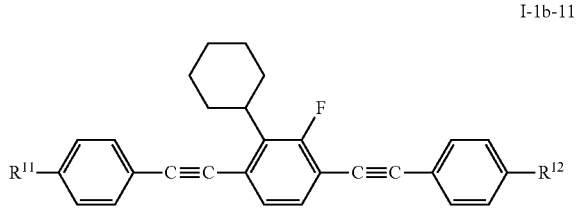
I-1b-11

I-1b-12

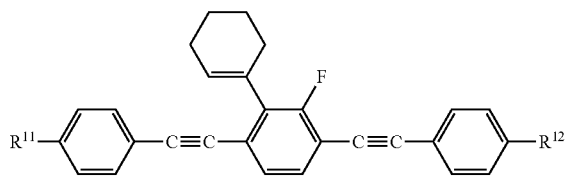

in which the parameters have the meanings as given above under formula I-1, and preferably $R^{11}$ and $R^{12}$, independently of one another, denote an alkyl radical having 2 to 7 C atoms, for example a propyl or hexyl radical, or each denote a propyl, butyl, pentyl or hexyl radical.

In a very particularly preferred embodiment of the present invention, the compounds of the formula I are selected from the group of the compounds of the formulae I-1a-2, I-1a-5, I-1a-7, I-1a-8, I-1a-9, I-1a-10, I-1b-5, I-1b-7, I-1b-8, I-1 b-9, I-1 b-10, where the parameters have the meaning given above, and particularly preferably $R^{11}$ and $R^{12}$, independently of one another, denote unfluorinated alkyl having 1 to 7 C atoms or unfluorinated alkoxy having 1 to 6 C atoms, particularly preferably one of $R^{11}$ and $R^{12}$ denotes alkyl and the other denotes alkyl or alkoxy, and very particularly preferably $R^{11}$ and $R^{12}$ have different meanings from one another.

In a preferred embodiment of the present invention, the liquid-crystal medium comprises one or more compounds of the formula I-2, in which preferably $R^{11}$ and $R^{12}$, independently of one another, denote an alkyl radical having 2 to 7 C atoms, for example a propyl or hexyl radical, or each denote a propyl, butyl, pentyl or hexyl radical.

In a preferred embodiment of the present invention the compounds of the formula I-3 are selected from the group of the compounds of the formulae I-3a-1 to I-3a-3 and I-3b-1 to I-3b-3, preferably I-3a-2, I-3b-2, I-3a-1

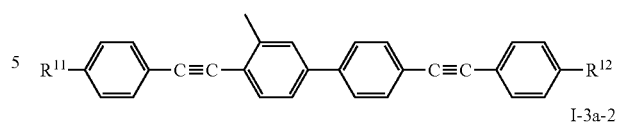

I-3a-2

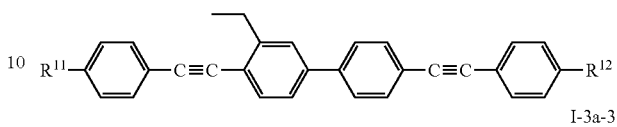

I-3a-3

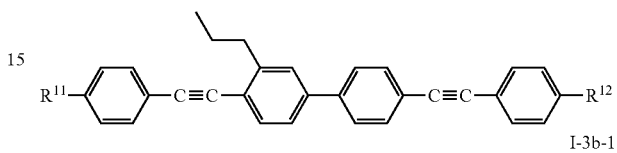

I-3b-1

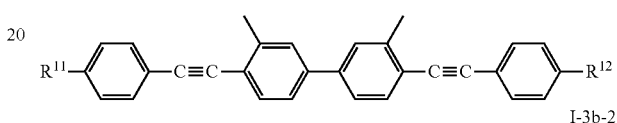

I-3b-2

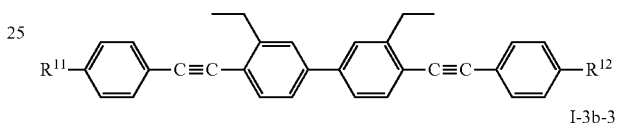

I-3b-3

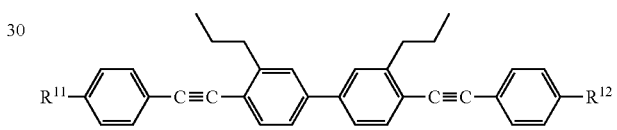

in which the parameters have the meanings given above under formula I-3, and preferably $R^{11}$ and $R^{12}$, independently of one another, denote an alkyl radical having 2 to 7 C atoms, for example a propyl or hexyl radical, or each denote a propyl, butyl, pentyl or hexyl radical.

In a preferred embodiment of the present invention, the compounds of the formula I-4 are selected from the group of the compounds of the formulae I-4a-1 to I-4a-3 and I-4b-1 to I-4b-3, preferably I-4b-2, I-4a-1

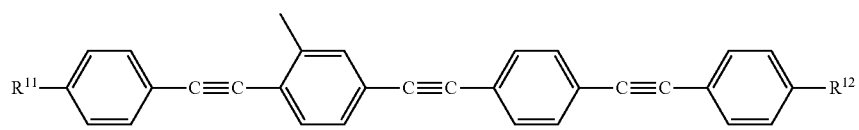

I-4a-2

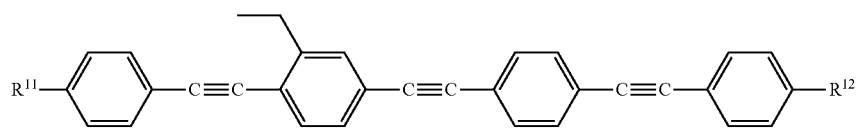

I-4a-3

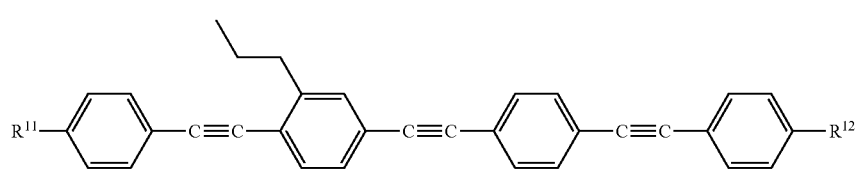

-continued

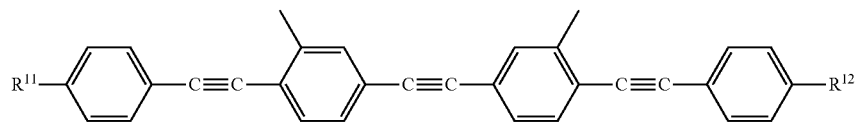

I-4b-1

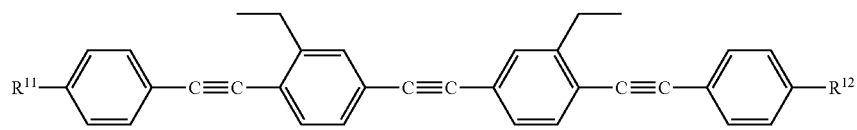

I-4b-2

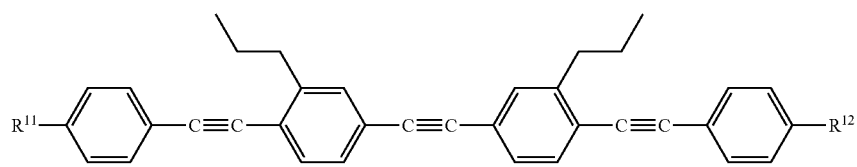

I-4b-3 in which the parameters have the meanings given above under formula I-4, and preferably $R^{11}$ and $R^{12}$, independently of one another, denote an alkyl radical having 2 to 7 C atoms, for example a propyl or hexyl radical, or each denote a propyl, butyl, pentyl or hexyl radical.

In a preferred embodiment of the present invention the liquid-crystalline medium comprises one or more compounds selected from the group of the compounds of the formulae II and III:

wherein $R^{21}$ denotes unfluorinated alkyl or unfluorinated alkoxy, each having 1 to 15 C atoms, or unfluorinated alkenyl, unfluorinated alkenyloxy or unfluorinated alkoxyalkyl, each having 2 to 15 C atoms, preferably alkyl, particularly preferably n-alkyl, $R^{22}$ denotes H, unfluorinated alkyl or unfluorinated alkoxy, each having 1 to 5, preferably 1 to 3, particularly preferably 3, C atoms, $L^{21}$, $L^{22}$, $L^{23}$,

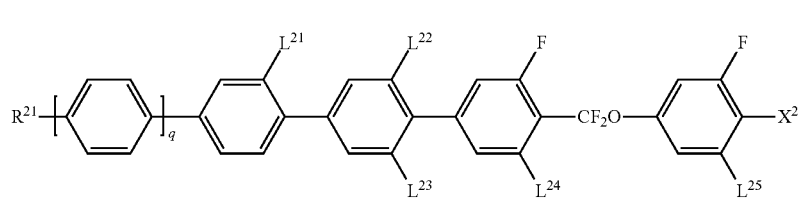

II

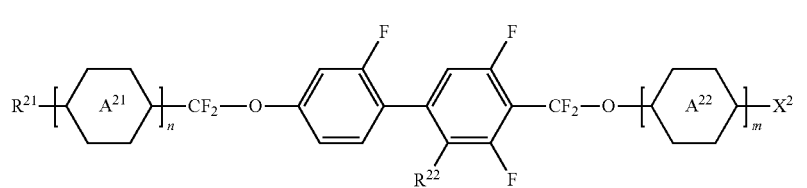

III $L^{24}$ and $L^{25}$ denote, independently from one another, H or F,

independently of one another and, if they occur more than once, these also in each case independently of one another, denote

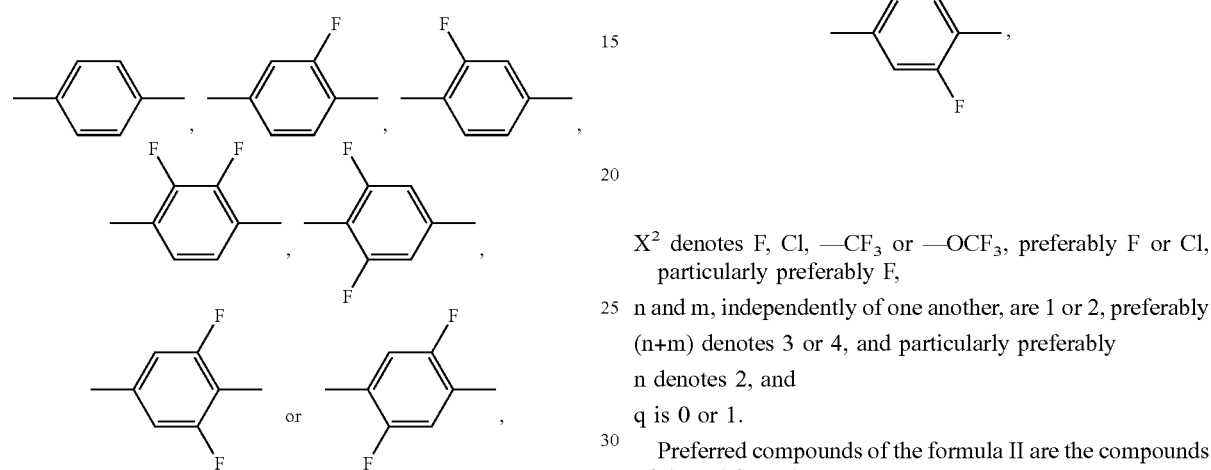

preferably

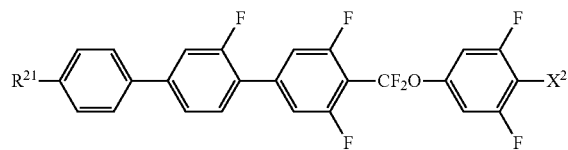

$X^2$ denotes F, Cl, —$CF_3$ or —$OCF_3$, preferably F or Cl, particularly preferably F, n and m, independently of one another, are 1 or 2, preferably (n+m) denotes 3 or 4, and particularly preferably n denotes 2, and q is 0 or 1.

Preferred compounds of the formula II are the compounds of the subformula II-1 to II-6

II-1

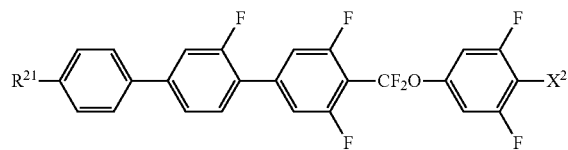

II-2

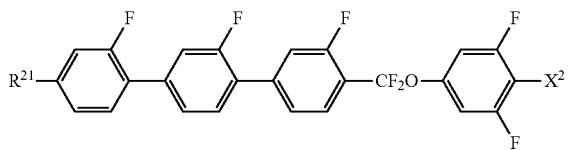

II-3

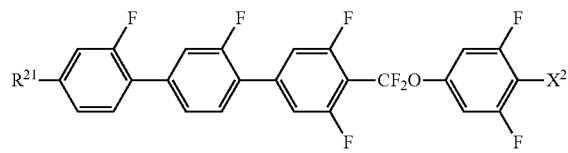

II-4

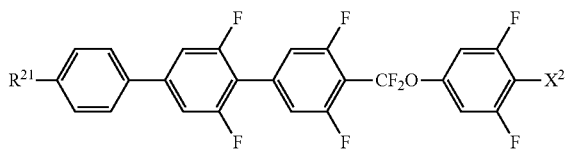

II-5

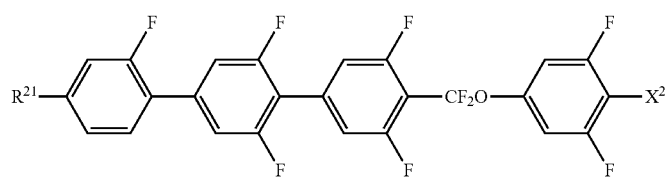

II-6

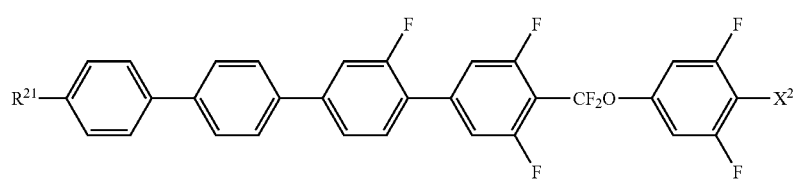

in which $R^{21}$ and $X^2$ have the meanings given above, and $R^{21}$ preferably denotes alkyl or alkenyl having 2 to 7 C atoms and $X^2$ preferably denotes F or CN.

The compounds of formula II are very preferably selected from the compounds of formulae II-4 and II-5.

Preferred compounds of the formula III are the compounds of the subformulae III-1 and III-2:

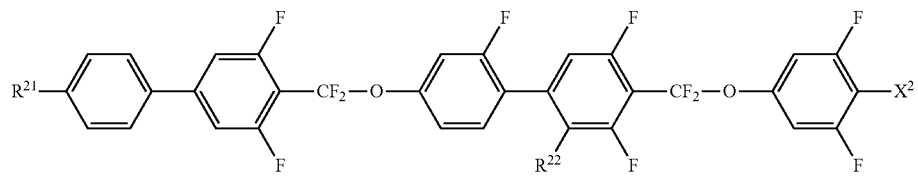
III-1

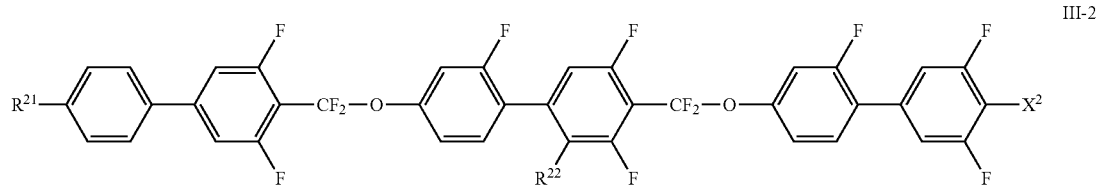
III-2 in which $R^{21}$, $R^{22}$ and $X^2$ have the respective meanings given above.

In a preferred embodiment of the present invention, the liquid-crystalline medium comprises one or more compounds of formula IV:

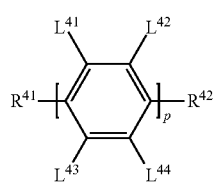
IV in which
$R^{41}$ and $R^{42}$, independently of one another, have one of the meanings indicated above for $R^{11}$ under formula I,
$L^{41}$ to $L^{44}$ on each appearance, in each case independently of one another, denote H, alkyl having 1 to 5 C atoms, F or Cl, and
p denotes an integer in the range from 7 to 14, preferably from 8 to 12 and particularly preferably from 9 to 10, and preferably
at least two of the substituents
$L^{41}$ to $L^{44}$ present have a meaning other than H, and
$R^{41}$ denotes $C_nH_{2n+1}$ or $CH_2=CH-(CH_2)_z$, and
$R^{42}$ denotes $C_mH_{2m+1}$ or $O-C_mH_{2m+1}$ or $(CH_2)_z-CH=CH_2$,
and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

In a preferred embodiment of the present application, the liquid-crystal medium additionally comprises one or more compounds selected from the group of compounds of the formulae V, VI, VII, VIII and IX:

V

-continued

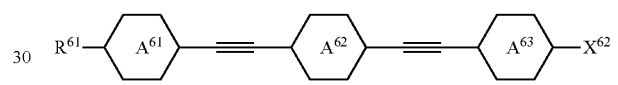
VI

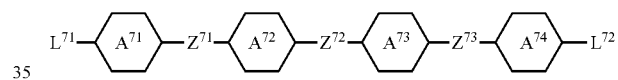
VII

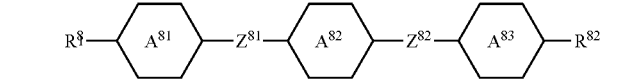
VIII

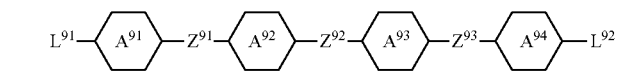
IX in which
$L^{51}$ denotes $R^{51}$ or $X^{51}$,
$L^{52}$ denotes $R^{52}$ or $X^{52}$,
$R^{51}$ and $R^{52}$, independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl,
$X^{51}$ and $X^{52}$, independently of one another, denote H, F, Cl, —CN, —NCS, —SF$_5$, fluorinated alkyl or fluorinated alkoxy having 1 to 7 C atoms or fluorinated alkenyl, fluorinated alkenyloxy or fluorinated alkoxyalkyl having 2 to 7 C atoms, preferably fluorinated alkoxy, fluorinated alkenyloxy, F or Cl, and

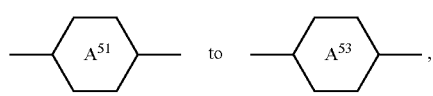

independently of one another, denote

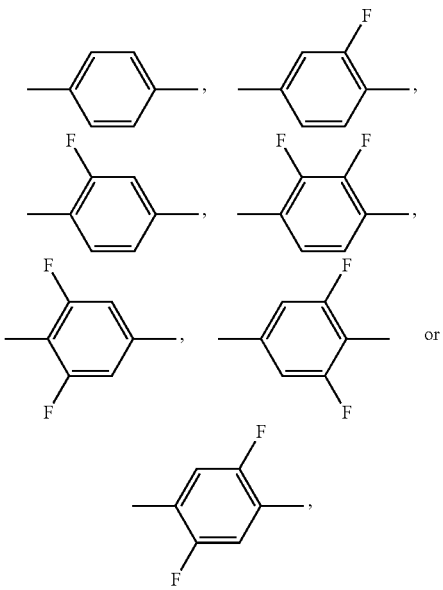

or preferably

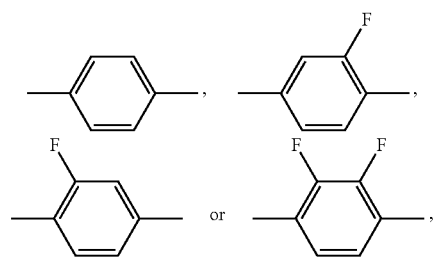

- R$^{61}$ denotes branched or unbranched alkyl having 1 to 15 C atoms or branched or unbranched alkenyl having 2 to 15 C atoms, where, in addition, one or more non-adjacent "—CH$_2$—" groups in these radicals may be replaced by —O— and/or one or more H atoms may be replaced by halogen atoms, preferably by F atoms,
- X$^{62}$ denotes F, Cl, fluorinated alkyl having 1 to 4 C atoms, fluorinated alkoxy having 1 to 4 C atoms, fluorinated alkenyl having 2 to 4 C atoms, fluorinated alkenyloxy having 2 to 4 C atoms, CN, NCS or SF$_5$, preferably F, —NCS, CF$_3$ or OCF$_3$, particularly preferably F or NCS,

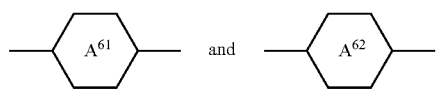

independently of one another, denote

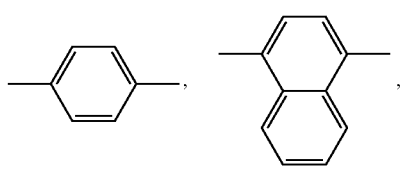

-continued

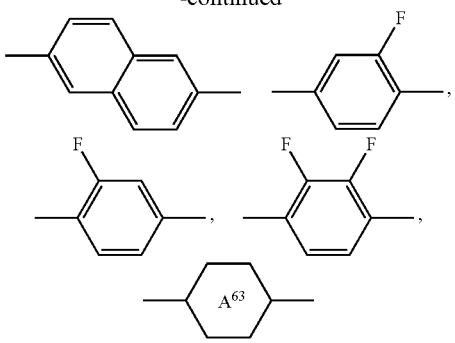

denotes

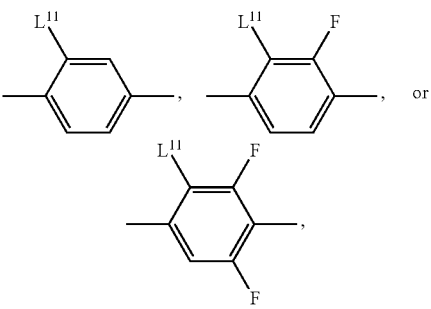

- L$^{11}$ denotes H or alkyl having 1 to 12 C atoms,
- L$^{71}$ denotes R$^{71}$ or X$^{71}$,
- L$^{72}$ denotes R$^{72}$ or X$^{72}$,
- R$^{71}$ and R$^{72}$, independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl,
- X$^{71}$ and X$^{72}$, independently of one another, denote H, F, Cl, —CN, —NCS, —SF$_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and
- Z$^{71}$ to Z$^{73}$, independently of one another, denote trans-CH=CH—, trans-CF=CF—, —C≡C— or a single bond, preferably one or more of them denote a single bond, particularly preferably all denote a single bond and

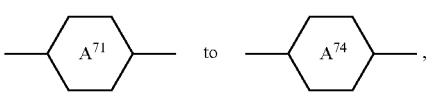

independently of one another, denote

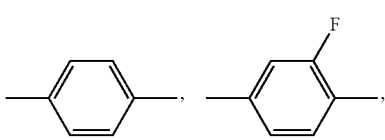

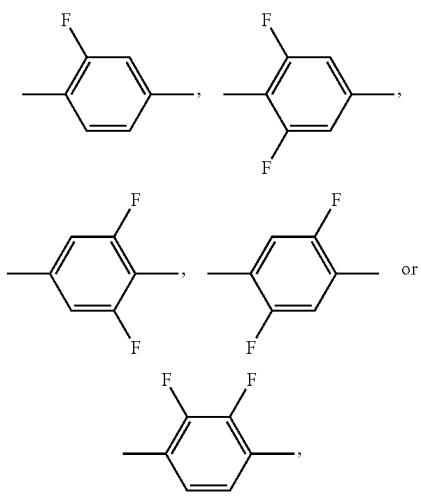

preferably

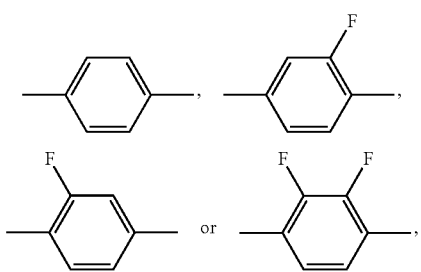

$R^{81}$ and $R^{82}$, independently of one another, denote H, unfluorinated alkyl or alkoxy having 1 to 15, preferably 3 to 10, C atoms or unfluorinated alkenyl, alkenyloxy or alkoxyalkyl having 2 to 15, preferably 3 to 10, C atoms, preferably unfluorinated alkyl or alkenyl, one of $Z^{81}$ and $Z^{82}$ denotes trans-CH=CH—, trans-CF=CF— or —C≡C— and the other, independently thereof, denotes trans-CH=CH—, trans-CF=CF— or a single bond, preferably one of them denotes —C≡C— or trans-CH=CH— and the other denotes a single bond, and

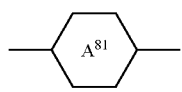

denotes

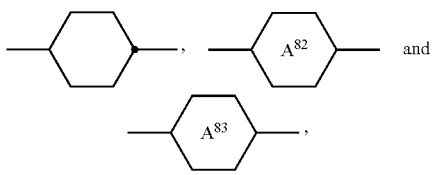

independently of one another, denote

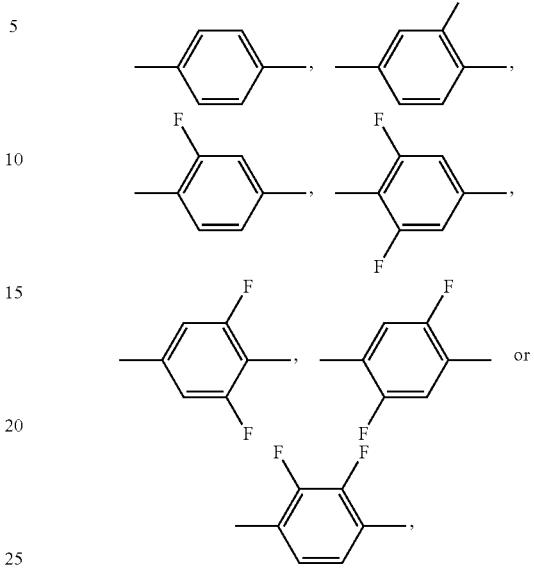

$L^{91}$ denotes $R^{91}$ or $X^{91}$,
$L^{92}$ denotes $R^{92}$ or $X^{92}$,
$R^{91}$ and $R^{92}$, independently of one another, denote H, unfluorinated alkyl or alkoxy having 1 to 15, preferably 3 to 10, C atoms or unfluorinated alkenyl, alkenyloxy or alkoxyalkyl having 2 to 15, preferably 3 to 10, C atoms, preferably unfluorinated alkyl or alkenyl,
$X^{91}$ and $X^{92}$, independently of one another, denote H, F, Cl, —CN, —NCS, —SF$_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and
$Z^{91}$ to $Z^{93}$, independently of one another, denote trans-CH=CH—, trans-CF=CF—, —C≡C— or a single bond, preferably one or more of them denotes a single bond, and particularly preferably all denote a single bond,

denotes

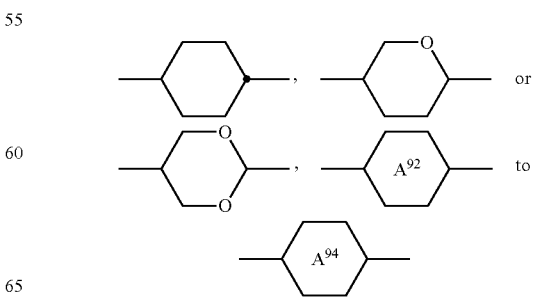

to independently of one another, denote

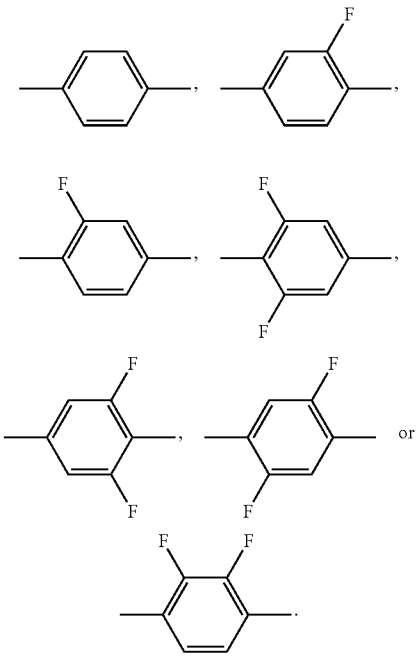

In a preferred embodiment of the present invention, the liquid-crystal medium comprises one or more compounds of the formula V, preferably selected from the group of the compounds of the formulae V-1 to V-3, preferably of the formulae V-1 and/or V-2 and/or V-3, preferably of the formulae V-1 and V-2:

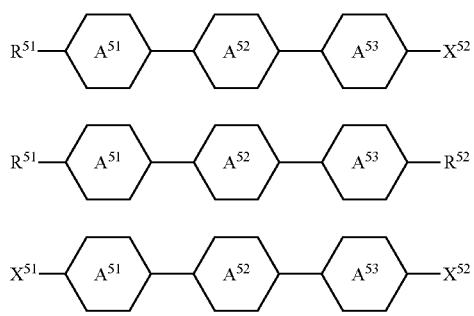

in which the parameters have the respective meanings indicated above for formula V and preferably $R^{51}$ denotes unfluorinated alkyl having 1 to 7 C atoms or unfluorinated alkenyl having 2 to 7 C atoms, $R^{52}$ denotes unfluorinated alkyl having 1 to 7 C atoms or unfluorinated alkenyl having 2 to 7 C atoms or unfluorinated alkoxy having 1 to 7 C atoms, $X^{51}$ and $X^{52}$, independently of one another, denote F, Cl, —$OCF_3$, —$CF_3$, —CN, —NCS or —$SF_5$, preferably F, Cl, —$OCF_3$ or —CN.

The compounds of the formula V-1 are preferably selected from the group of the compounds of the formulae V-1a to V-1d, preferably V-1c and V-1d:

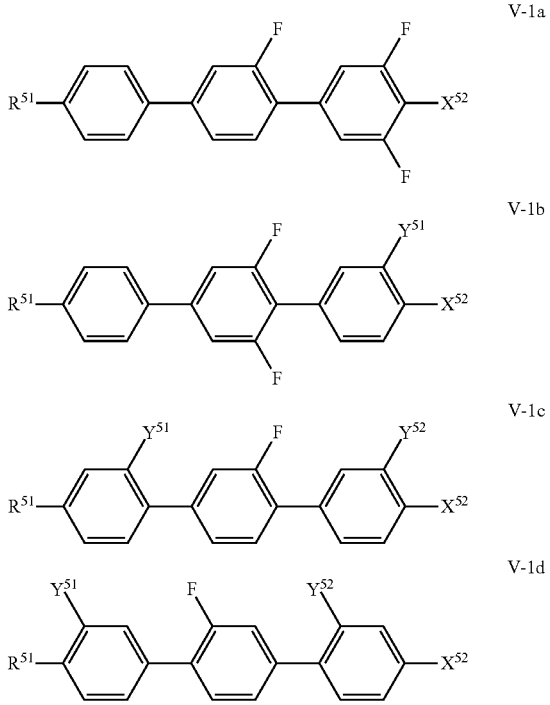

in which the parameters have the respective meanings indicated above for formula V-1 and in which $Y^{51}$ and $Y^{52}$, in each case independently of one another, denote H or F, and preferably $R^{51}$ denotes alkyl or alkenyl, and $X^{51}$ denotes F, Cl or —$OCF_3$.

The compounds of the formula V-2 are preferably selected from the group of the compounds of the formulae V-2a to V-2e and/or from the group of the compounds of the formulae V-2f and V-2g:

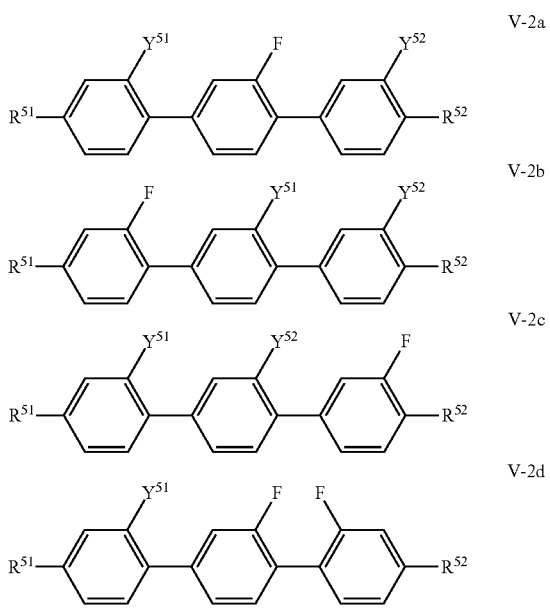

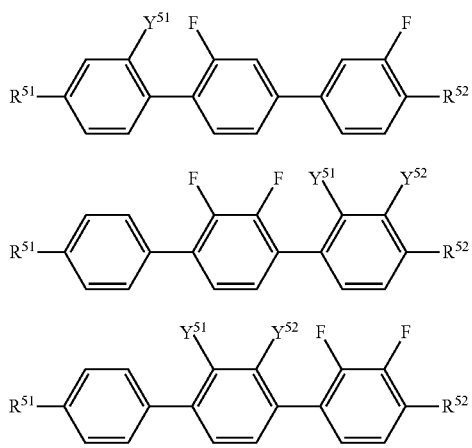

V-2e

V-2f

V-2g where in each case the compounds of the formula V-2a are excluded from the compounds of the formulae V-2b and V-2c, the compounds of the formula V-2b are excluded from the compounds of the formula V-2c and the compounds of the formula V-2e are excluded from the compounds of the formula V-2f, and in which the parameters have the respective meanings indicated above for formula V-1 and in which $Y^{51}$ and $Y^{52}$, in each case independently of one another, denote H or F, and preferably $Y^{51}$ and $Y^{52}$ denotes H and the other denotes H or F, preferably likewise denotes H.

The compounds of the formula V-3 are preferably compounds of the formula V-3a:

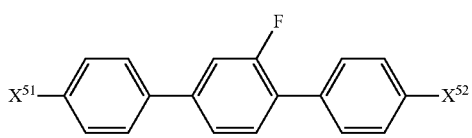

V-3a in which the parameters have the respective meanings indicated above for formula V-1 and in which preferably $X^{51}$ denotes F, Cl, preferably F, $X^{52}$ denotes F, Cl or —OCF$_3$, preferably —OCF$_3$.

The compounds of the formula V-1a are preferably selected from the group of the compounds of the formulae V-1a-1 and V-1a-2, more preferably these compounds of the formula V predominantly consist, even more preferably essentially consist and very particularly preferably completely consist thereof:

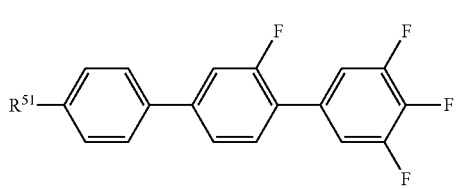

V-1a-1

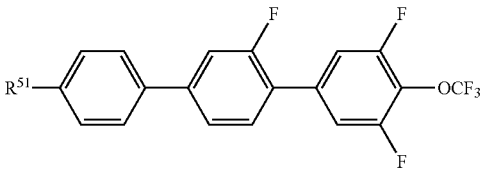

V-1a-2 in which $R^{51}$ has the meaning indicated above and preferably denotes $C_nH_{2n+1}$, in which n denotes an integer in the range from 0 to 7, preferably in the range from 1 to 5 and particularly preferably 3 or 7.

The compounds of the formula V-1b are preferably compounds of the formula V-1b-1:

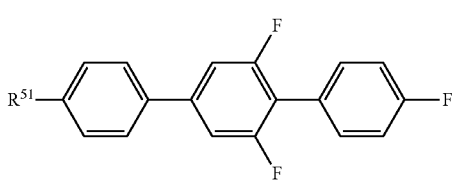

V-1b-1 in which $R^{51}$ has the meaning indicated above and preferably denotes $C_nH_{2n+1}$, in which n denotes an integer in the range from 0 to 15, preferably in the range from 1 to 7 and particularly preferably 1 to 5.

The compounds of the formula V-1c are preferably selected from the group of the compounds of the formulae V-1c-1 to V-1c-4, particularly preferably selected from the group of the compounds of the formulae V-1c-1 and V-1c-2:

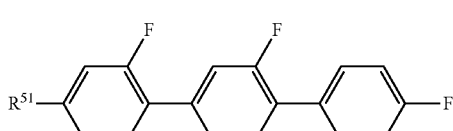

V-1c-1

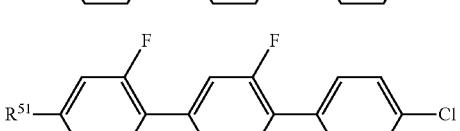

V-1c-2

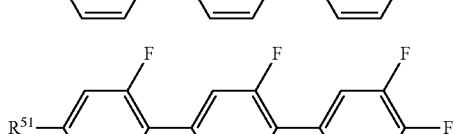

V-1c-3

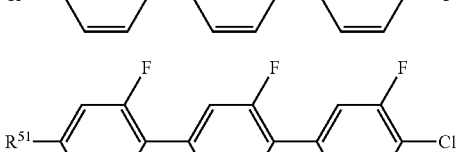

V-1c-4 in which $R^{51}$ has the meaning indicated above and preferably denotes $C_nH_{2n+1}$, in which n denotes an integer in the range from 0 to 15, preferably in the range from 1 to 7 and particularly preferably 1 to 5.

The compounds of the formula V-1d are preferably selected from the group of the compounds of the formulae V-1d-1 and V-1d-2, particularly preferably the compound of the formula V-1d-2:

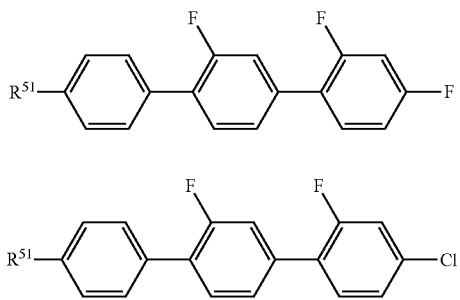

in which
R$^{51}$ has the meaning indicated above and preferably denotes C$_n$H$_{2n+15}$ in which n denotes an integer in the range from 0 to 15, preferably in the range from 1 to 7 and particularly preferably 1 to 5.

The compounds of the formula V-2a are preferably selected from the group of the compounds of the formulae V-2a-1 and V-2a-2, particularly preferably the compounds of the formula V-2a-1:

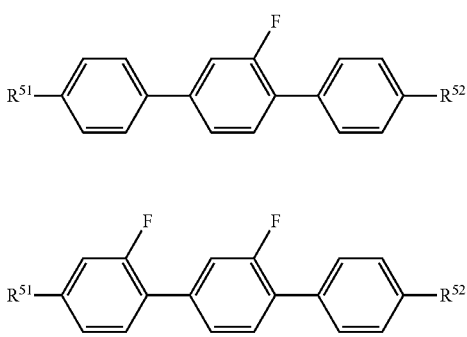

in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

Preferred combinations of (R$^{51}$ and R$^{52}$), in particular in the case of formula V-2a-1, are (C$_n$H$_{2n+1}$ and C$_m$H$_{2m+1}$), (C$_n$H$_{2n+1}$ and O—C$_m$H$_{2m+1}$), (CH$_2$=CH—(CH$_2$)$_z$ and C$_m$H$_{2m+1}$), (CH$_2$=CH—(CH$_2$)$_z$ and O—C$_m$H$_{2m+1}$) and (C$_n$H$_{2n+1}$ and (CH$_2$)$_z$—CH=CH$_2$).

Preferred compounds of the formula V-2b are the compounds of the formula V-2b-1:

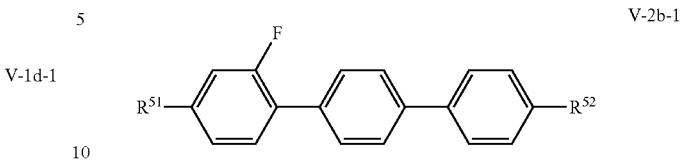

in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combination of (R$^{51}$ and R$^{52}$) here is, in particular, (C$_n$H$_{2n+1}$ and C$_m$H$_{2m+1}$).

Preferred compounds of the formula V-2c are the compounds of the formula V-2c-1:

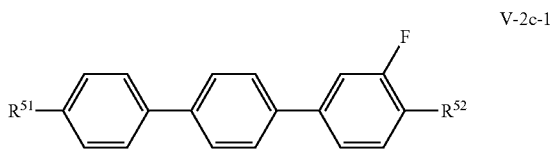

in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combination of (R$^{51}$ and R$^{52}$) here is, in particular, (C$_n$H$_{2n+1}$ and C$_m$H$_{2m+1}$).

Preferred compounds of the formula V-2d are the compounds of the formula V-2d-1:

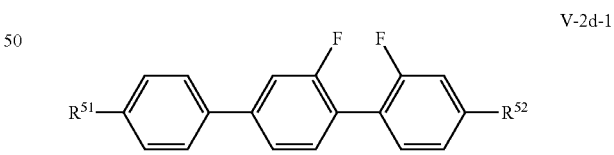

in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combination of (R$^{51}$ and R$^{52}$) here is, in particular, (C$_n$H$_{2n+1}$ and C$_m$H$_{2m+1}$).

Preferred compounds of the formula V-2e are the compounds of the formula V-2e-1:

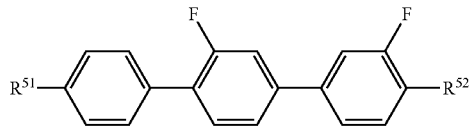

in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combination of (R$^{51}$ and R$^{52}$) here is, in particular, (C$_n$H$_{2n+1}$ and O—C$_m$H$_{2m+1}$).

Preferred compounds of the formula V-2f are the compounds of the formula V-2f-1:

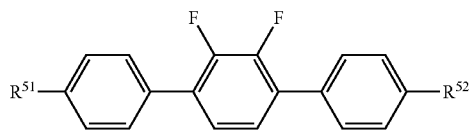

in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{51}$ and R$^{52}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and C$_m$H$_{2m+1}$).

Preferred compounds of the formula V-2g are the compounds of the formula V-2g-1:

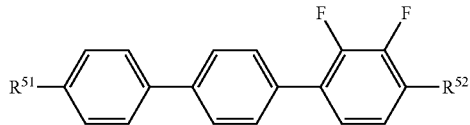

in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{51}$ and R$^{52}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and O—C$_m$H$_{2m+1}$).

In a preferred embodiment of the present invention, the liquid-crystal medium comprises one or more compounds of the formula VI, preferably selected from the group of the compounds of the formulae

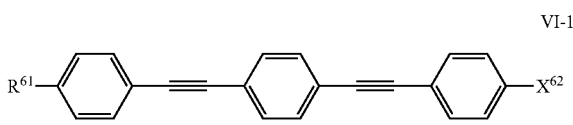

VI-1

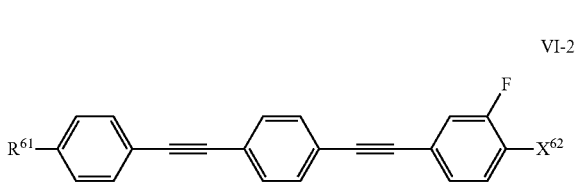

VI-2

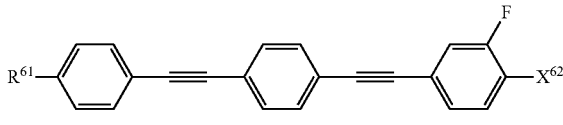

VI-3

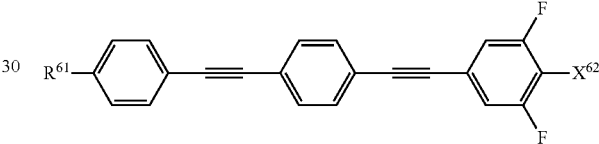

VI-4

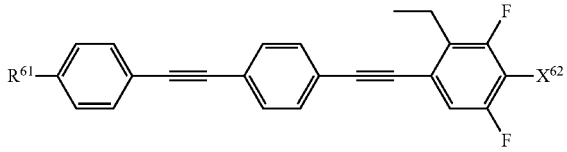

VI-5

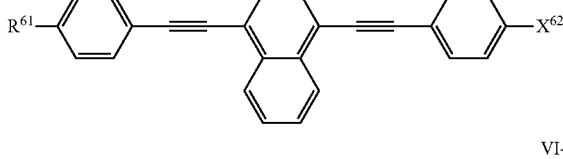

VI-6

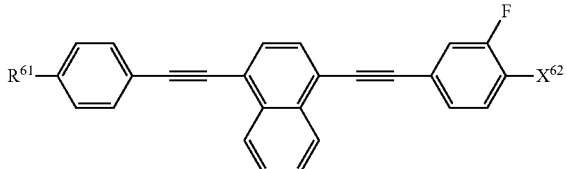

VI-7

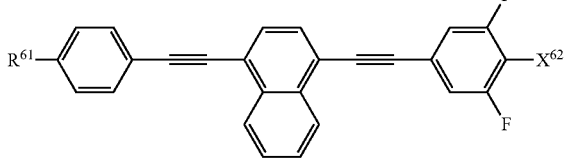

VI-8

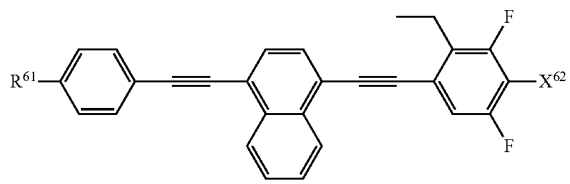

VI-9

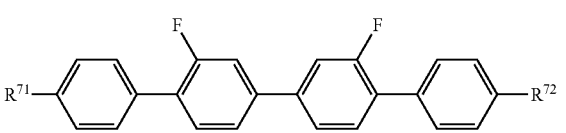

VI-10

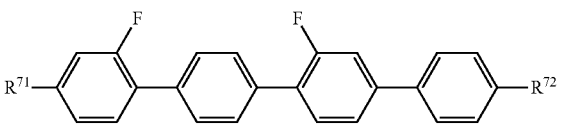

VI-11

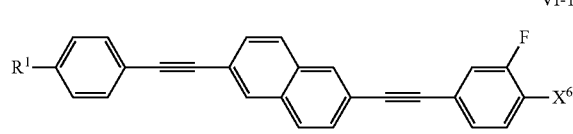

VI-12

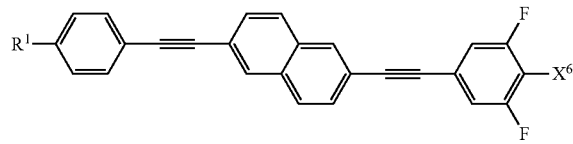

VII-3

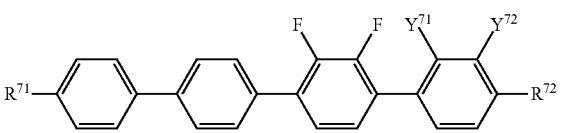

VII-4

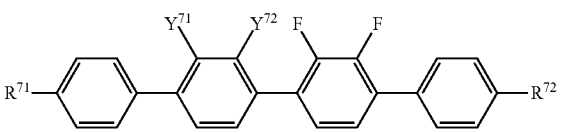

VII-5, VII-6

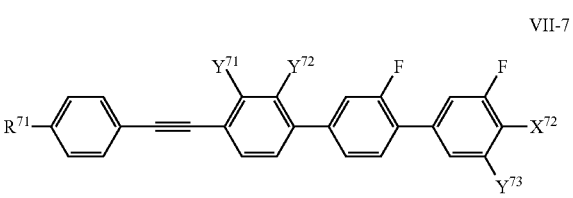

VII-7 wherein $R^{61}$ and $X^{62}$ have the respective meanings indicated above for formula VI and preferably $X^{62}$ denotes F, —NCS or —OCF$_3$, $R^{61}$ denotes $C_mH_{2m+1}$ or O—$C_mH_{2m+1}$ or $(CH_2)_z$—CH=CH$_2$, n and m, independently of one another, denote an integer in the range from 0 to 15, preferably in the range from 1 to 7 and particularly preferably 1 to 5, and z denotes 0, 1, 2, 3 or 4, preferably 0 or 2.

The compounds of the formula VII are preferably selected from the group of the compounds of the formulae VII-1 to VII-6:

VII-1

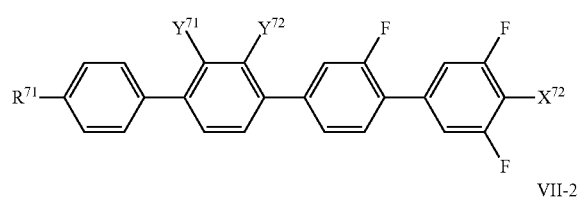

VII-2

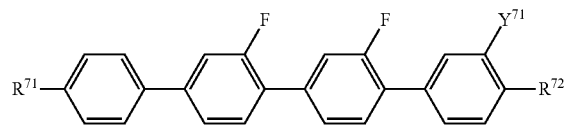

where the compounds of the formula VII-5 are excluded from the compounds of the formula VII-6, and in which the parameters have the respective meanings indicated above for formula VII, $Y^{71}$, $Y^{72}$, $Y^{73}$ independently from one another, denote H or F, and preferably $R^{71}$ denotes unfluorinated alkyl or alkoxy, each having 1 to 7 C atoms, or unfluorinated alkenyl having 2 to 7 C atoms, $R^{72}$ denotes unfluorinated alkyl or alkoxy, each having 1 to 7 C atoms, or unfluorinated alkenyl having 2 to 7 C atoms, $X^{72}$ denotes F, Cl; NCS or —OCF$_3$, preferably F or NCS, and particularly preferably $R^{71}$ has the meaning indicated above and preferably denotes $C_nH_{2n+1}$ or CH$_2$=CH—(CH$_2$)$_z$, and $R^{72}$ has the meaning indicated above and preferably denotes $C_mH_{2m+1}$ or O—$C_mH_{2m+1}$ or $(CH_2)_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The compounds of the formula VII-1 are preferably selected from the group of the compounds of the formulae VII-1a to VII-1d:

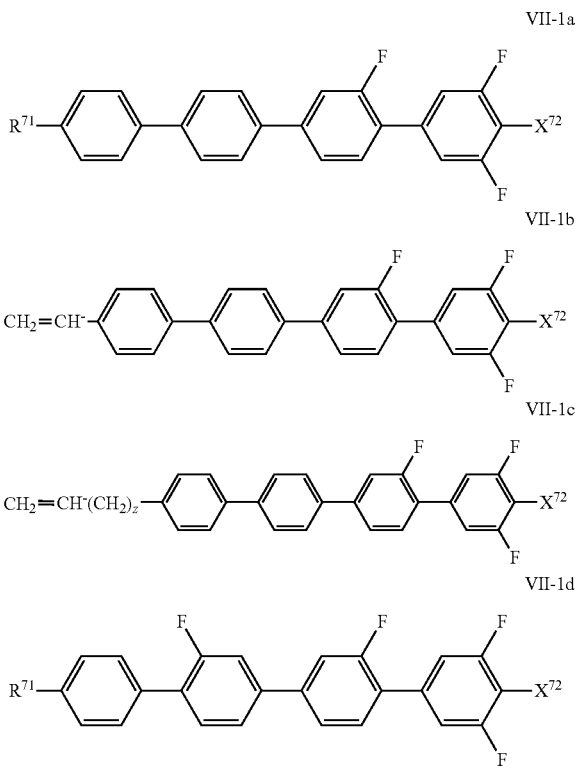

in which $X^{72}$ has the meaning given above for formula VII-2 and
$R^{71}$ has the meaning indicated above and preferably denotes $C_nH_{2n+1}$, in which
n denotes 1 to 7, preferably 2 to 6, particularly preferably 2, 3 or 5, and
z denotes 0, 1, 2, 3 or 4, preferably 0 or 2, and
$X^{72}$ preferably denotes F.

The compounds of the formula VII-2 are preferably selected from the group of the compounds of the formulae VII-2a and VII-2b, particularly preferably of the formula VII-2a:

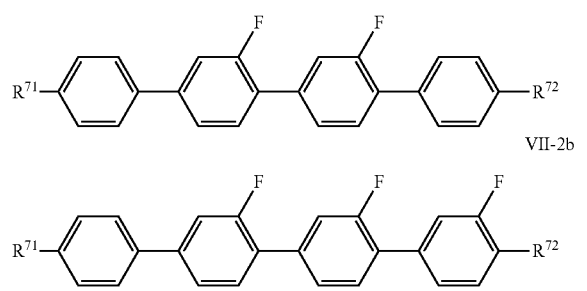

in which
$R^{71}$ has the meaning indicated above and preferably denotes $C_nH_{2n+1}$ or $CH_2=CH-(CH_2)_z$, and
$R^{72}$ has the meaning indicated above and preferably denotes $C_mH_{2m+1}$ or $O-C_mH_{2m+1}$ or $(CH_2)_z-CH=CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and $O-C_mH_{2m+1}$), particularly preferably ($C_nH_{2n+1}$ and $C_mH_{2m+1}$).

The compounds of the formula VII-3 are preferably compounds of the formula VII-3a:

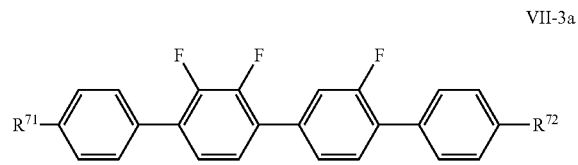

in which
$R^{71}$ has the meaning indicated above and preferably denotes $C_nH_{2n+1}$ or $CH_2=CH-(CH_2)_z$, and
$R^{72}$ has the meaning indicated above and preferably denotes $C_mH_{2m+1}$ or $O-C_mH_{2m+1}$ or $(CH_2)_z-CH=CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and $O-C_mH_{2m+1}$), particularly preferably ($C_nH_{2n+1}$ and $C_mH_{2m+1}$).

The compounds of the formula VII-4 are preferably compounds of the formula VII-4a:

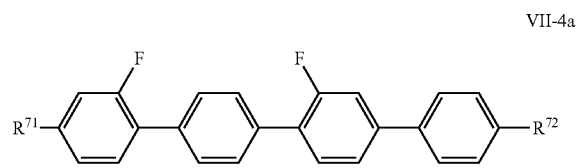

in which
$R^{71}$ has the meaning indicated above and preferably denotes $C_nH_{2n+1}$ or $CH_2=CH-(CH_2)_z$, and
$R^{72}$ has the meaning indicated above and preferably denotes $C_mH_{2m+1}$ or $O-C_mH_{2m+1}$ or $(CH_2)_z-CH=CH_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and $O-C_mH_{2m+1}$), particularly preferably ($C_nH_{2n+1}$ and $C_mH_{2m+1}$).

The compounds of the formula VII-5 are preferably selected from the group of the compounds of the formulae VII-5a and VII-5b, more preferably of the formula VII-5a:

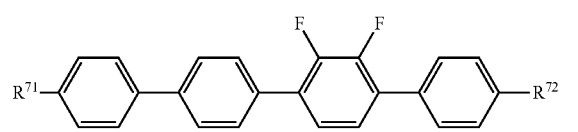

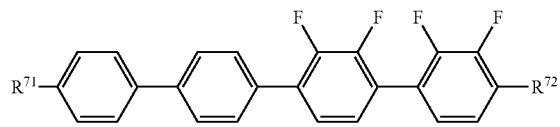
VII-5b in which
R$^{71}$ has the meaning indicated above and preferably denotes
  C$_n$H$_{2n+1}$ or CH$_2$=CH—(CH$_2$)$_z$, and
R$^{72}$ has the meaning indicated above and preferably denotes
  C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{71}$ and R$^{72}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and C$_m$H$_{2m+1}$).

The compounds of the formula VII-6 are preferably selected from the group of the compounds of the formulae VII-6a and VII-6b:

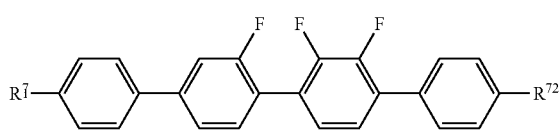
VII-6a

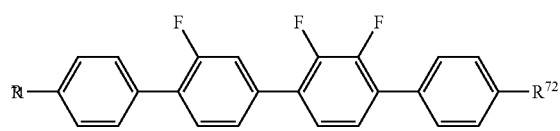
VII-6b in which
R$^{71}$ has the meaning indicated above and preferably denotes
  C$_n$H$_{2n+1}$ or CH$_2$=CH—(CH$_2$)$_z$, and
R$^{72}$ has the meaning indicated above and preferably denotes
  C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{71}$ and R$^{72}$) here are, in particular, (C$_n$H$_{2n+1}$ and C$_m$H$_{2m+1}$) and (C$_n$H$_{2n+1}$ and O—C$_m$H$_{2m-o}$), particularly preferably (C$_n$H$_{2n+1}$ and C$_m$H$_{2m+1}$).

The compounds of the formula VII-7 are preferably selected from the group of the compounds of the formulae VII-7a to VII-7d:

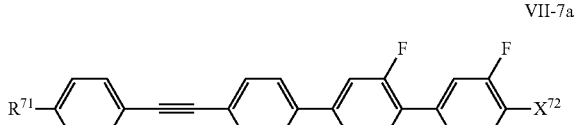
VII-7a

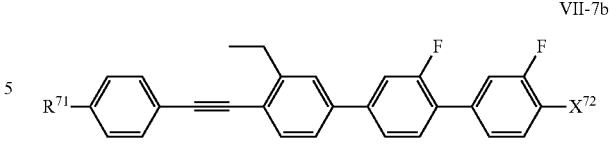
VII-7b

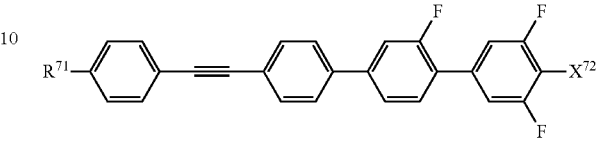
VII-7c

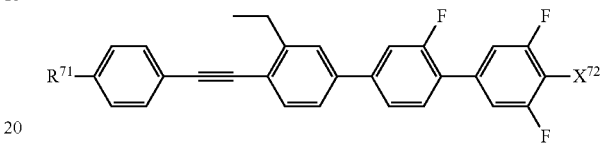
VII-7d in which
R$^{71}$ has the meaning indicated above and preferably denotes
  C$_n$H$_{2n+1}$ or CH$_2$=CH—(CH$_2$)$_z$,
X$^{72}$ denotes F, —OCF$_3$ or —NCS,
n denotes an integer in the range from 0 to 15, preferably in the range from 1 to 7 and particularly preferably 1 to 5, and,
z denotes 0, 1, 2, 3 or 4, preferably 0 or 2.

The compounds of the formula VIII are preferably selected from the group of the compounds of the formulae VIII-1 to VIII-3, more preferably these compounds of the formula VIII predominantly consist, even more preferably essentially consist and very particularly preferably completely consist thereof:

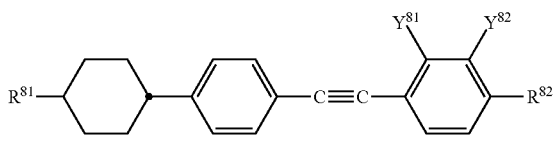
VIII-1

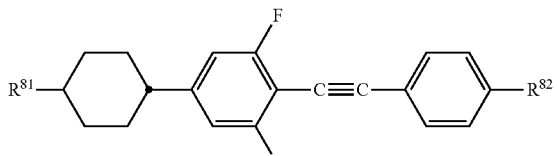
VIII-2

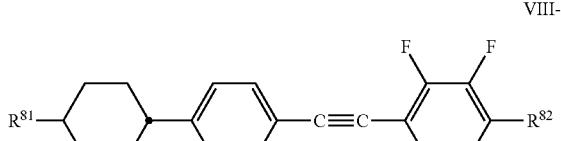
VIII-3 in which
one of
Y$^{81}$ and Y$^{82}$ denotes H and the other denotes H or F, and
R$^{81}$ has the meaning indicated above and preferably denotes
  C$_n$H$_{2n+1}$ or CH$_2$=CH—(CH$_2$)$_z$, and
R$^{82}$ has the meaning indicated above and preferably denotes
  C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$) and ($C_nH_{2n+1}$ and O—$C_mH_{2m+1}$), particularly preferably ($C_nH_{2n+1}$ and $C_mH_{2m+1}$).

The compounds of the formula VIII-1 are preferably selected from the group of the compounds of the formulae VIII-1a to VIII-1c:

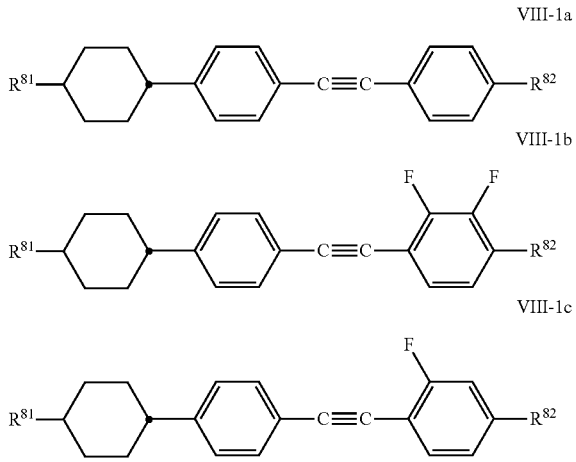

VIII-1a

VIII-1b

VIII-1c in which $R^{81}$ has the meaning indicated above and preferably denotes $C_nH_{2n+1}$ or $CH_2$=CH—$(CH_2)_Z$, and $R^{82}$ has the meaning indicated above and preferably denotes $C_mH_{2m+1}$ or O—$C_mH_{2m+1}$ or $(CH_2)_Z$—CH=$CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$) and ($C_nH_{2n+1}$ and O—$C_mH_{2m+1}$), particularly preferably ($C_nH_{2n+1}$ and $C_mH_{2m+1}$).

The compounds of the formula VIII-2 are preferably compounds of the formula VIII-2a:

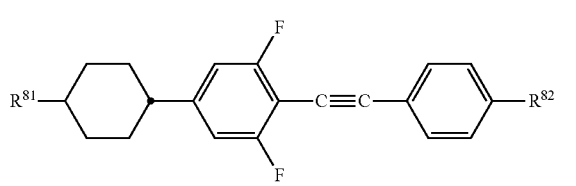

VIII-2a in which $R^{81}$ has the meaning indicated above and preferably denotes $C_nH_{2n+1}$ or $CH_2$=CH—$(CH_2)_Z$, and $R^{82}$ has the meaning indicated above and preferably denotes $C_mH_{2m+1}$ or O—$C_mH_{2m+1}$ or $(CH_2)_Z$—CH=$CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$), ($C_nH_{2n+1}$ and O—$C_mH_{2m+1}$) and ($CH_2$=CH—$(CH_2)_Z$ and $C_mH_{2m+1}$), particularly preferably ($C_nH_{2n+1}$ and $C_mH_{2m+1}$).

The compounds of the formula VIII-3 are preferably compounds of the formula VIII-3a:

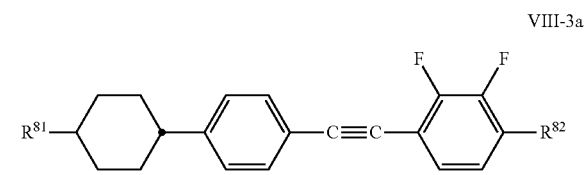

VIII-3a in which $R^{81}$ has the meaning indicated above and preferably denotes $C_nH_{2n+1}$ or $CH_2$=CH—$(CH_2)_Z$, and $R^{82}$ has the meaning indicated above and preferably denotes $C_mH_{2m+1}$ or O—$C_mH_{2m+1}$ or $(CH_2)_Z$—CH=$CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$) and ($C_nH_{2n+1}$ and O—$C_mH_{2m+1}$).

The compounds of the formula IX are preferably selected from the group of the compounds of the formulae IX-1 to IX-3:

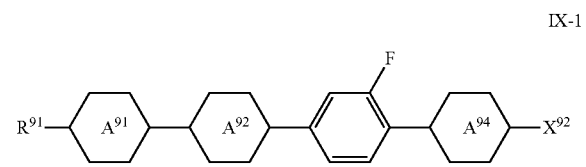

IX-1

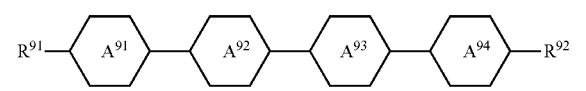

IX-2

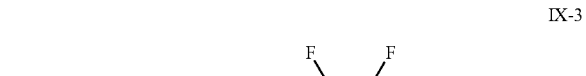

IX-3 in which the parameters have the respective meaning indicated above under formula IX and preferably one of

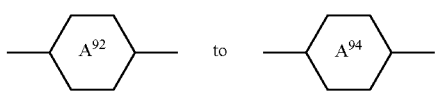

denotes

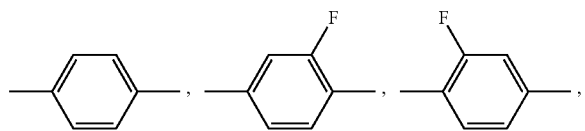

and
in which
R$^{91}$ has the meaning indicated above and preferably denotes C$_n$H$_{2n+1}$ or CH$_2$=CH—(CH$_2$)$_z$, and
R$^{92}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{91}$ and R$^{92}$) here are, in particular, (C$_n$H$_{2n+1}$ and C$_m$H$_{2m+1}$) and (C$_n$H$_{2n+1}$ and O—C$_m$H$_{2m+1}$).

The compounds of the formula IX-1 are preferably selected from the group of the compounds of the formulae IX-1a to IX-1e:

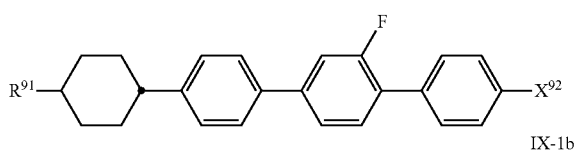

IX-1a

IX-1b

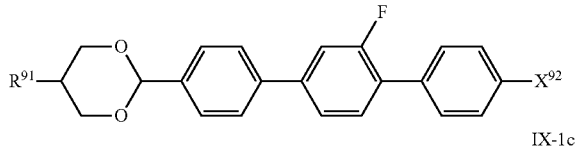

IX-1c

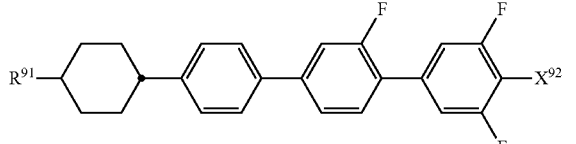

IX-1d

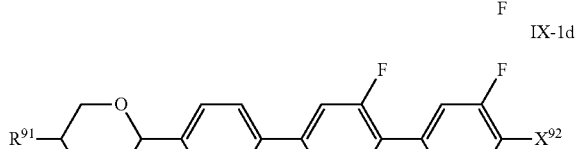

IX-1e

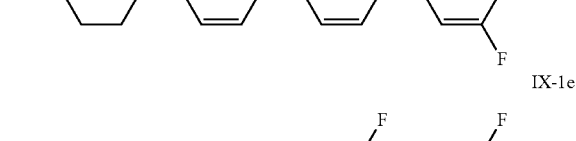

in which the parameters have the meaning given above and preferably
R$^{91}$ has the meaning indicated above and preferably denotes C$_n$H$_{2n+1}$, and n denotes an integer in the range from 0 to 15, preferably in the range from 1 to 7 and particularly preferably 1 to 5, and
X$^{92}$ preferably denotes F or Cl.

The compounds of the formula IX-2 are preferably selected from the group of the compounds of the formulae IX-2a and IX-2b:

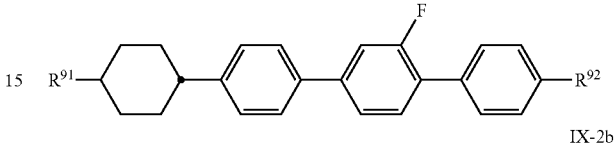

in which
R$^{91}$ has the meaning indicated above and preferably denotes C$_n$H$_{2n+1}$ or CH$_2$=CH—(CH$_2$)$_z$, and
R$^{92}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combination of (R$^{91}$ and R$^{92}$) here is, in particular, (C$_n$H$_{2n+1}$ and C$_m$H$_{2m+1}$).

The compounds of the formula IX-3 are preferably compounds of the formulae IX-3a and IX-3b:

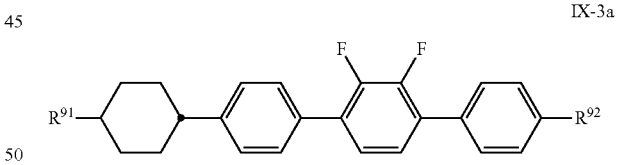

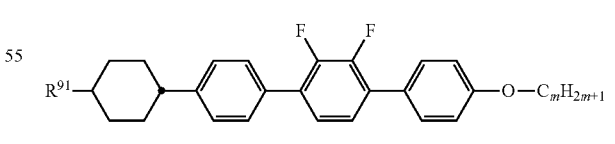

in which
R$^{91}$ has the meaning indicated above and preferably denotes C$_n$H$_{2n+1}$ or CH$_2$=CH—(CH$_2$)$_z$, and
R$^{92}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{91}$ and $R^{92}$) here are, in particular, ($C_nH_{2n+1}$ and $C_mH_{2m+1}$) and ($C_nH_{2n+1}$ and O—$C_mH_{2m+1}$), particularly preferably ($C_nH_{2n+1}$ and O—$C_mH_{2m+1}$).

In a preferred embodiment the liquid crystal medium according to the invention comprises one or more chiral compounds.

In a preferred embodiment the liquid crystal medium according to the invention comprises one or more chiral compounds selected from the group of compounds of formulae A-I to A-III:

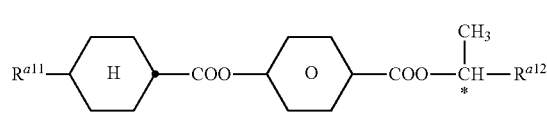

A-I

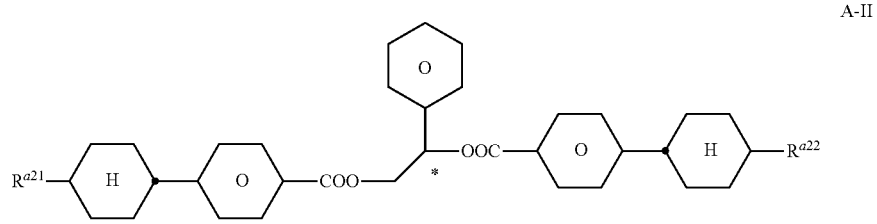

A-II

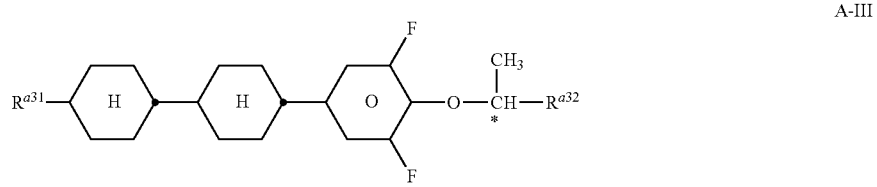

A-III in which $R^{a11}$ and $R^{a12}$, independently of one another, are alkyl, oxaalkyl or alkenyl having from 2 to 9, preferably up to 7, carbon atoms, and $R^{a11}$ is alternatively methyl or alkoxy having from 1 to 9 carbon atoms, preferably both are alkyl, preferably n-alkyl, $R^{a21}$ and $R^{a22}$, independently of one another, are alkyl or alkoxy having from 1 to 9, preferably up to 7, carbon atoms, oxaalkyl, alkenyl or alkenyloxy having from 2 to 9, preferably up to 7, carbon atoms, preferably both are alkyl, preferably n-alkyl, $R^{a31}$ and $R^{a32}$, independently of one another, are alkyl, oxaalkyl or alkenyl having from 2 to 9, preferably up to 7, carbon atoms, and $R^{a11}$ is alternatively methyl or alkoxy having from 1 to 9 carbon atoms, preferably both are alkyl, preferably n-alkyl.

Particular preference is given to dopants selected from the group consisting of the compounds of the following formulae:

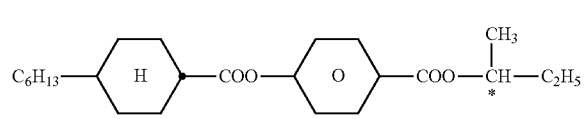

A-I-1

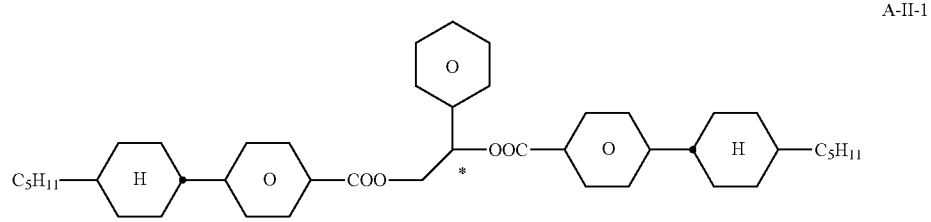

A-II-1

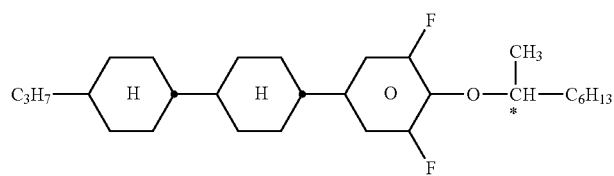
Further preferred chiral compounds are derivatives of the isosorbide, isomannitol or isoiditol of the following formula A-IV:
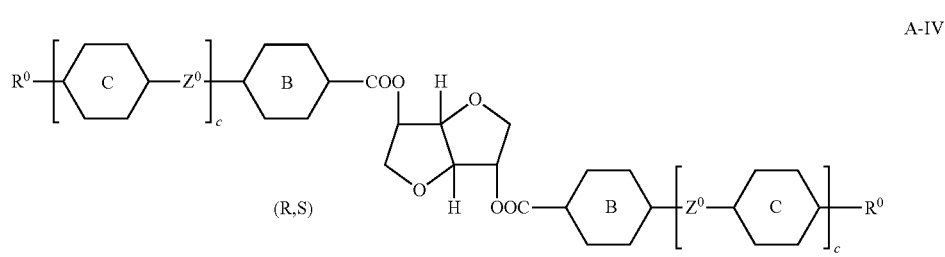
in which the group is
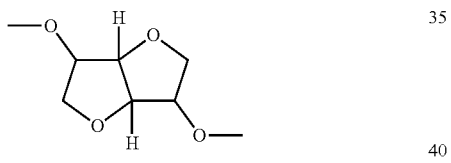
is
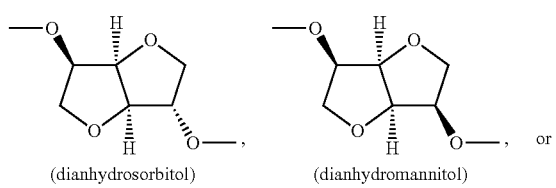
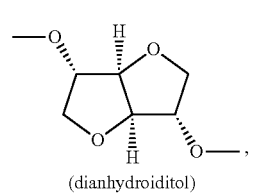
preferably dianhydrosorbitol, and chiral ethanediol derivatives, such as, for example, diphenylethanediol (hydrobenzoin), in particular mesogenic hydrobenzoin derivatives of the following formula A-V:
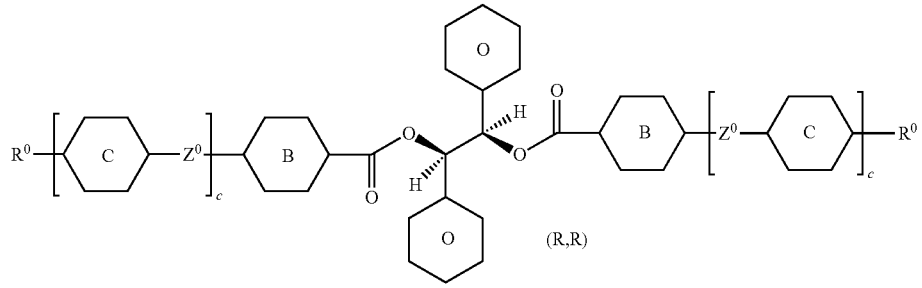

including the (R,S), (S,R), (R,R) and (S,S) enantiomers, which are not shown,
in which

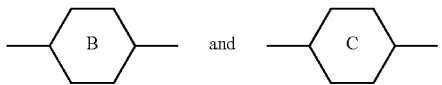

are each, independently of one another, 1,4-phenylene, which may also be mono-, di- or trisubstituted by L, or 1,4-cyclo hexylene,
L is H, F, Cl, CN or optionally halogenated alkyl, alkoxy, alkylcarbonyl, alkoxycarbonyl or alkoxycarbonyloxy having 1-7 carbon atoms,
c is 0 or 1,
$Z^0$ is —COO—, —OCO—, —$CH_2CH_2$— or a single bond, and
$R^0$ is alkyl, alkoxy, alkylcarbonyl, alkoxycarbonyl or alkylcarbonyloxy having 1-12 carbon atoms.

The compounds of the formula A-IV are described in WO 98/00428. The compounds of the formula A-V are described in GB-A-2,328,207.

Very particularly preferred dopants are chiral binaphthyl derivatives, as described in WO 02/94805, chiral binaphthol acetal derivatives, as described in WO 02/34739, chiral TADDOL derivatives, as described in WO 02/06265, and chiral dopants having at least one fluorinated bridging group and a terminal or central chiral group, as described in WO 02/06196 and WO 02/06195.

Particular preference is given to chiral compounds of the formula A-VI

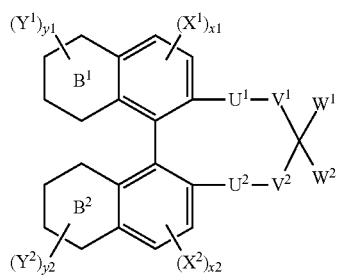

A-VI in which
$X^1$, $X^2$, $Y^1$ and $Y^2$ are each, independently of one another, F, Cl, Br, I, CN, SCN, $SF_5$, straight-chain or branched alkyl having from 1 to 25 carbon atoms, which may be monosubstituted or polysubstituted by F, Cl, Br, I or CN and in which, in addition, one or more non-adjacent $CH_2$ groups may each, independently of one another, be replaced by —O—, —S—, —NH—, $NR^0$—, —CO—, —COO—, —OCO—, —OCOO—, —S—CO—, —CO—S—, —CH=CH— or —C≡C— in such a way that O and/or S atoms are not bonded directly to one another, a polymerisable group or cycloalkyl or aryl having up to 20 carbon atoms, which may optionally be monosubstituted or polysubstituted by halogen, preferably F, or by a polymerisable group,
$x^1$ and $x^2$ are each, independently of one another, 0, 1 or 2,
$y^1$ and $y^2$ are each, independently of one another, 0, 1, 2, 3 or 4,
$B^1$ and $B^2$ are each, independently of one another, an aromatic or partially or fully saturated aliphatic six-membered ring in which one or more CH groups may be replaced by N atoms and one or more non-adjacent $CH_2$ groups may be replaced by 0 and/or S,
$W^1$ and $W^2$ are each, independently of one another, —$Z^1$-$A^1$-$(Z^2$-$A^2)_m$-R, and one of the two is alternatively $R^1$ or $A^3$, but both are not simultaneously H, or

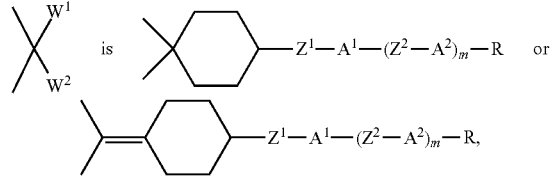

$U^1$ and $U^2$ are each, independently of one another, $CH_2$, O, S, CO or CS,
$V^1$ and $V^2$ are each, independently of one another, $(CH_2)_n$, in which from one to four non-adjacent $CH_2$ groups may be replaced by O and/or S, and one of $V^1$ and $V^2$ and, in the case where

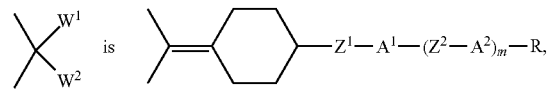

both are a single bond,
$Z^1$ and $Z^2$ are each, independently of one another, —O—, —S—, —CO—, —COO—, —OCO—, —O—COO—, —CO—$NR^0$—, —$NR^0$—CO—, —O—$CH_2$—, —$CH_2$—O—, —S—$CH_2$—, —$CH_2$—S—, —$CF_2$—O—, —O—$CF_2$—, —$CF_2$—S—, —S—$CF_2$—, —$CH_2$—$CH_2$—, —$CF_2$—$CH_2$—, —$CH_2$—$CF_2$—, —$CF_2$—$CF_2$—, —CH=N—, —N=CH—, —N=N—, —CH=CH—, —CF=CH—, —CH=CF—, —CF=CF—, —C≡C—, a combination of two of these groups, where no two O and/or S and/or N atoms are bonded directly to one another, preferably —CH=CH—COO—, or —COO—CH=CH—, or a single bond,
$A^1$, $A^2$ and $A^3$ are each, independently of one another, 1,4-phenylene, in which one or two non-adjacent CH groups may be replaced by N, 1,4-cyclohexylene, in which one or two non-adjacent $CH_2$ groups may be replaced by O and/or S, 1,3-dioxolane-4,5-diyl, 1,4-cyclohexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, where each of these groups may be monosubstituted or polysubstituted by L, and in addition $A^1$ is a single bond,
L is a halogen atom, preferably F, CN, $NO_2$, alkyl, alkoxy, alkylcarbonyl, alkoxycarbonyl or alkoxycarbonyloxy having 1-7 carbon atoms, in which one or more H atoms may be replaced by F or Cl,
m is in each case, independently, 0, 1, 2 or 3, and
R and $R^1$ are each, independently of one another, H, F, Cl, Br, I, CN, SCN, $SF_5$, straight-chain or branched alkyl having from 1 or 3 to 25 carbon atoms respectively, which may optionally be monosubstituted or polysubstituted by F, Cl, Br, I or CN, and in which one or more non-adjacent $CH_2$ groups may be replaced by —O—, —S—, —NH—, —$NR^0$—, —CO—, —COO—, —OCO—, —O—COOO—, —S—CO—, —CO—S—, —CH=CH— or —C≡C—, where no two O and/or S atoms are bonded directly to one another, or a polymerisable group.

Particular preference is given to chiral binaphthyl derivatives of the formula A-VI-1

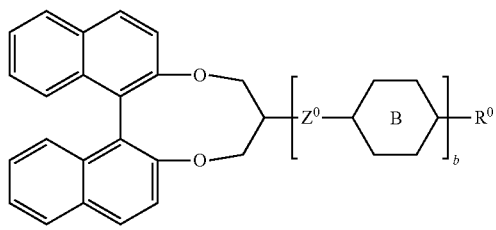

A-VI-1 in particular those selected from the following formulae A-VI-1a to A-VI-1c:

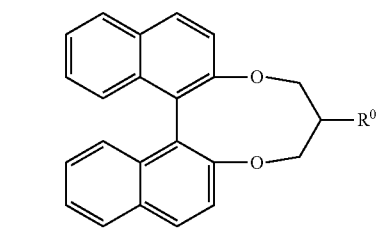

A-VI-1a

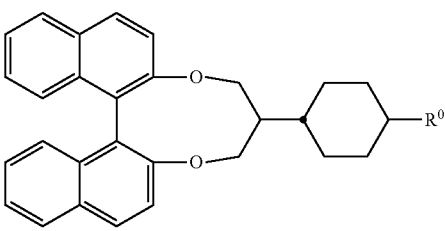

A-VI-1b

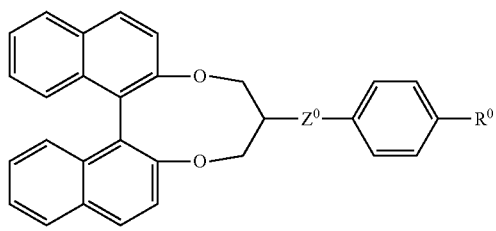

A-VI-1c in which ring B and Z° are as defined for the formula A-IV, and

R⁰ as defined for formula A-IV or H or alkyl having from 1 to 4 carbon atoms, and b is 0, 1 or 2, and Z° is, in particular, —OCO— or a single bond.

Particular p reference is furthermore given to chiral binaphthyl derivatives of the formula A-VI-2

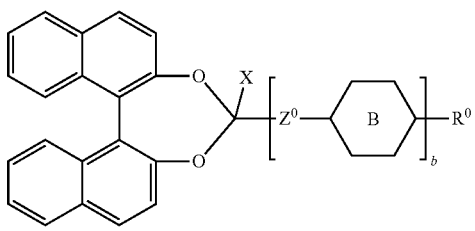

A-VI-2 in particular those selected from the following formulae A-VI-2a to A-VI-2f:

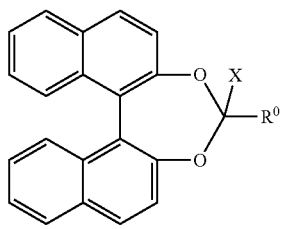

A-VI-2a

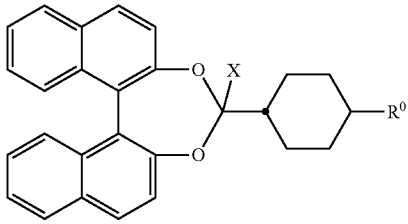

A-VI-2b

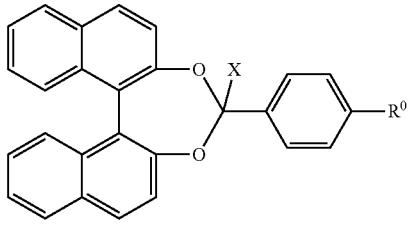

A-VI-2c

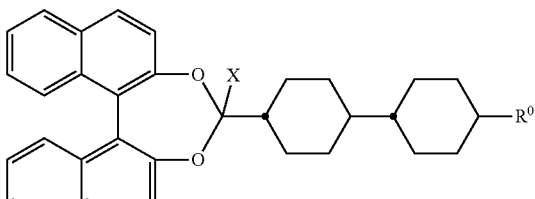

A-VI-2d

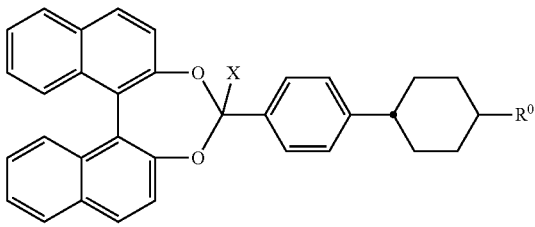

A-VI-2e

A-VI-2f

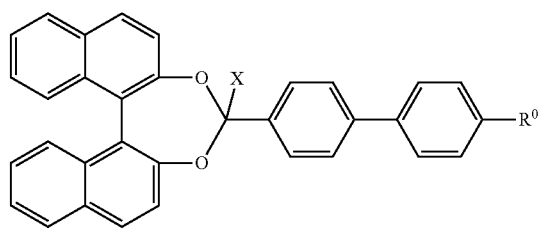

in which R⁰ is as defined for the formula A-VI, and X is H, F, Cl, CN or R⁰, preferably F.

The compounds of the formula DFS can be prepared analogously to processes known to the person skilled in the art and described in standard works of organic chemistry, such as, for example, Houben-Weyl, Methoden der organischen Chemie [Methods of Organic Chemistry], Thieme Verlag, Stuttgart. For specific processes for the preparation of compounds of the formula DFS, reference is furthermore made to the known literature and to the working examples.

The starting materials for the synthesis of compounds of formula DFS are commercially available or can be synthesised according to known procedures. Preferably, compounds of formula DFS are synthesised analogously to the procedures disclosed in WO 2012/069133 A1 and as exemplified by the synthetic pathway of a compound of formula DFS-1-1 (formula 7) shown in scheme 1.

Scheme 1.

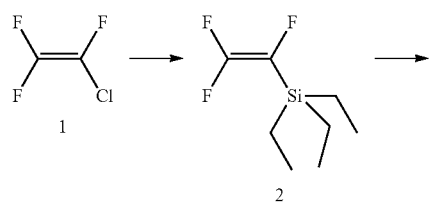

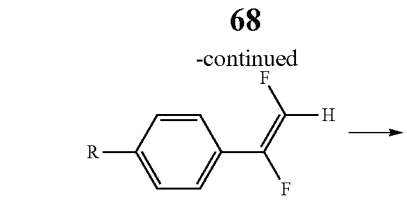

4

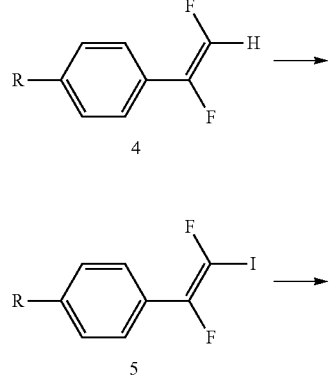

5

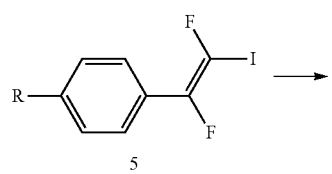

6

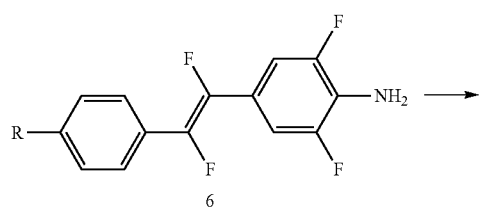

7

R = alkyl

From the known intermediates 5 the compounds according to the present invention are preferably prepared by cross coupling with for example paminobenzene boronic acids to give aminostilbenes such as compound 6. The latter can be transferred to the isothiocyanates 7 by treatment with thiophosgene, thiocarbonyldiimidazole, or the like.

The invention further related to compounds of formula DFS-2 above

DFS-2

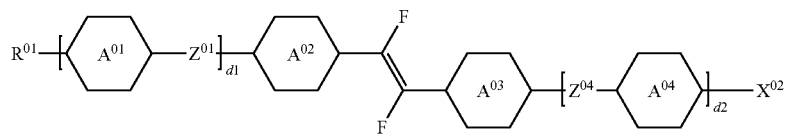

wherein
X⁰² denotes —NCS,

-continued

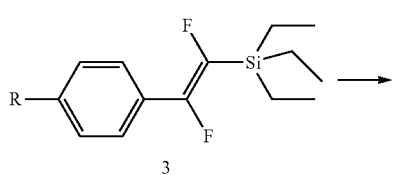

3

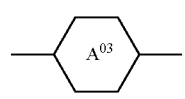

denotes

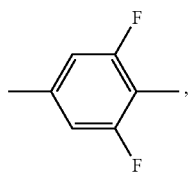

and
d2 is 0,
and the remaining groups and parameters occurring have the meaning indicated above.

The invention further relates to a process for the preparation of compounds of formula DFS-2, characterised in that the aniline precursor DFS-2A is transferred into a compound of formula DFS-2 according to the procedure given in scheme 1 above,

DFS-2A

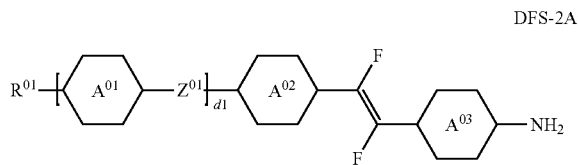

where the occurring groups and parameters have the meanings indicated above for formula DFS-2.

Preferred compounds of formula DFS-2 are the following:

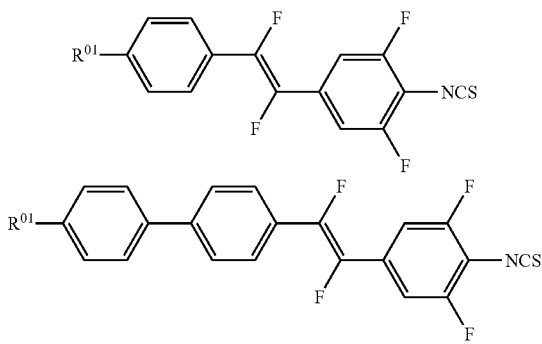

The liquid-crystal media according to the invention are eminently suitable for use in components for high-frequency technology or for the microwave region and/or millimetre wave region of the electromagnetic spectrum.

The present invention also relates to the use of the liquid-crystalline media according to the invention in electro-optical displays and in particular in components for high-frequency technology.

The invention further relates to a component for high-frequency technology, especially components for high-frequency devices, in particular antennas, especially for the gigahertz region and the terahertz region, which are operated in the microwave or millimetre wave region, containing a liquid-crystal medium according to the present invention. The invention also relates to a microwave antenna array comprising such a component. Preferred components are phase shifters, varactors, wireless and radio wave antenna arrays, matching circuit adaptive filters and others and are employed for the phase shifting of microwaves for tuneable phased-array antennas or for tuneable cells of microwave antennas based on "reflectarrays".

The invention further relates to a process for tuning a microwave antenna array wherein a component for high-frequency technology according to the invention is electrically addressed.

The liquid-crystalline media in accordance with the present invention preferably comprise 10% or less, preferably 5% or less, particularly preferably 2% or less, very particularly preferably 1% or less, and in particular absolutely no compound having only two or fewer five- and/or six-membered rings.

The definitions of the abbreviations (acronyms) used for the compounds in the present application are indicated below in Table D or are evident from Tables A to C.

According to the present invention, the liquid-crystal medium comprises one or more compounds of formula DFS.

According to preferred embodiments of the present invention, the liquid-crystalline medium comprises
one or more compounds of formula DFS-1;
one or more compounds of formulae DFS-1 and DFS-2;
one or more compounds of formulae DFS-1 and I;
one or more compounds of formulae DFS-2 and I;
one or more compounds of formulae DFS-1 and DFS-2 and I;
one or more compounds of formulae DFS-1 and DFS-2 and I and VI;
one or more compounds of formulae DFS-1 and T and I;
one or more compounds of formulae DFS-1 and T and I and VII, preferably VII-7;
one or more compounds of formulae DFS-1 and U and I and II and V;
one or more compounds of formulae DFS-2 and U and I and V;
one or more compounds of formulae DFS-1 and T and I and II;
one or more compounds of formulae DFS-1 and T and VI;
one or more compounds of formulae DFS-1 and T and I and VI.

If present in the liquid-crystalline medium according to the invention, the compounds of formula I are preferably selected from the compounds of the formulae I-1a-1 to I-1a-12, particularly preferably of the formula I-1a-2; very particularly preferably one or more compounds of the formula I-1a-2 and one or more compounds selected from the group of the compounds of the formula I-1a-1 and formulae I-1a-3 to I-1a-12, and one or more compounds of the formulae I-1 b-1 to I-1b-12 and/or I-2 and/or I-3 and/or I-4.

In a further preferred embodiment of the present invention, the liquid-crystal medium comprises one or more compounds selected from the group of the compounds of the formulae I-1 b-1 to I-1b-12, particularly preferably selected from the group of the compounds of the formulae I-1 b-5 and/or I-1 b-7 and/or I-1 b-8 and/or I-1 b-9 and/or I-1b-10, and one or more compounds selected from the group of the compounds of the formulae I-1a-1 to I-1a-12, preferably of the formula I-1a-2, and/or one or more compounds of the formulae I-2 and/or I-3 and/or I-4.

In a further preferred embodiment of the present invention the liquid-crystal medium comprises one or more compounds of the formula I-2 and one or more compounds of the formula I-1, preferably of the formula I-1a, preferably of the formulae I-1a-2, and/or I-1b, and/or one or more compounds of the formulae I-3 and/or I-4.

In a further preferred embodiment of the present invention, the liquid-crystal medium comprises one or more compounds of the formula I-3 and one or more compounds of the formula I-1, preferably of the formula I-1a, preferably of the formula I-1a-2, and/or I-1b, and/or one or more compounds of the formulae I-2 and/or I-4.

In a further preferred embodiment of the present invention, the liquid-crystal medium comprises one or more compounds of the formula I-4 and one or more compounds of the formula I-1, preferably of the formula I-1a, preferably of the formula I-1a-2, and/or I-1b, and/or one or more compounds of the formulae I-2 and/or I-3.

In a preferred embodiment of the present invention, the liquid crystal medium comprises one or more compounds of the formula V, preferably of the sub-formulae V-2, particularly preferably of the formula V-2a.

In a preferred embodiment, the liquid crystal medium comprises one or more compounds selected from the group of compounds PGP-2-3, PGP-2-4, PGP-2-5, PGP-2-2V and PGP-2-2V1.

In a preferred embodiment of the present invention, the liquid crystal medium comprises one or more compounds of the formula U, preferably selected from the group of the sub-formulae U-1a, U-2b, U-2c, U-3b, and U-3c, particularly preferably of the formula U-1a.

The liquid-crystalline media in accordance with the present invention preferably comprise, more preferably predominantly consist of, even more preferably essentially consist of and very particularly preferably completely consist of compounds selected from the group of the compounds of the formulae DFS, T, I, II, V, VI and VII, preferably of DFS, T, U, I.

In a preferred embodiment he liquid-crystalline media in according to the present invention preferably comprise, more preferably predominantly consist of, even more preferably essentially consist of and very particularly preferably completely consist of compounds selected from the group of the compounds of the formulae DFS-1 and/or DFS-2.

In a preferred embodiment, the liquid crystalline media according to the present invention comprise one or more compounds of formula DFS in a total concentration of 4% to 100%, more preferably 10% to 80%, even more preferably 20% to 70% and very preferably 30% to 60%, of the mixture as a whole.

In a preferred embodiment, the liquid crystalline media according to the present invention comprise one or more compounds of formula DFS-1 in a total concentration of 1% to 100%, more preferably 10% to 80%, even more preferably 20% to 70% and very preferably 30% to 60%, of the mixture as a whole.

In a preferred embodiment, the liquid crystalline media according to the present invention comprise one or more compounds of formula DFS-2 in a total concentration of 1% to 70%, more preferably 2% to 50%, even more preferably 3% to 40% and very preferably 10% to 20%, of the mixture as a whole.

In a preferred embodiment, the liquid crystalline media according to the present invention comprise one or more compounds of formula T in a total concentration of 5% to 70%, more preferably 10% to 60%, and very preferably 20% to 50% of the mixture as a whole.

In a preferred embodiment, the liquid crystalline media according to the present invention comprise one or more compounds of formula I in a total concentration of 10% to 80%, more preferably 20% to 70%, even more preferably 30% to 60% and very preferably 40% to 50%, of the mixture as a whole.

In this application, "comprise" in the context of compositions means that the medium comprises the compound or compounds indicated, preferably in a total concentration of 10% or more and very preferably 20% or more.

In this context, "predominantly consist of" means that the medium comprises 55% or more, preferably 60% or more and very preferably 70% or more, of the compound or compounds indicated.

In this context, "essentially consist of" means that the medium comprises 80% or more, preferably 90% or more and very preferably 95% or more, of the compound or compounds indicated.

In this context, "completely consist of" means that the medium comprises 98% or more, preferably 99% or more and very preferably 100.0% of the compound or compounds indicated.

Other mesogenic compounds which are not explicitly mentioned above can optionally and advantageously also be used in the media in accordance with the present invention. Such compounds are known to the person skilled in the art.

The liquid-crystal media in accordance with the present invention preferably have a clearing point of 90° C. or more, more preferably 100° C. or more, even more preferably 120° C. or more, particularly preferably 150° C. or more and very particularly preferably 170° C. or more.

The liquid-crystal media in accordance with the present invention preferably have a clearing point of 160° C. or less, more preferably 140° C. or less, particularly preferably 120° C. or less, and very particularly preferably 100° C. or less.

The nematic phase of the media according to the invention preferably extends at least from 0° C. or less to 90° C. or more. It is advantageous for the media according to the invention to exhibit even broader nematic phase ranges, preferably at least from −10° C. or less to 120° C. or more, very preferably at least from −20° C. or less to 140° C. or more and in particular at least from −30° C. or less to 150° C. or more, very particularly preferably at least from −40° C. or less to 170° C. or more.

The expression "to have a nematic phase" here means on the one hand that no smectic phase and no crystallisation are observed at low temperatures at the corresponding temperature and on the other hand that no clearing occurs on heating from the nematic phase. The investigation at low temperatures is carried out in a flow viscometer at the corresponding temperature and checked by storage in test cells having a layer thickness of 5 μm for at least 100 hours. At high temperatures, the clearing point is measured in capillaries by conventional methods.

In a preferred embodiment of the present invention, the liquid-crystal media employed have positive dielectric anisotropy ($\Delta\varepsilon$). The $\Delta\varepsilon$ of the liquid-crystal medium in accordance with the invention, at 1 kHz and 20° C., is preferably 1 or more, more preferably 2 or more and very preferably 5 or more.

In a preferred embodiment, the $\Delta\varepsilon$ is 1.8 or more and 15.0 or less, more preferably between 2.0 or more and 12.0 or less, particularly preferably between 3.0 or more and 11.0 or less and very particularly preferably between 3.5 or more and 10.0 or less.

The $\Delta n$ of the liquid-crystal media in accordance with the present invention, at 589 nm ($Na^D$) and 20° C., is preferably in the range from 0.200 or more to 0.90 or less, more preferably in the range from 0.250 or more to 0.90 or less, even more preferably in the range from 0.300 or more to 0.85 or less and very particularly preferably in the range from 0.350 or more to 0.800 or less.

The $\Delta n$ of the liquid-crystal media in accordance with the present invention, at 589 nm ($Na^D$) and 20° C., is preferably 0.350 or less, more preferably 0.300 or less, even more preferably 0.250 or less and particularly preferably 0.200 or less.

The Δn of the liquid-crystal media in accordance with the present invention, at 589 nm (Na$^D$) and 20° C., is preferably 0.900 or more, more preferably 0.850 or more, and particularly preferably 0.800 or more.

Furthermore, the liquid-crystal media according to the invention are characterised by high anisotropy values in the microwave range. The birefringence at about 8.3 GHz is, for example, preferably 0.14 or more, particularly preferably 0.15 or more, particularly preferably 0.20 or more, particularly preferably 0.25 or more and very particularly preferably 0.30 or more. In addition, the birefringence is preferably 0.80 or less.

In the present application, the expression dielectrically positive describes compounds where Δε>3.0, dielectrically neutral describes those where −1.5≤Δε≤3.0 and dielectrically negative describes those where Δε<−1.5. Δε is determined at a frequency of 1 kHz and at 20° C. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 μm. The voltage applied is a rectangular wave having a frequency of 1 kHz and an effective value of typically 0.5 V to 1.0 V, but it is always selected to be below the capacitive threshold of the respective test mixture.

The host mixture used for dielectrically positive compounds is mixture ZLI-4792 and that used for dielectrically neutral and dielectrically negative compounds is mixture ZLI-3086, both from Merck KGaA, Germany. The absolute values of the dielectric constants of the compounds are determined from the change in the respective values of the host mixture on addition of the compounds of interest. The values are extrapolated to a concentration of the compounds of interest of 100%.

The expression threshold voltage in the present application refers to the optical threshold and is quoted for 10% relative contrast ($V_{10}$), and the expression saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees. All physical properties are determined in accordance with "Merck Liquid Crystals, Physical Properties of Liquid Crystals", Status November 1997, Merck KGaA, Germany, and are quoted for a temperature of ° C., unless expressly stated otherwise. The optical anisotropy (Δn) is determined at a wavelength of 589.3 nm. The dielectric anisotropy (Δε) is determined at a frequency of 1 kHz, unless expressly stated otherwise. The threshold voltages, as well as all other electro-optical properties, are determined using test cells produced at Merck KGaA, Germany. The test cells for the determination of Δε have a cell thickness of approximately 20 μm. The electrode is a circular ITO electrode having an area of 1.13 cm$^2$ and a guard ring. The orientation layers are SE-1211 from Nissan Chemicals, Japan, for homeotropic orientation ($\varepsilon_\parallel$) and polyimide AL-1054 from Japan Synthetic Rubber, Japan, for homogeneous orientation ($\varepsilon_\perp$). The capacitances are determined using a Solatron 1260 frequency response analyser using a sine wave with a voltage of 0.3 $V_{rms}$.

Where experimental values are not available this is indicated by the abbreviation "N/A".

All temperatures, such as, for example, the melting point $T_{(C,N)}$ or $T_{(C,S)}$, the transition from the smectic (S) to the nematic (N) phase $T_{(S,N)}$ and the clearing point $T_{(N,I)}$ of the liquid crystals, are quoted in degrees Celsius. All temperature differences are quoted in differential degrees.

In case data are not available this is indicated by the abbreviation "N/A".

The light used in the electro-optical measurements is white light. A set-up using a commercially available DMS instrument from Autronic-Melchers, Germany, is used here. The characteristic voltages have been determined under perpendicular observation. The threshold ($V_{10}$), mid-grey ($V_{50}$) and saturation ($V_{90}$) voltages have been determined for 10%, 50% and 90% relative contrast, respectively.

The liquid-crystalline media are investigated with respect to their properties in the microwave frequency region as described in A. Penirschke et al., "Cavity Perturbation Method for Characterisation of Liquid Crystals up to 35 GHz", 34$^{th}$ European Microwave Conference—Amsterdam, pp. 545-548. Compare in this respect also A. Gaebler et al., "Direct Simulation of Material Permittivites . . . ", 12MTC 2009—International Instrumentation and Measurement Technology Conference, Singapore, 2009 (IEEE), pp. 463-467, and DE 10 2004 029 429 A, in which a measurement method is likewise described in detail.

The liquid crystal is introduced into a cylindrical polytetrafluoroethylene (PTFE) or quartz capillary. The capillary has an internal radius of 180 μm and an external radius of 350 μm. The effective length is 2.0 cm. The filled capillary is introduced into the centre of the cylindrical cavity with a resonance frequency of 19 GHz. This cavity has a length of 11.5 mm and a radius of 6 mm. The input signal (source) is then applied, and the result of the output signal is recorded using a commercial vector network analyser. For other frequencies, the dimensions of the cavity are adapted correspondingly.

The change in the resonance frequency and the Q factor between the measurement with the capillary filled with the liquid crystal and the measurement without the capillary filled with the liquid crystal is used to determine the dielectric constant and the loss angle at the corresponding target frequency by means of equations 10 and 11 of the above-mentioned publication A. Penirschke et al., "Cavity Perturbation Method for Characterisation of Liquid Crystals up to 35 GHz", 34$^{th}$ European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla. The alignment of the magnet is set correspondingly and then rotated correspondingly through 90°.

Preferred components are phase shifters, varactors, wireless and radio wave antenna arrays, matching circuit adaptive filters and others.

In the present application, the term compounds is taken to mean both one compound and a plurality of compounds, unless expressly stated otherwise.

The dielectric anisotropy in the microwave region is defined as $$\Delta\varepsilon_r \equiv (\varepsilon_{r,\parallel} - \varepsilon_{r,\perp}), \text{ while } \varepsilon_{ave.} \text{ is } (\varepsilon_\parallel + 2\varepsilon_\perp)/3.$$

The tunability (τ) is defined as $$\tau \equiv (\Delta\varepsilon_r / \varepsilon_{r,\parallel}).$$

The material quality (η) is defined as $$\eta \equiv (\tau / \tan \delta_{\varepsilon r,max}), \text{ where}$$

the maximum dielectric loss is $$\tan \delta_{\varepsilon r,max.} = \max \cdot \{\tan \delta_{\varepsilon r,\perp}; \tan \delta_{\varepsilon r,\parallel}\}.$$

The material quality (η) of the preferred liquid-crystal materials is 6 or more, preferably 8 or more, preferably 10 or more, preferably 15 or more, preferably 17 or more, preferably 20 or more, particularly preferably 25 or more, very particularly preferably 30 and in particular 40 or more or even 50 or more.

The FIGURE of Merit (FoM) η(μ-waves)/tan(δ) of the preferred liquid-crystal materials is 5 or more, preferably 10 or more, and particularly preferably 20 or more.

In the corresponding components, the preferred liquid-crystal materials have phase shifter qualities of 15°/dB or more, preferably 20°/dB or more, preferably 30°/dB or more, preferably 40°/dB or more, preferably 50°/dB or more, particularly preferably 80°/dB or more and very particularly preferably 100°/dB or more.

In some embodiments, however, it is also possible to use liquid crystals having a negative value of the dielectric anisotropy.

The liquid crystals employed are either individual substances or mixtures. They preferably have a nematic phase.

The term "alkyl" preferably encompasses straight-chain and branched alkyl groups, as well as cycloalkyl groups, each having 1 to 15 carbon atoms, in particular the straight-chain groups methyl, ethyl, propyl, butyl, pentyl, hexyl and heptyl, as well as cyclopropyl and cyclohexyl. Groups having 2 to 10 carbon atoms are generally preferred.

The term "alkenyl" preferably encompasses straight-chain and branched alkenyl groups having 2 to 15 carbon atoms, in particular the straight-chain groups. Particularly preferred alkenyl groups are $C_2$- to $C_7$-1E-alkenyl, $C_4$- to $C_7$-3E-alkenyl, $C_5$- to $C_7$-4-alkenyl, $C_6$- to $C_7$-5-alkenyl and $C_7$-6-alkenyl, in particular $C_2$- to $C_7$-1E-alkenyl, $C_4$- to $C_7$-3E-alkenyl and $C_5$- to $C_7$-4-alkenyl. Examples of further preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably encompasses straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" or "alkoxyalkyl" preferably encompasses straight-chain radicals of the formula $C_nH_{2n+1}$—O—$(CH_2)_m$, in which n and m each, independently of one another, denote an integer from 1 to 10. Preferably, n here is 1 and m is 1 to 6.

Compounds containing a vinyl end group and compounds containing a methyl end group have low rotational viscosity.

In the present application, both high-frequency technology and hyper-frequency technology denote applications having frequencies in the range from 1 MHz to 100 THz, preferably from 1 GHz to 30 THz, more preferably 2 GHz to 10 THz, particularly preferably from about 5 GHz to 5 THz.

The liquid-crystal media in accordance with the present invention may comprise further additives and chiral dopants in the usual concentrations. The total concentration of these further constituents is in the range from 0% to 10%, preferably 0.1% to 6%, based on the mixture as a whole. The concentrations of the individual compounds used are each preferably in the range from 0.1% to 3%. The concentration of these and similar additives is not taken into consideration when quoting the values and concentration ranges of the liquid-crystal compounds of the liquid-crystal media in this application.

The liquid-crystal media according to the invention consist of a plurality of compounds, preferably 3 to 30, more preferably 4 to 20 and very preferably 4 to 15 compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called premixes, which can be, for example, homologous or eutectic mixtures of compounds, or using so-called "multibottle" systems, the constituents of which are themselves ready-to-use mixtures. Hence, the invention relates to a Process for the preparation of a liquid-crystal medium where one or more compounds of formula DFS are mixed with one or more further compounds and/or with one or more additives.

In the present invention and especially in the following examples, the structures of the mesogenic compounds are indicated by means of abbreviations, also referred to as acronyms. In these acronyms, the chemical formulae are abbreviated as follows using Tables A to C below. All groups $C_nH_{2n+1}$, $C_mH_{2m+1}$ and $C_lH_{2l+1}$ or $C_nH_{2l+1}$, $C_mH_{2m-1}$ and $C_lH_{2l-1}$ denote straight-chain alkyl or alkenyl, preferably 1E-alkenyl, having n, m and l C atoms respectively, where n, m and l, independently of one another, denote an integer from 1 to 9, preferably 1 to 7, or from 2 to 9, preferably 2 to 7, respectively. $C_oH_{2o+1}$ denotes straight-chain alkyl having 1 to 7, preferably 1 to 4, C atoms, or branched alkyl having 1 to 7, preferably 1 to 4, C atoms.

Table A lists the codes used for the ring elements of the core structures of the compounds, while Table C shows the linking groups. Table C gives the meanings of the codes for the left-hand or right-hand end groups. Table D shows illustrative structures of compounds with their respective abbreviations.

TABLE A

Ring elements

C

TABLE A-continued
| Ring elements | |
|---|---|
| 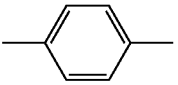 | P |
| 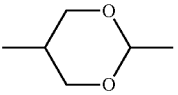 | D |
| 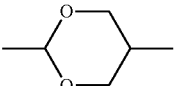 | DI |
| 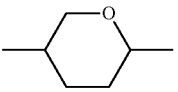 | A |
| 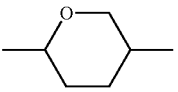 | AI |
| 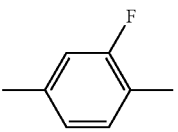 | G |
| 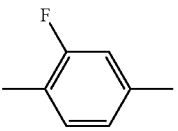 | GI |
| 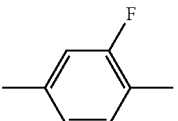 | U |
| 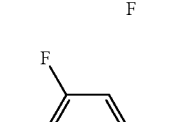 | UI |
| 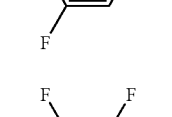 | Y |
| 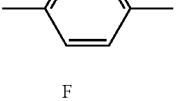 | fX |
| 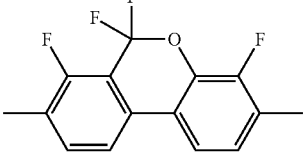 | fXI |
| | M |
| | MI |
| | N |
| | NI |
| | fN |
| | fNI |
| | dH |
| | Np |
| | iNp |
| | N3f |

TABLE A-continued

| Ring elements | |
|---|---|
| (fluorinated naphthalene with F, F, F substituents) | N3fI |
| (tetrahydronaphthalene) | tH |
| (tetrahydronaphthalene isomer) | tHI |
| (difluoro tetrahydronaphthalene) | tH2f |
| (difluoro tetrahydronaphthalene isomer) | tH2fI |
| (fluorinated indane) | K |
| (fluorinated indane isomer) | KI |
| (cyclohexadiene) | L |
| (cyclohexene) | LI |
| (fluoro cyclohexene) | F |
| (fluoro cyclohexene isomer) | FI |

TABLE A-continued

| Ring elements | |
|---|---|
| $C_oH_{2o+1}$ on dimethylbenzene | P(o) |
| $C_oH_{o+1}$ on dimethylbenzene | PI(o) |
| isopropyl dimethylbenzene | P(i3) |
| isopropyl dimethylbenzene isomer | PI(c3) |
| tert-butyl dimethylbenzene | P(t4) |
| tert-butyl dimethylbenzene isomer | PI(t4) |
| cyclopropyl dimethylbenzene | P(c3) |
| cyclopropyl dimethylbenzene isomer | PI(c3) |
| cyclobutyl dimethylbenzene | P(c4) |

TABLE A-continued

| Ring elements | |
|---|---|
| [cyclobutyl-phenyl structure] | PI(c4) |
| [cyclopentyl-phenyl structure] | P(c5) |
| [cyclopentyl-phenyl structure] | PI(c5) |
| [cyclopentenyl-phenyl structure] | P(e5) |
| [cyclopentenyl-phenyl structure] | PI(e5) |
| [cyclohexyl-phenyl structure] | P(c6) |
| [cyclohexyl-phenyl structure] | PI(c6) |
| [cyclohexenyl-phenyl structure] | P(e6) |
| [cyclohexenyl-phenyl structure] | PI(e6) |
| [CH₂F-phenyl structure] | P(1F) |
| [CH₂F-phenyl structure] | PI(1F) |
| [F, (CH₂)ₒH phenyl structure]<br>o ∈ {1; 2; 3; 4; 5; 6} | GI(o) |
| [H(CH₂)ₒ, F phenyl structure]<br>o ∈ {1; 2; 3; 4; 5; 6} | G(o) |
| [F, isopropyl phenyl structure] | GI(i3) |
| [isopropyl, F phenyl structure] | G(i3) |
| [F, t-butyl phenyl structure] | GI(t4) |
| [t-butyl, F phenyl structure] | G(t4) |

TABLE A-continued

Ring elements

[Structure: 2-fluoro-3-cyclopropyl benzene with methyl substituents] GI(c3)

[Structure: cyclopropyl-fluoro benzene with methyl substituents] G(c3)

[Structure: cyclobutyl-fluoro benzene] GI(c4)

[Structure: cyclobutyl-fluoro benzene] G(c4)

[Structure: cyclopentyl-fluoro benzene] GI(c5)

[Structure: cyclopentyl-fluoro benzene] G(c5)

[Structure: cyclopentenyl-fluoro benzene] GI(e5)

TABLE A-continued

Ring elements

[Structure: cyclopentenyl-fluoro benzene] G(e5)

[Structure: cyclohexyl-fluoro benzene] GI(c6)

[Structure: cyclohexyl-fluoro benzene] G(c6)

[Structure: cyclohexenyl-fluoro benzene] GI(e6)

[Structure: cyclohexenyl-fluoro benzene] G(e6)

TABLE B

| | Linking groups | | |
|---|---|---|---|
| E | —$CH_2CH_2$— | Z | —CO—O— |
| V | —CH=CH— | ZI | —O—CO— |
| X | —CF=CH— | O | —$CH_2$—O— |
| XI | —CH=CF— | OI | —O—$CH_2$— |
| Vf | —CF=CF— | Q | —$CF_2$—O— |
| T | —C≡C— | QI | —O—$CF_2$— |
| W | —$CF_2CF_2$— | | |

TABLE C

End groups

| Left-hand side | | Right-hand side | |
|---|---|---|---|
| Use alone | | | |
| -n- | $C_nH_{2n+1}$— | -n | —$C_nH_{2n+1}$ |
| -nO- | $C_nH_{2n+1}$—O— | -nO | —O—$C_nH_{2n+1}$ |

TABLE C-continued

| End groups | | | |
|---|---|---|---|
| Left-hand side | | Right-hand side | |
| -V- | $CH_2=CH-$ | -V | $-CH=CH_2$ |
| -nV- | $C_nH_{2n+1}-CH=CH-$ | -nV | $-C_nH_{2n}-CH=CH_2$ |
| -Vn- | $CH_2=CH-C_nH_{2n+1}-$ | -Vn | $-CH=CH-C_nH_{2n+1}$ |
| -nVm- | $C_nH_{2n+1}-CH=CH-C_mH_{2m}-$ | -nVm | $-C_nH_{2n}-CH=CH-C_mH_{2m+1}$ |
| -N- | $N\equiv C-$ | -N | $-C\equiv N$ |
| -S- | $S=C=N-$ | -S | $-N=C=S$ |
| -F- | $F-$ | -F | $-F$ |
| -CL- | $Cl-$ | -CL | $-Cl$ |
| -M- | $CFH_2-$ | -M | $-CFH_2$ |
| -D- | $CF_2H-$ | -D | $-CF_2H$ |
| -T- | $CF_3-$ | -T | $-CF_3$ |
| -MO- | $CFH_2O-$ | -OM | $-OCFH_2$ |
| -DO- | $CF_2HO-$ | -OD | $-OCF_2H$ |
| -TO- | $CF_3O-$ | -OT | $-OCF_3$ |
| -FXO- | $CF_2=CH-O-$ | -OXF | $-O-CH=CF_2$ |
| -A- | $H-C\equiv C-$ | -A | $-C\equiv C-H$ |
| -nA- | $C_nH_{2n+1}-C\equiv C-$ | -An | $-C\equiv C-C_nH_{2n+1}$ |
| -NA- | $N\equiv C-C\equiv C-$ | -AN | $-C\equiv C-C\equiv N$ |
| Use together with others | | | |
| -...A...- | $-C\equiv C-$ | -...A... | $-C\equiv C-$ |
| -...V...- | $-CH=CH-$ | -...V... | $-CH=CH-$ |
| -...Z...- | $-CO-O-$ | -...Z... | $-CO-O-$ |
| -...ZI...- | $-O-CO-$ | -...ZI... | $-O-CO-$ |
| -...K...- | $-CO-$ | -...K... | $-CO-$ |
| -...W...- | $-CF=CF-$ | -...W... | $-CF=CF-$ | in which n and m each denote integers, and the three dots "..." are placeholders for other abbreviations from this table.

The following table shows illustrative structures together with their respective abbreviations. These are shown in order to illustrate the meaning of the rules for the abbreviations. They furthermore represent compounds which are preferably used.

TABLE D

Illustrative structures

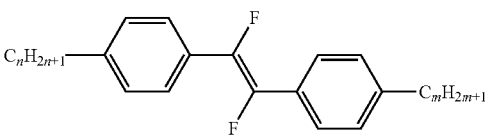

PVfP-n-m

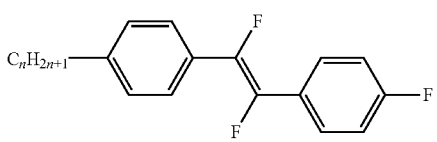

PVfP-n-F

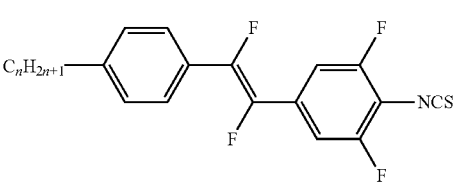

PVfU-n-S

TABLE D-continued
Illustrative structures
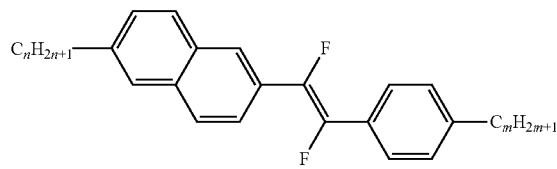
NpVfP-n-m
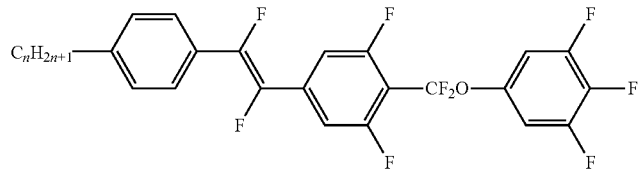
PVfUQU-n-F
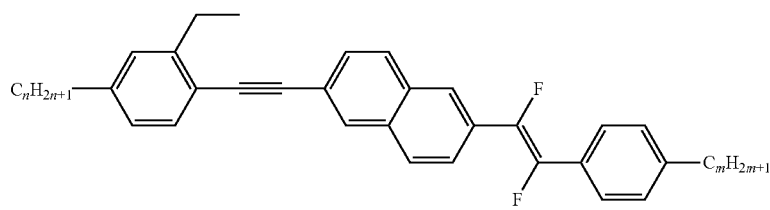
P(2)TNpVfP-n-m
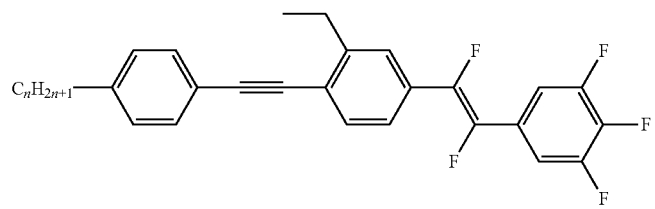
PTPI(2)VfU-n-F
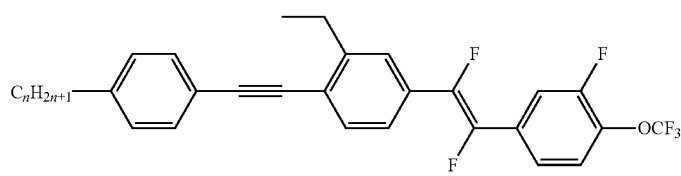
PTPI(2)VfG-n-OT
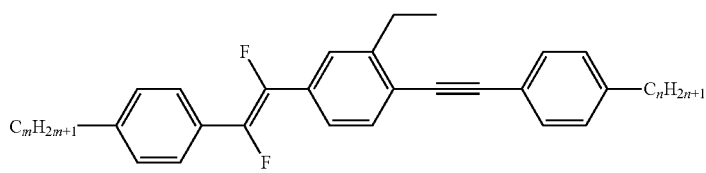
PVfP(2)TP-n-m
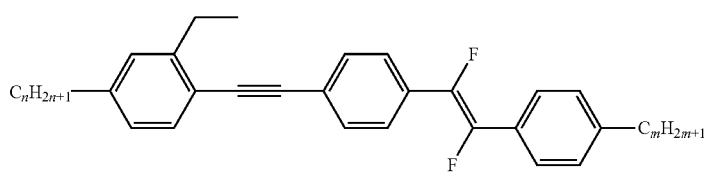
P(2)TPVfP-n-m TABLE D-continued
Illustrative structures
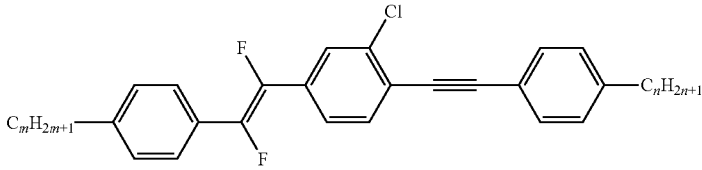
PVfP(Cl)TP-n-m
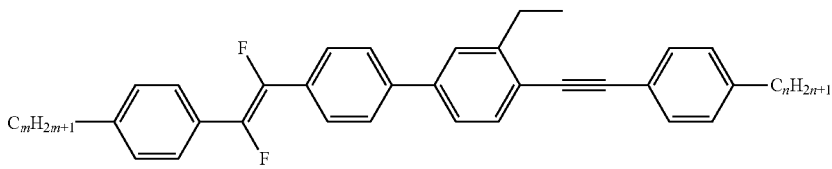
PVfPP(2)TP-n-m
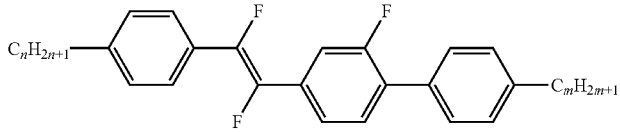
PVfGP-n-m
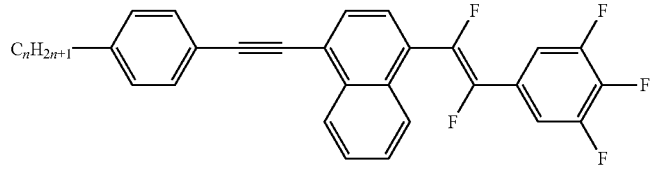
PTiNpVfU-n-F
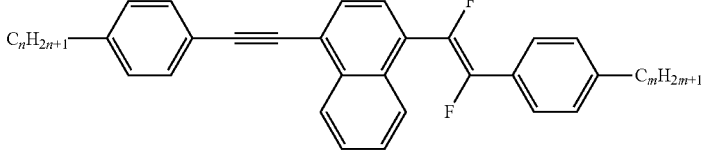
PTiNpVfP-n-m
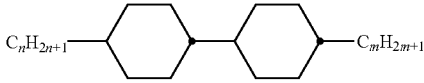
CC-n-m
CC-n-Om
CC-n-V TABLE D-continued
Illustrative structures
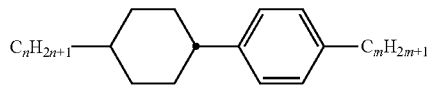
CP-n-m
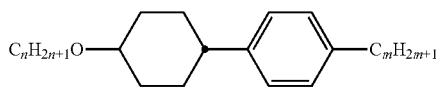
CP-nO-m
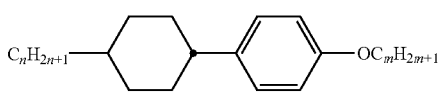
CP-n-Om
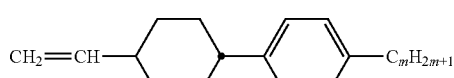
CP-V-m
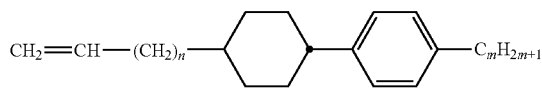
CP-Vn-m
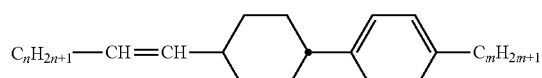
CP-nV-m
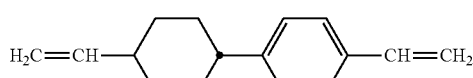
CP-V-V
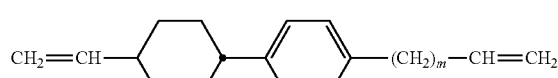
CP-V-mV
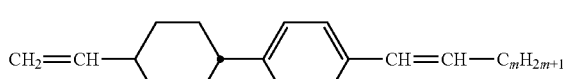
CP-V-Vm
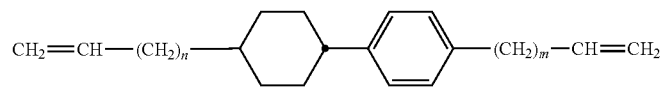
CP-Vn-mV
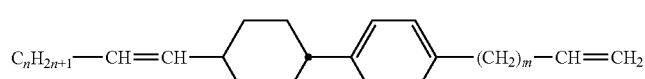
CP-nV-mV TABLE D-continued
Illustrative structures
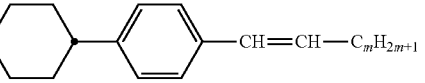
CP-nV-Vm
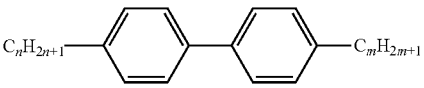
PP-n-m
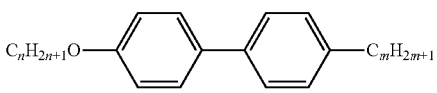
PP-nO-m
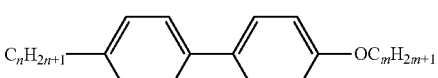
PP-n-Om
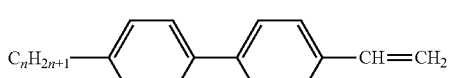
PP-n-V
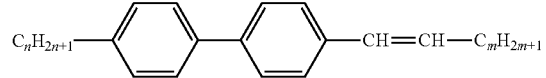
PP-n-Vm
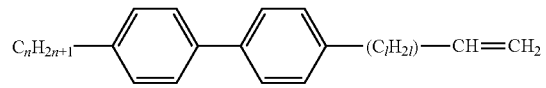
PP-n-lV
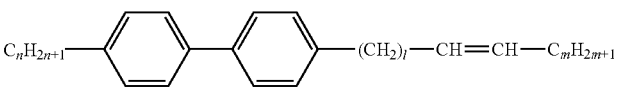
PP-n-lVm
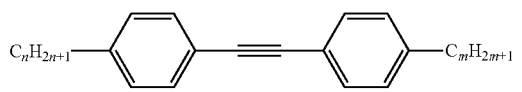
PTP-n-m
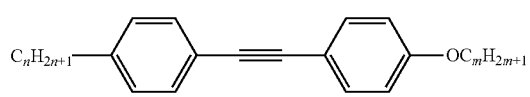
PTP-n-Om
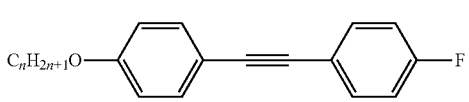
PTP-nO-F TABLE D-continued
Illustrative structures
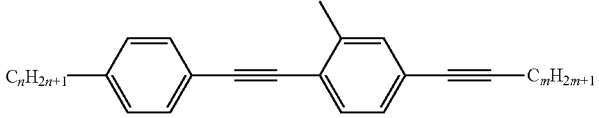
PTP(1)I-n-Am
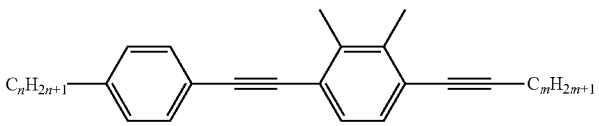
PTP(1;1)-n-Am
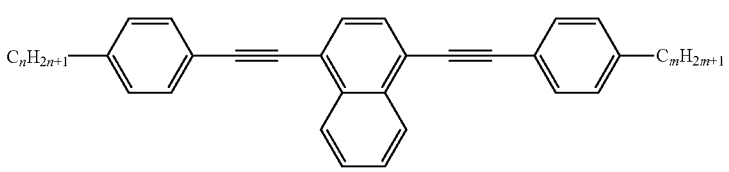
PTiNpTP-n-m
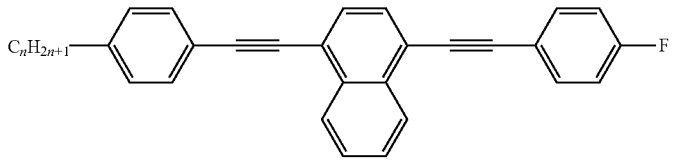
PTiNpTP-n-F
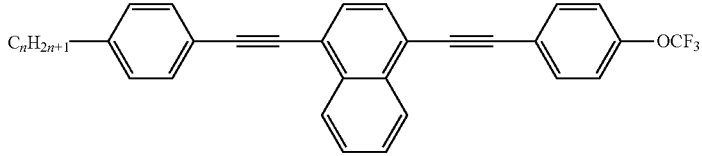
PTiNpTP-n-OT
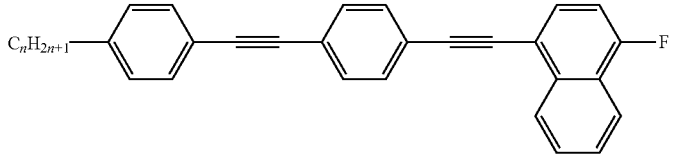
PTPTiNp-n-F
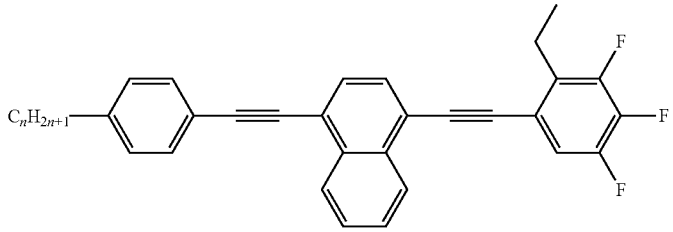
PTiNpTU(2)-n-F TABLE D-continued
Illustrative structures
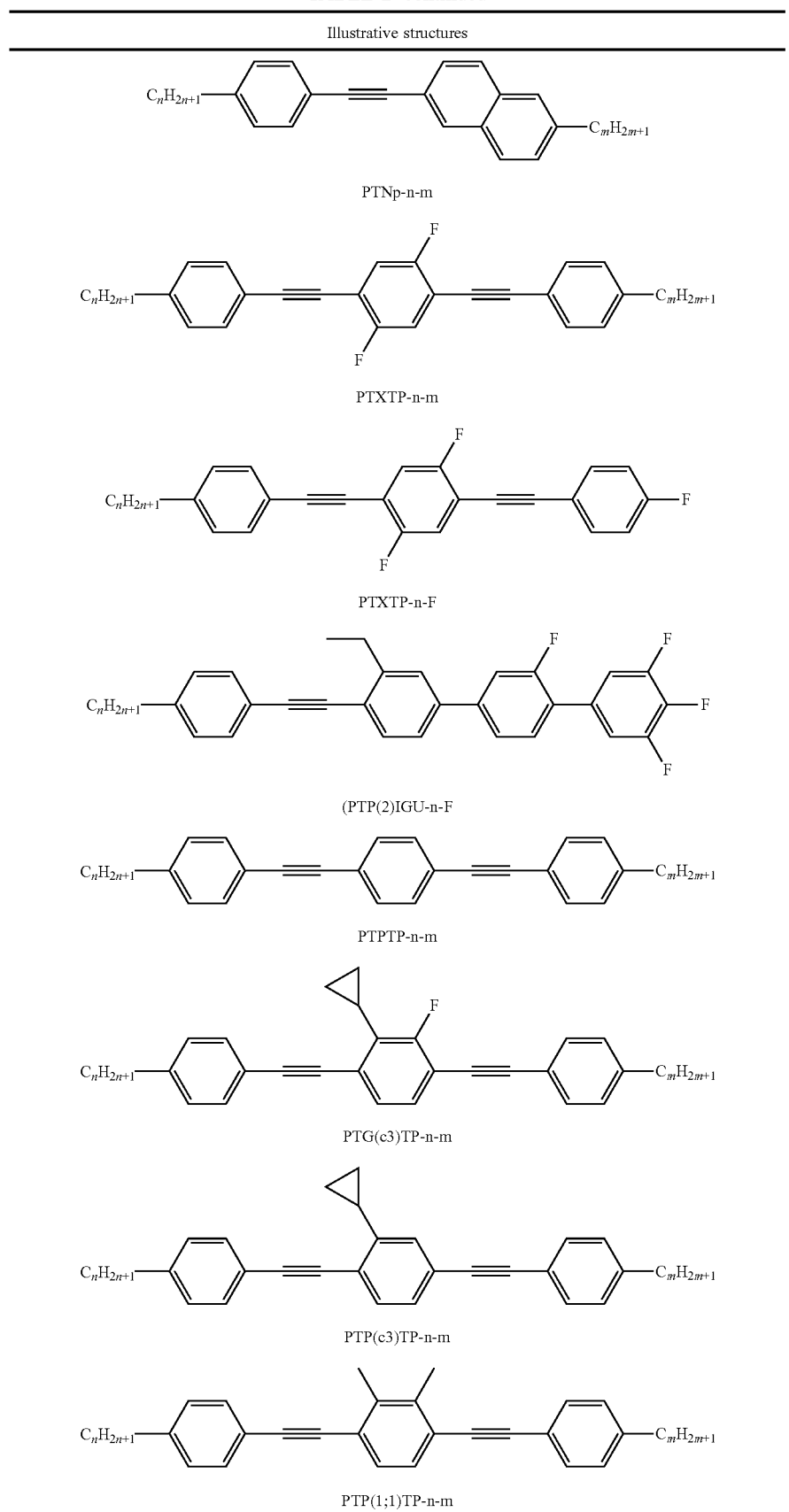

TABLE D-continued
Illustrative structures
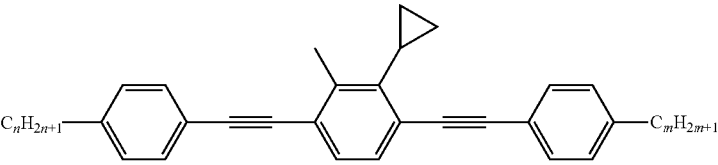
PTP(c3;1)TP-n-m
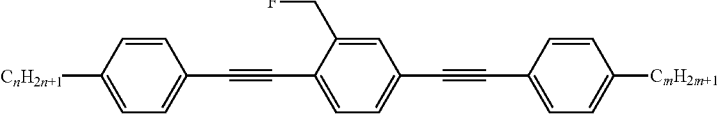
PTP(1M)TP-n-m
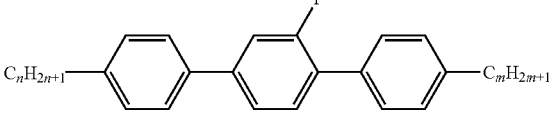
PGP-n-m
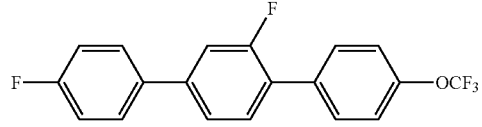 [SMILES: Fc1ccc(-c2ccc(-c3ccc(OC(F)(F)F)cc3)c(F)c2)cc1]
PGP-F-OT
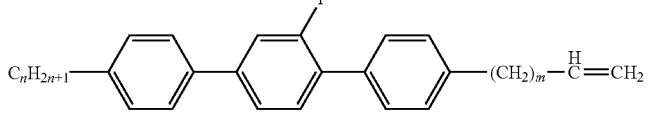
PGP-n-mV
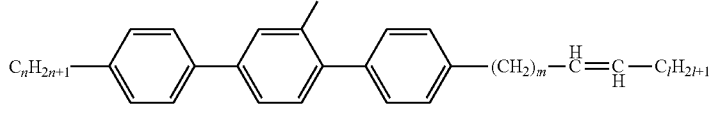
PGP-n-mVI
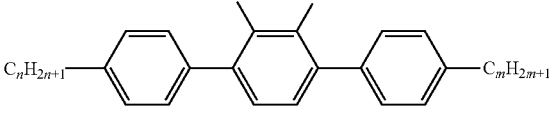
PYP-n-m
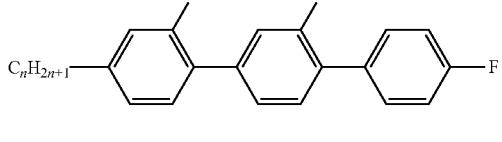
GGP-n-F TABLE D-continued Illustrative structures GGP-n-CL GGP-n-m PGIGI-n-F PGIGI-n-CL PGU-n-F PGU-n-CL PGU-n-OT PPTUI-n-m TABLE D-continued
Illustrative structures
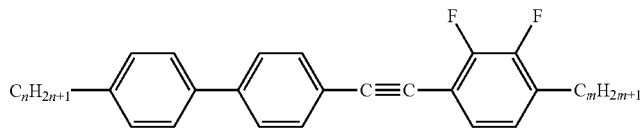
PPTY-n-m
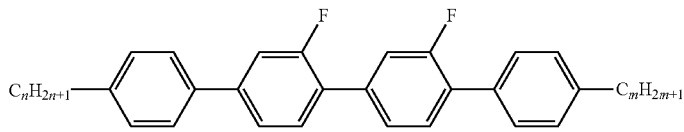
PGGP-n-m
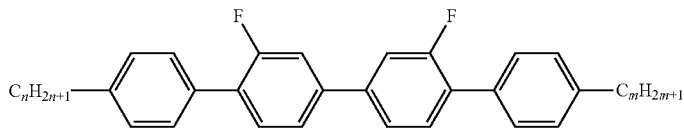
PGIGP-n-m
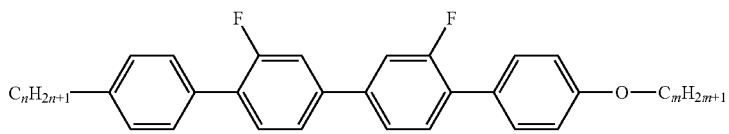
PGIGP-n-Om
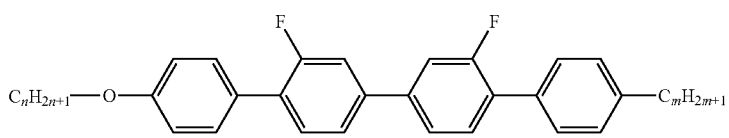
PGIGP-nO-m
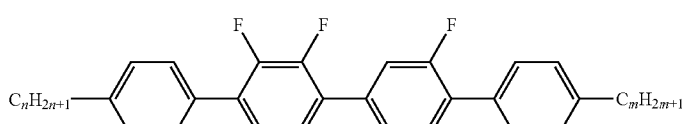
PYGP-n-m
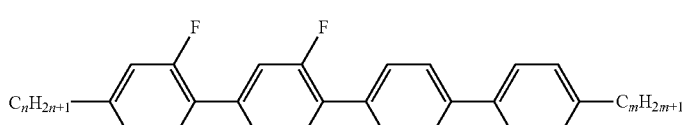
GGPP-n-m
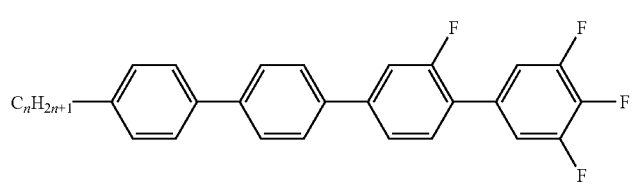
PPGU-n-F TABLE D-continued Illustrative structures CH₂=CH—C$_n$H$_{2n}$—[phenyl]—[phenyl]—[phenyl(F)]—[phenyl(F,F,F)]

PPGU-Vn-F

C$_n$H$_{2n+1}$—[cyclohexyl]—[phenyl]—C≡C—[phenyl]—C$_m$H$_{2m+1}$

CPTP-n-m

C$_n$H$_{2n+1}$—[cyclohexyl]—[phenyl]—[phenyl]—[cyclohexyl]—C$_m$H$_{2m+1}$

CPPC-n-m

C$_n$H$_{2n+1}$—[cyclohexyl]—[phenyl(F)]—[phenyl]—[cyclohexyl]—C$_m$H$_{2m+1}$

CGPC-n-m

C$_n$H$_{2n+1}$—[cyclohexyl]—[cyclohexyl]—CO—O—[phenyl]—[cyclohexyl]—C$_m$H$_{2m+1}$ CCZPC-n-m C$_n$H$_{2n+1}$—[cyclohexyl]—[phenyl]—[phenyl(F)]—[phenyl]—C$_m$H$_{2m+1}$ CPGP-n-m C$_n$H$_{2n+1}$—[cyclohexyl]—[phenyl]—[phenyl(F)]—[phenyl]—(CH$_2$)$_m$—CH=CH$_2$ CPGP-n-mV C$_n$H$_{2n+1}$—[cyclohexyl]—[phenyl]—[phenyl(F)]—[phenyl]—(CH$_2$)$_m$—CH=CH—C$_l$H$_{2l+1}$ CPGP-n-mVI C$_n$H$_{2n+1}$—[cyclohexyl]—[cyclohexyl]—[phenyl]—C$_m$H$_{2m+1}$ CCP-n-m TABLE D-continued
Illustrative structures
CCP-nO-m
CCP-n-Om
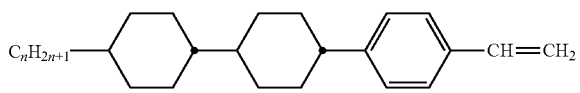
CCP-n-V
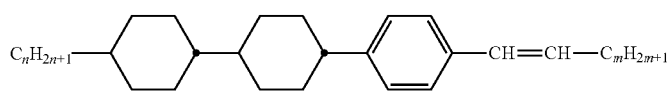
CCP-n-Vm
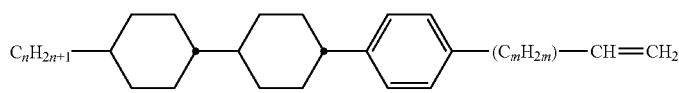
CCP-n-mV
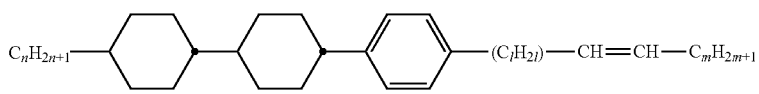
CCP-n-lVm
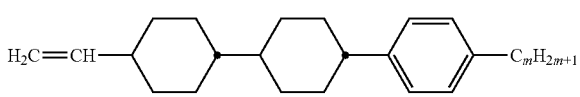
CCP-V-m
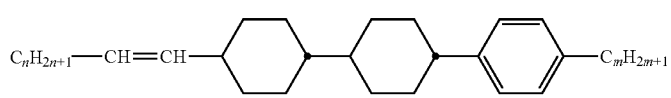
CCP-nV-m
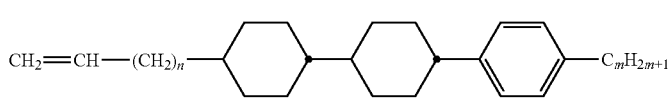
CCP-Vn-m
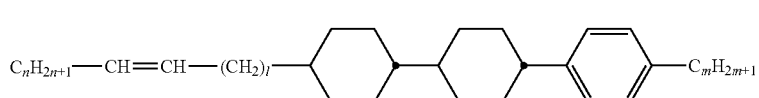
CCP-nVl-m
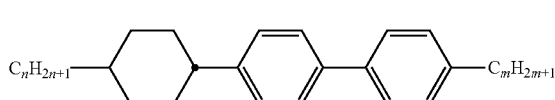
CPP-n-m TABLE D-continued
Illustrative structures
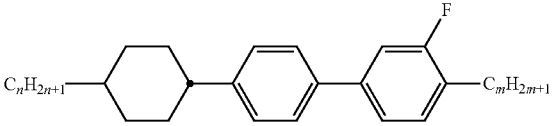
CPG-n-m
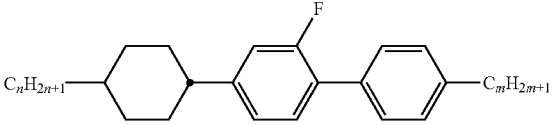
CGP-n-m
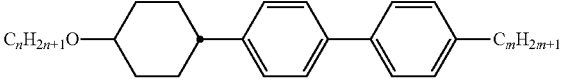
CPP-nO-m
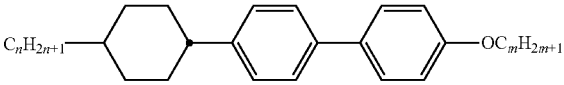
CPP-n-Om
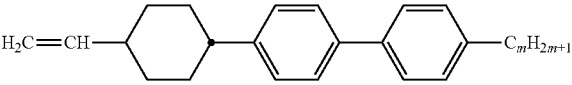
CPP-V-m
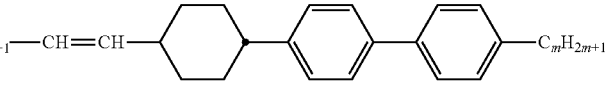
CPP-nV-m
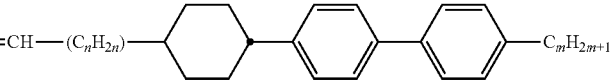
CPP-Vn-m
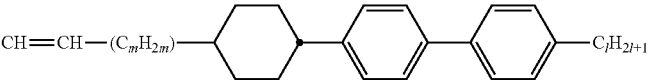
CPP-nVm-l
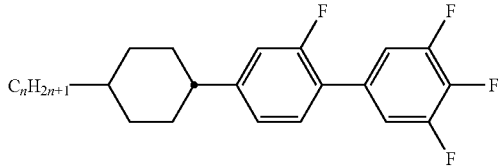
CGU-n-F TABLE D-continued
Illustrative structures
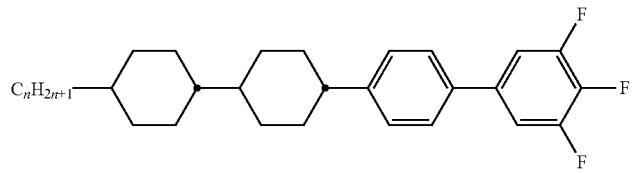
CCPU-n-F
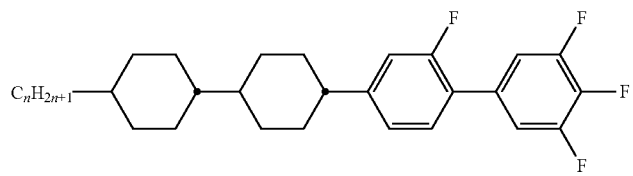
CCGU-n-F
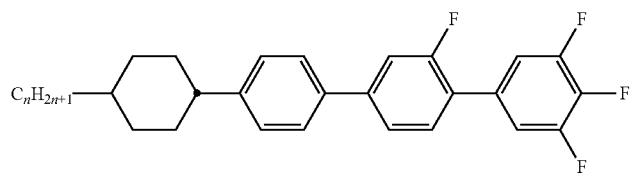
CPGU-n-F
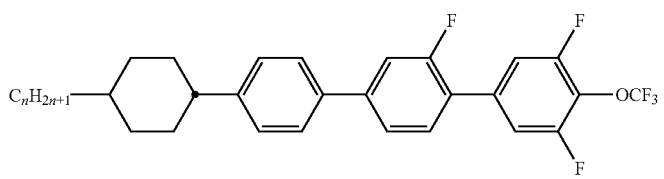
CPGU-n-OT
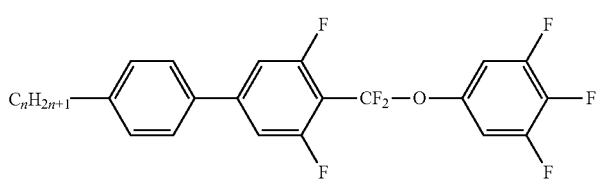
PUQU-n-F
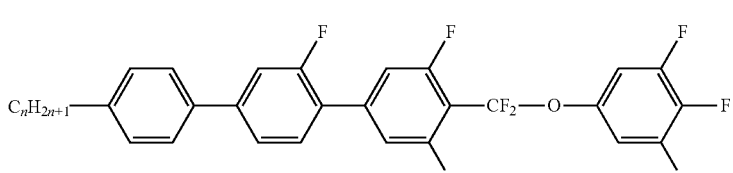
PGUQU-n-F
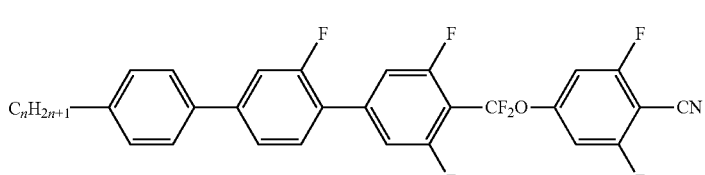
PGUQU-n-N TABLE D-continued
Illustrative structures
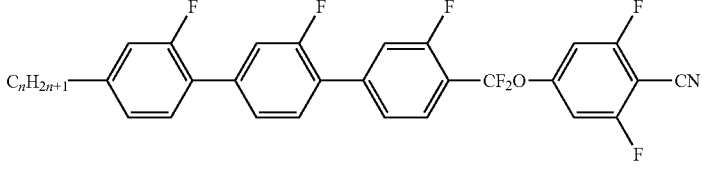
GGGQU-n-N
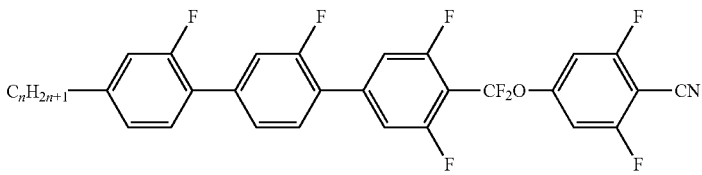
GGUQU-n-N
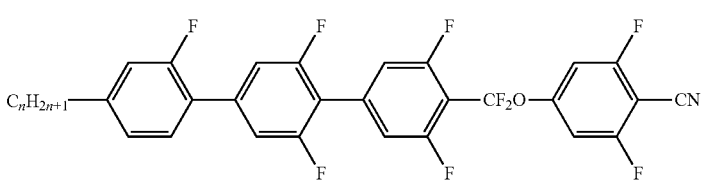
GUUQU-n-N
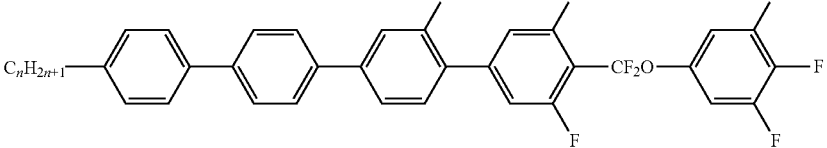
PPGUQU-n-N
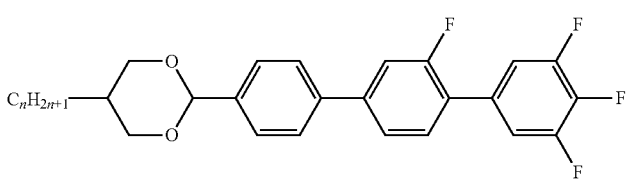
DPGU-n-F
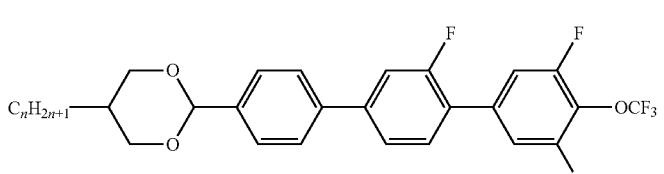
DPGU-n-OT
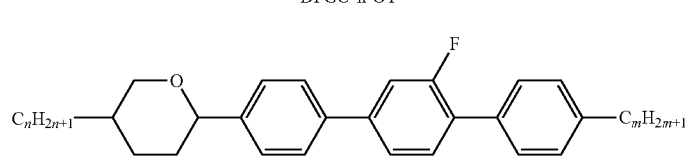
APGP-n-m TABLE D-continued
Illustrative structures
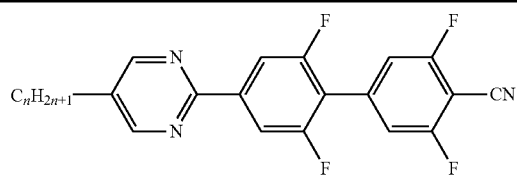
MUU-n-N
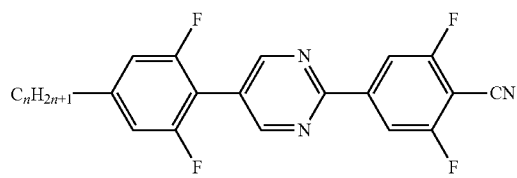
UMU-n-N
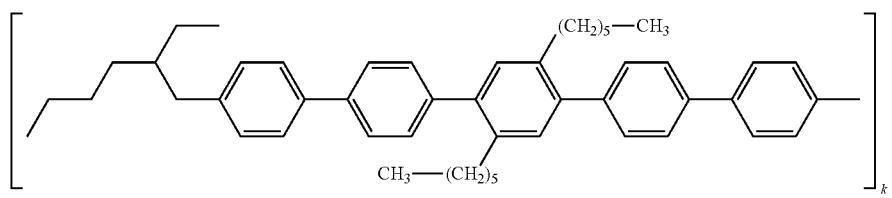
10*P-EH (k = 2)
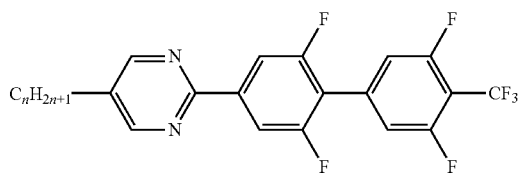
MUU-n-T
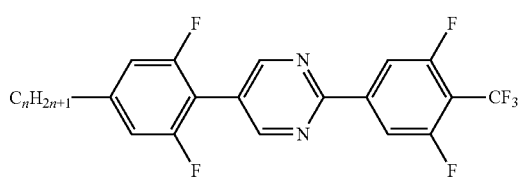
UMU-n-T
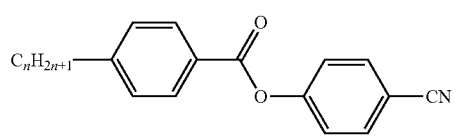
PZP-n-N
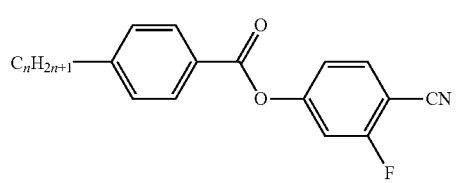
PZG-n-N

TABLE D-continued

Illustrative structures

![PVG-n-S structure: C_nH_{2n+1}-phenyl-CH=CH-phenyl(F)-NCS]

PVG-n-S n, m and l each, independently of one another, are an integer from 1 to 7, l preferably is 2 or 4, particularly preferably 2.

The following table, Table E, shows illustrative compounds which can be used as stabiliser in the mesogenic media in accordance with the present invention. The total concentration of these and similar compounds in the media is preferably 5% or less.

TABLE E

[Structure: bis-phenol with CH2 bridge, methyl and tert-butyl substituents, two OH groups]

[Structure: bis-phenol with CH(iPr) bridge, methyl and tert-butyl substituents, two OH groups]

[Structure: C_nH_{2n+1}-phenyl with two tert-butyl and OH]

n is an integer from 1 to 7

[Structure: C_nH_{2n+1}-cyclohexyl-phenyl(di-tert-butyl)-OH]

TABLE E-continued

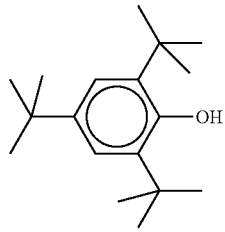

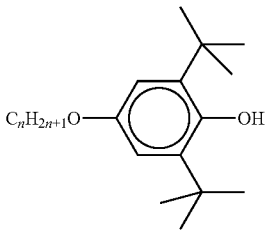

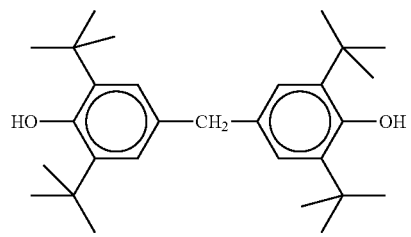

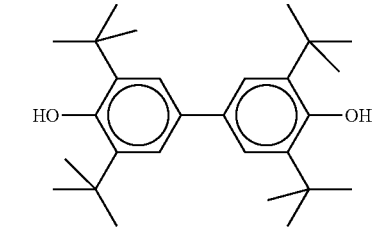

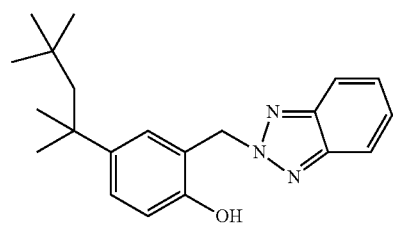 [SMILES: CC(C)(C)CC(C)(C)c1ccc(O)c(Cn2nc3ccccc3n2)c1]

TABLE E-continued
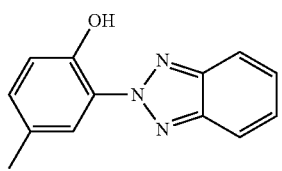 [SMILES: Cc1ccc(O)c(-n2nc3ccccc3n2)c1]
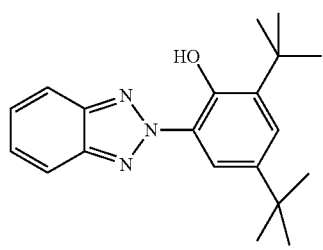 [SMILES: CC(C)(C)c1cc(-n2nc3ccccc3n2)c(O)c(C(C)(C)C)c1]
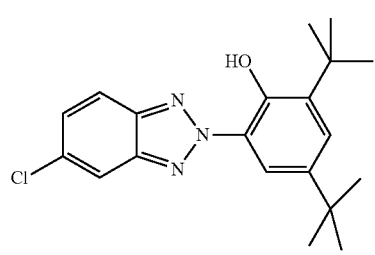 [SMILES: CC(C)(C)c1cc(-n2nc3ccc(Cl)cc3n2)c(O)c(C(C)(C)C)c1]
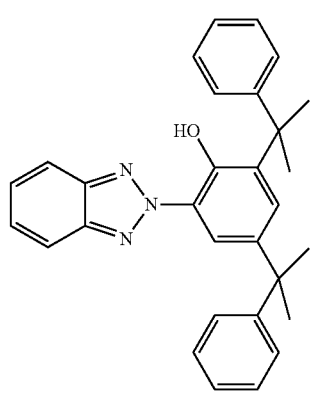 [SMILES: CC(C)(c1ccccc1)c1cc(-n2nc3ccccc3n2)c(O)c(C(C)(C)c2ccccc2)c1]
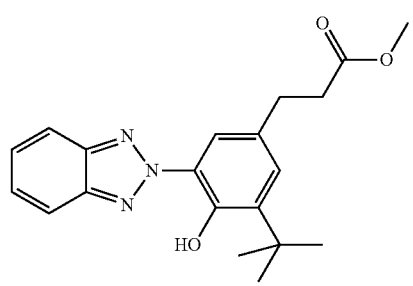 [SMILES: COC(=O)CCc1cc(-n2nc3ccccc3n2)c(O)c(C(C)(C)C)c1]
TABLE E-continued
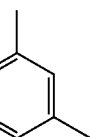
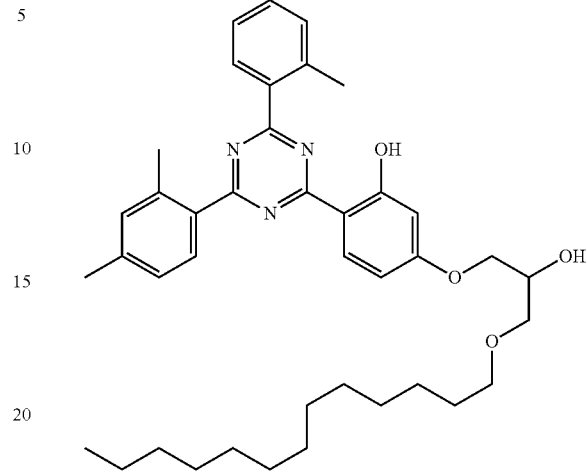
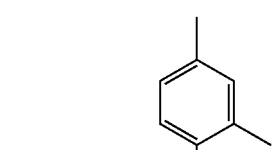
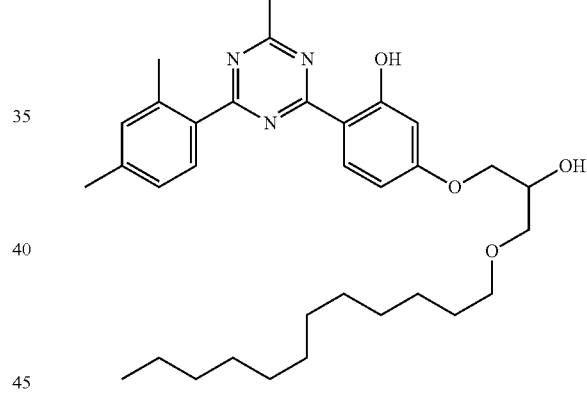
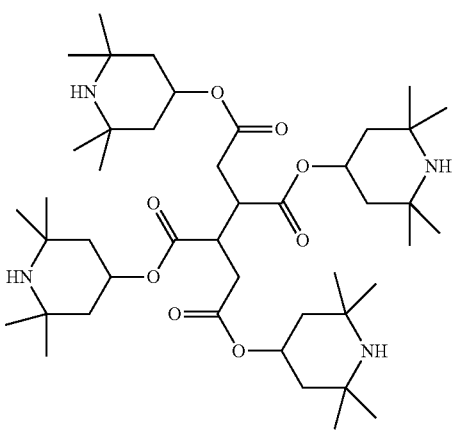

TABLE E-continued
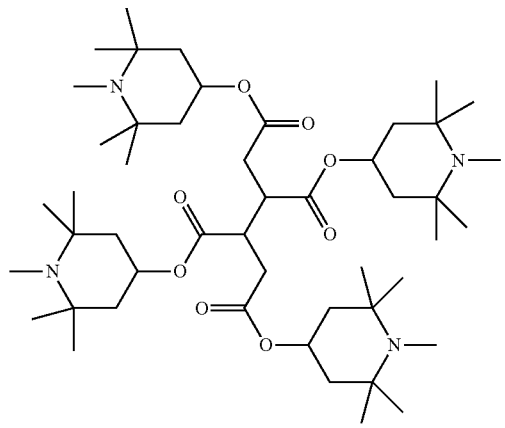
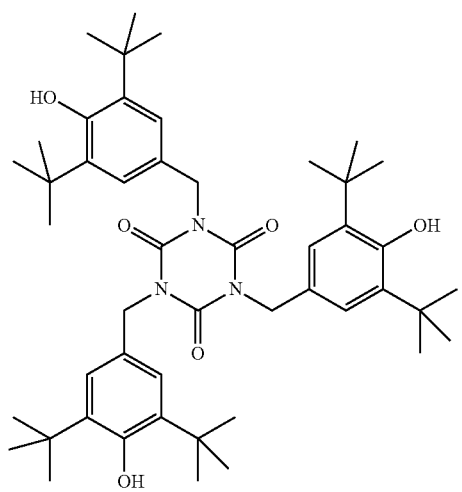 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
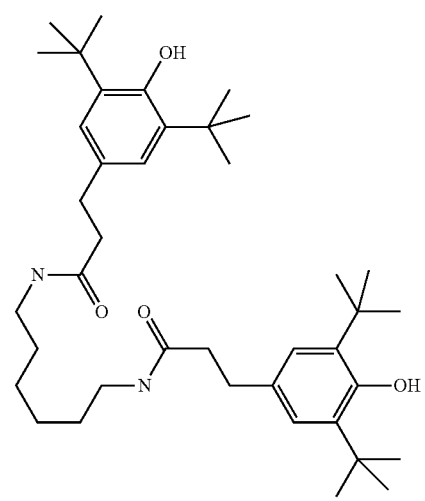 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
TABLE E-continued
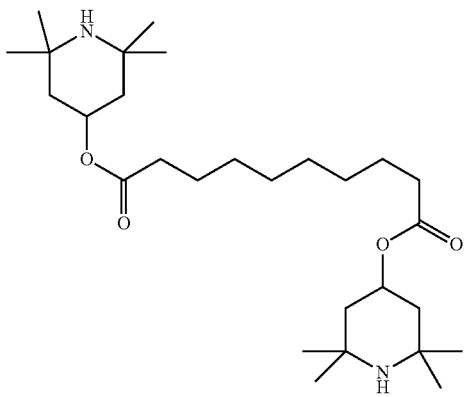
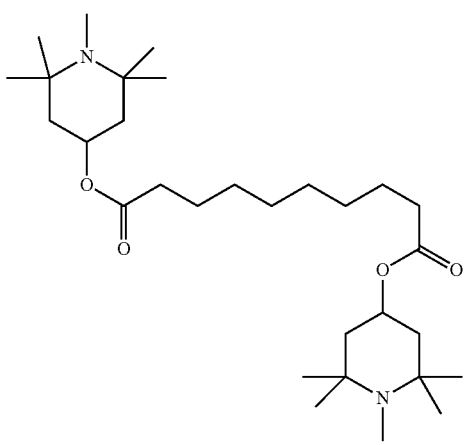
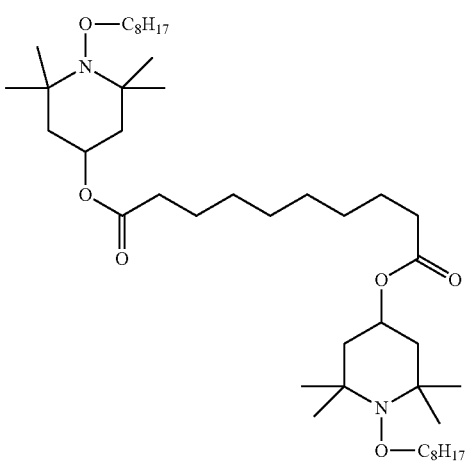
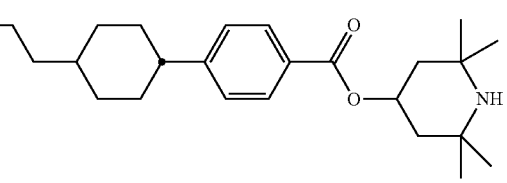

TABLE E-continued

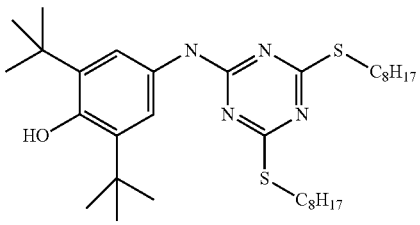

In a preferred embodiment of the present invention, the mesogenic media comprise one or more compounds selected from the group of the compounds from Table E.

The mesogenic media in accordance with the present application preferably comprise two or more, preferably four or more, compounds selected from the group consisting of the compounds from the above tables.

The liquid-crystal media in accordance with the present invention preferably comprise
seven or more, preferably eight or more, compounds, preferably compounds having three or more, preferably four or more, different formulae, selected from the group of the compounds from Table D.

EXAMPLES

The following examples illustrate the present invention without limiting it in any way. However, it becomes clear to the person skilled in the art from the physical properties what properties can be achieved and in what ranges they can be modified. In particular, the combination of the various properties which can preferably be achieved is thus well defined for the person skilled in the art.

SYNTHESIS EXAMPLES

Synthesis Example 1: 5-[(E)-1,2-difluoro-2-(4-pentylphenyl)vinyl]-1,3-difluoro-2-isothiocyanato-benzene

1.1 [(Z)-1,2-difluoro-2-(4-pentylphenyl)vinyl]-triethyl-silane

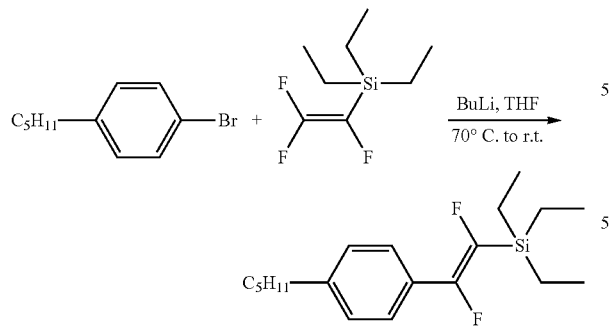

A solution of n-BuLi in hexane (19.1 mL, 15%, 30.4 mmol) are added dropwise to a stirred solution of 4-Bromo-n-pentylbenzene (6.7 g, 29.5 mmol) in THF (65 mL) at −70° C. The resulting mixture is stirred for 1.5 h before it is treated with a solution of triethylsilyl-trifluroethylene (6.4 g, 31.6 mmol) in THF (10 mL) at the same temperature. The reaction mixture is allowed to warm to room temperature and stirred overnight, before it is quenched with sat. NH$_4$Cl solution and diluted with methyl tert-butyl-ether. The aqueous phase is separated and extracted with methyl tert-butyl ether. The combined organic phase are washed with sat. NaCl solution, dried over Na$_2$SO$_4$, filtered and concentrated under vacuo. The residue is filtered through a short pad of silica (heptane) to give [(Z)-1,2-difluoro-2-(4-pentylphenyl)vinyl]-triethyl-silane as a colourless oil.

1.2 1-[(E)-1,2-difluorovinyl]-4-pentyl-benzene

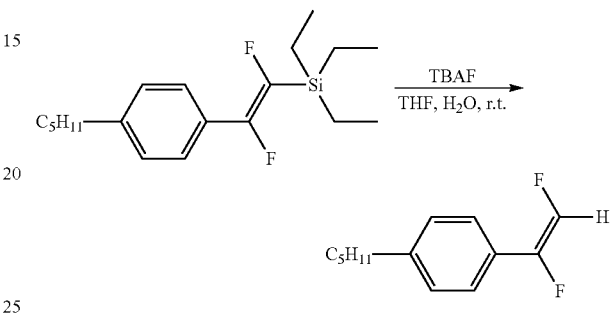

A solution of tetrabutylammonium fluoride in THF (17.1 mL, 1M, 17.1 mmol) are added dropwise to a stirred solution of [(Z)-1,2-difluoro-2-(4-pentylphenyl)vinyl]-triethyl-silane (6.2 g, 15.5 mmol) in THF (40 mL) and water (0.28 mL, 15.5 mmol) at room temperature. The resulting mixture is stirred for 3 h at the same temperature before it is treated with water and methyl tert-butyl ether. The aqueous phase is separated and extracted with methyl tert-butyl ether. The combined organic phase are washed with sat. NaCl solution, dried over Na$_2$SO$_4$, filtered and concentrated under vacuo. The residue is filtered through a pad of silica (pentane) to give 1-[(E)-1,2-difluorovinyl]-4-pentyl-benzene as a colourless oil.

1.3 1-[(E)-1,2-difluoro-2-iodovinyl]-4-pentyl-benzene

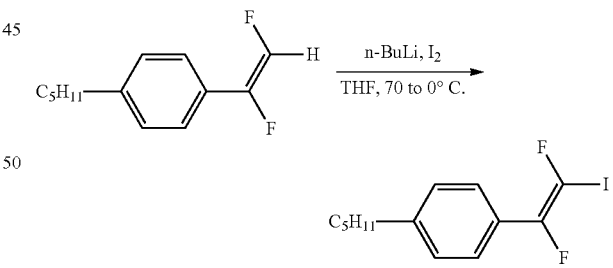

A solution of n-BuLi in hexane (13.8 mL, 15%, 22.1 mmol) is added dropwise to a stirred solution of 1-[(E)-1,2-difluorovinyl]-4-pentyl-benzene (6.4 g, 66%, 20.1 mmol) in THF (12 mL) at −70° C. The resulting mixture is stirred 1 h at the same temperature, before it is treated with a solution of iodine (6.1 g, 24.1 mmol) in 15 mL THF. The reaction mixture is allowed to warm to 0° C., treated with water, methyl tert-butyl ether and sodium thiosulfate (2.2 g, 8.8 mmol). The aqueous phase is separated and extracted with methyl tert-butyl ether. The combined organic phases are washed with sat. NaCl solution, dried over Na$_2$SO$_4$, filtered and concentrated under vacuo. The residue is filtered through a pad of silica (pentane) to give 1-[(E)-1,2-difluoro-2-iodovinyl]-4-pentyl-benzene as a red oil.

1.4 4-[(E)-1,2-difluoro-2-(4-pentylphenyl)vinyl]-2,6-difluoro-aniline

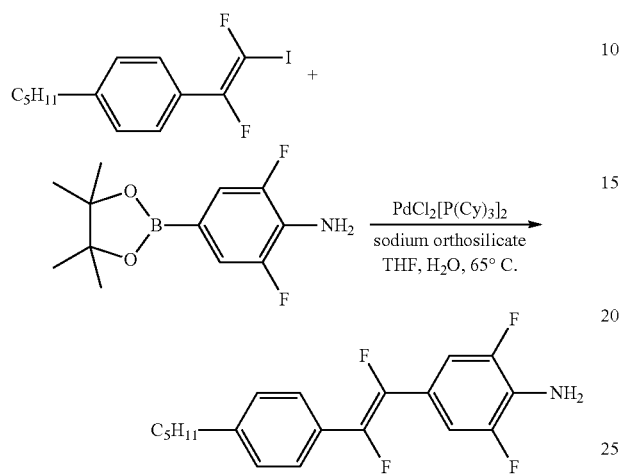

To a premixed suspension of sodium orthosilicate (1.8 g, 9.83 mmol) in water (4.8 mL) and PdCl$_2$[P(Cy)$_3$]$_2$ (0.23 g, 0.31 mmol) THF (16 mL) is added, followed by 2,6-difluoro-4-(4,4,5,5-tetramethyl-1,3,2-dioxaborolan-2-yl) aniline (3.8 g, 14.9 mmol) and 1-[(E)-1,2-difluoro-2-iodovinyl]-4-pentyl-benzene (7.2 g, 14.9 mmol, GC: 69.6%) at room temperature. The resulting mixture is stirred overnight at 65° C., before the organic phase is separated and extracted with water. The aqueous phases are combined and extracted with methyl tert-butylether. The combined organic phase are washed with water, dried over Na$_2$SO$_4$, filtered and concentrated in vacuo. The residue is filtered through a pad of silica (heptane/toluene 1:1) to give 4-[(E)-1,2-difluoro-2-(4-pentylphenyl)vinyl]-2,6-difluoro-aniline as an orange solid.

1.5 5-[(E)-1,2-difluoro-2-(4-pentylphenyl)vinyl]-1,3-difluoro-2-isothiocyanato-benzene

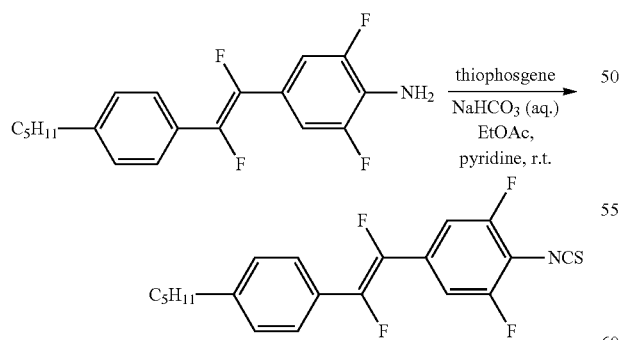

Thiophosgene (1.7 mL, 21.5 mmol) is added dropwise to a stirred suspension of 4-[(E)-1,2-difluoro-2-(4-pentylphenyl)vinyl]-2,6-difluoro-aniline (3.7g, 10.7 mmol), pyridine (0.09 mL, 1.08 mmol) and aqueous NaHCO$_3$ (51.6g, 8.8%, 53.8 mmol) in ethyl acetate (25 mL) at 0° C. The mixture is allowed to warm to room temperature and stirred for 1 h. Additional 20 mL of sat. NaHCO$_3$ are added followed by 1 h stirring at ambient temperature before the organic phase is separated. The aqueous phase is extracted with ethyl acetate. The combined organic phases are concentrated in vacuo, and the residue is filtered through a pad of silica (heptane/toluene 1:1), followed by crystallization from heptane (2 times) to give 5-[(E)-1,2-difluoro-2-(4-pentylphenyl)vinyl]-1,3-difluoro-2-isothiocyanato-benzene as colourless needles.

$^1$H NMR: 0.91-0.94 (m, 3H), 1.31-1.43 (m, 4H), 1.64-1.71 (m, 2H), 2.66-2.70 (m, 2H), 7.31 (d, J=8.2 Hz, 2H), 7.37-7.42 (m, 2H), 7.71-7.65 (m, 2H); $^{19}$F NMR: −154.4 (dt, J=119.4, 3.7 Hz, 1F),−145.4 (d, J=119.1 Hz, 1F),−116.8 (dt, J=9.2, 2.8 Hz, 2F); EI-MS: 379.1.

Phase sequence: K 64 SmA 102 N 113.5 I

In Analogy to Synthesis Example 1, the Synthesis Examples 2, 3 and 4 are prepared:

Synthesis Example 2

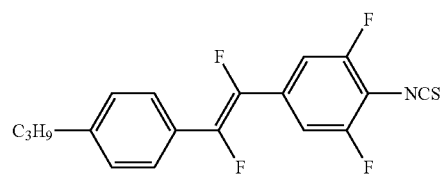

Phase sequence: K 75 SmA 95 N 112.3 I
Δε=16.2
Δn=0.3986
γ$_1$=64 mPa s

Synthesis Example 3

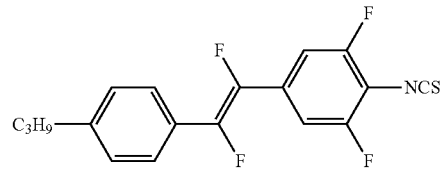

Phase sequence: K 47 N 57 I
Δε=19.7
Δn=0.3035
γ$_1$=77 mPa s

Synthesis Example 4

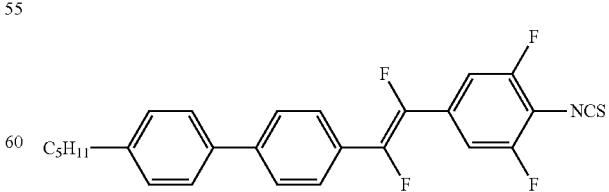

Phase sequence: K 75 SmX 234 N 274.4 I

In analogy to the above described synthesis and starting from 1-(4-n-pentylphenylethynyl)-2-ethyl-4-(Z-1,2-difluoro-2-iodoethylenyl)-benzene, prepared according to the procedure described on page 33 of WO 2012/069133 A1, Synthesis Example 4 is prepared.

Synthesis Example 5

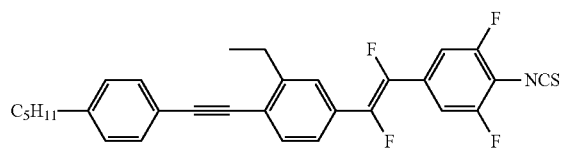

Phase sequence: K 120 N 196.9 I
$\Delta n = 0{,}5312$
$\gamma_1 = 1983$ mPa s

Use Examples

Comparative Example C-1

A liquid-crystalline substance having the abbreviation PTP(2)TP-6-3 is prepared by the method of Hsu, C. S., Shyu, K. F., Chuang, Y. Y. and Wu, S.-T., Liq. Cryst., 27 (2), (2000), pp. 283-287, and investigated with respect to its physical properties, in particular in the microwave region. The compound has a nematic phase and a clearing point (T(N,I)) of 119° C. and a melting point of 14° C. Further physical properties at 20° C. are: $n_e(589.3 \text{ nm}) = 1.8563$; $\Delta n(589.3 \text{ nm}) = 0.3250$; $\varepsilon_\parallel(1 \text{ kHz}) = 3.4$; $\Delta\varepsilon(1 \text{ kHz}) = 0.8$ and $\gamma_1 = 1708$ mPa·s. The compound is suitable for applications in the microwave region and/or millimetre wave region, in particular for phase shifters but lacks low temperature stability due to its high melting point of 14° C.

TABLE 1a

Properties of the compound PTP(2)TP-6-3 at 30 GHz

| T/° C. | $\varepsilon_{r,\parallel}$ | $\varepsilon_{r,\perp}$ | $\tau$ | $\tan\delta_{\varepsilon,r,\parallel}$ | $\tan\delta_{\varepsilon,r,\perp}$ | $\eta$ |
|---|---|---|---|---|---|---|
| 20 | 3.22 | 2.44 | 0.242 | 0.0029 | 0.0064 | 37.9 |

TABLE 1b

Properties of the compound PTP(2)TP-6-3 at 19 GHz

| T/° C. | $\varepsilon_{r,\parallel}$ | $\varepsilon_{r,\perp}$ | $\tau$ | $\tan\delta_{\varepsilon,r,\parallel}$ | $\tan\delta_{\varepsilon,r,\perp}$ | $\eta$ |
|---|---|---|---|---|---|---|
| 20 | 3.35 | 2.42 | 0.278 | 0.0029 | 0.0061 | 45.2 |

In addition, the properties of the compound n-1-pentyl-4'-cyanobiphenyl (also called PP-5-N or CB15) (Comparative Example C-2) and the liquid-crystal mixture ZLI-4792 (product from Merck KGaA, Darmstadt, Germany, Comparative Example C-3) were investigated at 19 GHz.

Mixture Examples 1 to 18 and 20 to 28 are prepared according to the tables given below. All Mixture Examples have broad nematic phase ranges with the clearing temperatures (T(N,I)) given in the respective table and good low temperature stability suitable for applications in microwave devices.

Use Example 1

| PVfP-2-4 | 100% | $T_{(N,I)}$ [° C.]: | 50.5 |
|---|---|---|---|
| | | $\varepsilon_\parallel$: | 2.9 |
| | | $\Delta\varepsilon$: | 0.5 |
| | | $\gamma_1$ [mPa·s]: | 41 |
| | | $K_1$ [pN]: | 7.0 |
| | | $K_3$ [pN]: | 9.3 |
| | | $V_0$ [V]: | 3.92 |

Mixture Example 2

| PVfP-2-2 | 67.0% | $T_{(N,I)}$ [° C.]: | 97.0 |
|---|---|---|---|
| PVfGP-2-4 | 33.0% | $\varepsilon_\parallel$: | 3.3 |
| | | $\Delta\varepsilon$: | 0.6 |
| | | $\gamma_1$ [mPa·s]: | 93 |
| | | $K_1$ [pN]: | 13.1 |
| | | $K_3$ [pN]: | 19.3 |
| | | $V_0$ [V]: | 5.10 |

Mixture Example 3

| PVfP-2-4 | 60.0% | $T_{(N,I)}$ [° C.]: | 86.0 |
|---|---|---|---|
| NpVfP-4-6 | 10.0% | $\varepsilon_\parallel$: | 3.1 |
| NpVfP-4-4 | 30.0% | $\Delta\varepsilon$: | 0.6 |
| | | $\gamma_1$ [mPa·s]: | 98 |
| | | $K_1$ [pN]: | 11.5 |
| | | $K_3$ [pN]: | 15.9 |
| | | $V_0$ [V]: | 4.53 |

Mixture Example 4

| PVfP-2-4 | 70.0% | $T_{(N,I)}$ [° C.]: | 66.0 |
|---|---|---|---|
| PTPI(2)VfU-6-F | 20.0% | $\varepsilon_\parallel$: | 6.8 |
| PTPI(2)VfU-5-F | 10.0% | $\Delta\varepsilon$: | 4.0 |
| | | $\gamma_1$ [mPa·s]: | 86 |
| | | $K_1$ [pN]: | 9.3 |
| | | $K_3$ [pN]: | 10.8 |
| | | $V_0$ [V]: | 1.62 |

Mixture Example 5

| PVfP-2-4 | 85.0% | $T_{(N,I)}$ [° C.]: | 52.0 |
|---|---|---|---|
| PVfUQU-3-F | 15.0% | $\varepsilon_\parallel$: | 6.6 |
| | | $\Delta\varepsilon$: | 3.7 |
| | | $\gamma_1$ [mPa·s]: | 40 |
| | | $K_1$ [pN]: | 7.2 |
| | | $K_3$ [pN]: | 8.2 |
| | | $V_0$ [V]: | 1.47 |

Mixture Example 6

| CC-3-V | 20.0% | $T_{(N,I)}$ [° C.]: | 126 |
|---|---|---|---|
| PVfP(2)TP-4-4 | 16.0% | $n_o$: | 1.5077 |
| PVfP(2)TP-3-6 | 20.0% | $\Delta n$: | 0.3091 |
| PVfP(2)TP-3-4 | 20.0% | $\varepsilon_\parallel$: | 5.8 |
| PTPI(2)VfG-6-OT | 12.0% | $\Delta\varepsilon$: | 3.0 |
| PTPI(2)VfG-5-OT | 12.0% | $\gamma_1$ [mPa·s]: | 567 |
| | | $K_1$ [pN]: | 13.3 |
| | | $K_3$ [pN]: | 24.4 |
| | | $V_0$ [V]: | 2.23 |

Mixture Example 7

| | | | |
|---|---|---|---|
| PTPI(2)VfG-6-OT | 20.0% | $T_{(N,D)}$ [° C.]: | 117 |
| PTPI(2)VfG-5-OT | 20.0% | $\varepsilon_{\parallel}$: | 7.6 |
| PTP(2)TP-6-3 | 60.0% | $\Delta\varepsilon$: | 4.5 |
| | | $\gamma_1$ [mPa · s]: | 1560 |
| | | $K_1$ [pN]: | 13.3 |
| | | $K_3$ [pN]: | 24.3 |
| | | $V_0$ [V]: | 1.82 |

Mixture Example 8

| | | | |
|---|---|---|---|
| PTG(c3)TP-4-4 | 40.0% | $T_{(N,D)}$ [° C.]: | 115 |
| PTNp-4-5 | 20.0% | $\varepsilon_{\parallel}$: | 3.6 |
| NpVfP-4-6 | 10.0% | $\Delta\varepsilon$: | 1.0 |
| NpVfP-4-4 | 20.0% | $\gamma_1$ [mPa · s]: | 855 |
| PTPI(1)-4-A1 | 10.0% | $K_1$ [pN]: | 12.1 |
| | | $K_3$ [pN]: | 29.2 |
| | | $V_0$ [V]: | 3.70 |

Mixture Example 9

| | |
|---|---|
| PTG(c3)TP-4-4 | 30.0% |
| PTPI(2)GU-4-F | 22.0% |
| PTPI(2)GG-5-OT | 8.0% |
| PTNp-4-5 | 10.0% |
| NpVfP-4-6 | 10.0% |
| NpVfP-4-4 | 20.0% |

Mixture Example 10

| | |
|---|---|
| PTiNpTP-4-4 | 10.0% |
| PTiNpTP-6-6 | 10.0% |
| PTiNpTP-3-6 | 10.0% |
| PTPI(2)GU-4-F | 22.0% |
| PTPI(2)GG-5-OT | 8.0% |
| PTNp-4-5 | 10.0% |
| NpVfP-4-6 | 10.0% |
| NpVfP-4-4 | 20.0% |

Mixture Example 11

| | | | |
|---|---|---|---|
| PTG(c4)TP-4-4 | 10.0% | $T_{(N,D)}$ [° C.]: | 105 |
| PTPI(c3)TP-4-4 | 5.0% | $\varepsilon_{\parallel}$: | 5.7 |
| PTP(c3)TP-3-6 | 15.0% | $\Delta\varepsilon$: | 2.8 |
| PTG(c5)TP-4-4 | 15.0% | $\gamma_1$ [mPa · s]: | 4809 |
| PTiNpTPI(2)-4-4 | 10.0% | $K_1$ [pN]: | 8.6 |
| PTiNpTPI(2)-4-A4 | 5.0% | $K_3$ [pN]: | 23.8 |
| PTiNpVfP-4-4 | 15.0% | $V_0$ [V]: | 1.85 |
| PTiNpTP-4-OT | 5.0% | | |
| PTPI(2)VfU-6-F | 15.0% | | |
| PTiNpTP-3-F | 5.0% | | |

Mixture Example 12

| | | | |
|---|---|---|---|
| PVfP-2-4 | 30.0% | $T_{(N,D)}$ [° C.]: | 92 |
| PPTUI-3-2 | 20.0% | $n_o$: | 1.5281 |
| PTP-2-O1 | 8.0% | $\Delta n$: | 0.2702 |
| PTP-3-O1 | 8.0% | $\varepsilon_{\parallel}$: | 8.3 |
| PGP-2-2V | 20.0% | $\Delta\varepsilon$: | 4.7 |
| PGUQU-3-F | 4.0% | $K_1$ [pN]: | 11.8 |
| PGUQU-5-F | 5.0% | $K_3$ [pN]: | 13.6 |
| PPGUQU-4-F | 5.0% | $V_0$ [V]: | 1.67 |

Mixture Example 13

| | | | |
|---|---|---|---|
| PTG(c3)TP-4-4 | 80.0% | $T_{(N,D)}$ [° C.]: | 135 |
| NpVfP-4-6 | 10.0% | $\varepsilon_{\parallel}$: | 3.8 |
| NpVfP-4-4 | 10.0% | $\Delta\varepsilon$: | 1.1 |
| | | $\gamma_1$ [mPa · s]: | 1487 |
| | | $K_1$ [pN]: | 11.7 |
| | | $K_3$ [pN]: | 38.2 |
| | | $V_0$ [V]: | 3.46 |

Mixture Example 14

| | | | |
|---|---|---|---|
| PTP(2)TP-6-3 | 80.0% | $T_{(N,D)}$ [° C.]: | 122 |
| PTiNpVfP-3-4 | 20.0% | $\varepsilon_{\parallel}$: | 3.6 |
| | | $\Delta\varepsilon$: | 1.0 |
| | | $K_1$ [pN]: | 11.5 |
| | | $K_3$ [pN]: | 43.4 |
| | | $V_0$ [V]: | 3.65 |

Mixture Example 15

| | | | |
|---|---|---|---|
| PPTUI-3-4 | 20.0% | $T_{(N,D)}$ [° C.]: | 129.5 |
| PPTUI-4-4 | 20.0% | $\varepsilon_{\parallel}$: | 7.3 |
| GGP-5-CL | 20.0% | $\Delta\varepsilon$: | 4.2 |
| PTP(2)TP-6-3 | 30.0% | $\gamma_1$ [mPa · s]: | 1102 |
| PTPI(2)VfU-F | 10.0% | | |

Mixture Example 16

| | | | |
|---|---|---|---|
| PTP-3-A1 | 8.0% | $T_{(N,D)}$ [° C.]: | 81 |
| PTP-5-A1 | 5.0% | $n_o$: | 1.5465 |
| PTPI(1)-4-A1 | 20.0% | $\varepsilon_{\parallel}$: | 5.8 |
| PTNp-4-5 | 20.0% | $\Delta\varepsilon$: | 3.0 |
| PTP(1.1)-4-A1 | 7.0% | $\gamma_1$ [mPa · s]: | 883 |
| PTP-3-A5 | 5.0% | $K_1$ [pN]: | 11.0 |
| PTiNpTP-3-F | 10.0% | $K_3$ [pN]: | 18.8 |
| PTPTiNp-4-F | 5.0% | $V_0$ [V]: | 2.03 |
| PTiNpVfU-4-F | 5.0% | | |
| PTiNpTU(2)-4-F | 5.0% | | |
| PTiNpTP-4-OT | 10.0% | | |

Mixture Example 17

| | | | |
|---|---|---|---|
| PTP-2-O1 | 8.0% | $T_{(N,D)}$ [° C.]: | 85 |
| PTP-3-O1 | 10.0% | $n_o$: | 1.5222 |
| PTP-5-O1 | 14.0% | $\Delta n$: | 0.3125 |
| PTP-4-O2 | 10.0% | $\varepsilon_{\parallel}$: | 7.4 |
| PTP-2O-F | 6.0% | $\Delta\varepsilon$: | 3.8 |
| PTP-4O-F | 8.0% | $\gamma_1$ [mPa · s]: | 352 |
| PTP-6O-F | 8.0% | $K_1$ [pN]: | 11.0 |
| PGUQU-3-F | 4.0% | $K_3$ [pN]: | 18.8 |
| PGUQU-5-F | 4.0% | $V_0$ [V]: | 2.03 |
| PTP(1)TP-4-4 | 6.0% | | |
| PTP(1F)TP-4-4 | 10.0% | | |
| PTPI(2)VfP-4-4 | 12.0% | | |

Mixture Example M-18

| | | | |
|---|---|---|---|
| PVfP-3-F | 20.0% | $T_{(N,D)}$ [° C.]: | 100 |
| PVfP-2-4 | 20.0% | $\varepsilon_{\parallel}$: | 8.4 |
| PTPI(2)VfP-4-4 | 30.0% | $\Delta\varepsilon$: | 5.5 |
| PTPI(2)VfU-6-F | 20.0% | $\gamma_1$ [mPa · s]: | 248 |
| PTPI(2)VfU-5-F | 10.0% | $K_1$ [pN]: | 12.8 |
| | | $K_3$ [pN]: | 18.7 |
| | | $V_0$ [V]: | 1.61 |

Mixture Example M-20

| PVfP-3-F | 20.0% | $T_{(N, I)}$ [° C.]: | 91 |
|---|---|---|---|
| PVfP-2-4 | 30.0% | | |
| P(2)TPVfP-6-3 | 20.0% | | |
| PTPI(2)VfU-6-F | 20.0% | | |
| PTPI(2)VfU-5-F | 10.0% | | |

Mixture Example M-21

| PVfU-3-F | 20.0% |
|---|---|
| PVfP-2-4 | 30.0% |
| P(2)TPVfP-6-3 | 20.0% |
| PTPI(2)VfU-6-F | 20.0% |
| PTPI(2)VfU-5-F | 10.0% |

Mixture Example M-22

| PVfP-3-F | 20.0% | $T_{(N, I)}$ [° C.]: | 127 |
|---|---|---|---|
| PVfP-2-4 | 20.0% | $\varepsilon_\parallel$: | 4.2 |
| P(2)TPVfP-6-3 | 30.0% | $\Delta\varepsilon$: | 1.7 |
| PVfP(2)TP-3-4 | 20.0% | $\gamma_1$ [mPa·s]: | 292 |
| PVfPP(2)TP-3-4 | 10.0% | $K_1$ [pN]: | 15.3 |
| | | $K_3$ [pN]: | 28.8 |
| | | $V_0$ [V]: | 3.19 |

Mixture Example M-23

| PVfP-3-F | 20.0% | $T_{(N, I)}$ [° C.]: | 114 |
|---|---|---|---|
| PVfP-2-4 | 30.0% | $\varepsilon_\parallel$: | 4.2 |
| P(2)TPVfP-6-3 | 20.0% | $\Delta\varepsilon$: | 1.6 |
| PVfP(2)TP-3-4 | 30.0% | $\gamma_1$ [mPa·s]: | 309 |
| | | $K_1$ [pN]: | 13.8 |
| | | $K_3$ [pN]: | 26.2 |
| | | $V_0$ [V]: | 3.10 |

Mixture Example M-24

| P(2)TPVfP-6-3 | 20.0% |
|---|---|
| PTPI(2)VfU-6-F | 10.0% |
| PTPI(2)VfU-5-F | 10.0% |
| PTPI(2)VfP-4-4 | 10.0% |
| PTP(2)VfP-3-6 | 20.0% |
| PVfP(Cl)TP-6-4 | 20.0% |
| PVfP(2)TP-3-4 | 10.0% |

Mixture Example M-25

| PVfP-3-F | 20.0% | $T_{(N, I)}$ [° C.]: | 115.5 |
|---|---|---|---|
| PVfP-2-4 | 30.0% | $\varepsilon_\parallel$: | 4.1 |
| P(2)TPVfP-6-3 | 20.0% | $\Delta\varepsilon$: | 1.6 |
| PTPI(2)VfP-4-4 | 20.0% | $\gamma_1$ [mPa·s]: | 226 |
| P(2)TNpVfP-4-4 | 10.0% | $K_1$ [pN]: | 13.3 |
| | | $K_3$ [pN]: | 22.6 |
| | | $V_0$ [V]: | 3.06 |

Mixture Example M-26

| PVfP-3-F | 20.0% | $T_{(N, I)}$ [° C.]: | 112.5 |
|---|---|---|---|
| PVfP-2-4 | 30.0% | $\varepsilon_\parallel$: | 4.2 |
| PTPI(2)VfP-4-4 | 20.0% | $\Delta\varepsilon$: | 1.7 |
| PTP(2)VfP-3-6 | 30.0% | $\gamma_1$ [mPa·s]: | 225 |
| | | $K_1$ [pN]: | 15.0 |
| | | $K_3$ [pN]: | 26.1 |
| | | $V_0$ [V]: | 3.17 |

Mixture Example M-27

| PVfP-3-F | 20.0% | $T_{(N, I)}$ [° C.]: | 110.5 |
|---|---|---|---|
| PVfP-2-4 | 30.0% | $\varepsilon_\parallel$: | 4.1 |
| PTPI(2)VfP-4-4 | 50.0% | $\Delta\varepsilon$: | 1.6 |
| | | $\gamma_1$ [mPa·s]: | 197 |
| | | $K_1$ [pN]: | 12.9 |
| | | $K_3$ [pN]: | 23.0 |
| | | $V_0$ [V]: | 3.00 |

Mixture Example M-28

| PVfP-3-F | 20.0% | $T_{(N, I)}$ [° C.]: | 124 |
|---|---|---|---|
| PVfP-2-4 | 30.0% | $\varepsilon_\parallel$: | 4.1 |
| P(2)TPVfP-6-3 | 20.0% | $\Delta\varepsilon$: | 1.6 |
| PTPI(2)VfP-4-4 | 20.0% | $\gamma_1$ [mPa·s]: | 297 |
| PVfPP(2)TP-3-4 | 10.0% | $K_1$ [pN]: | 14.7 |
| | | $K_3$ [pN]: | 25.6 |
| | | $V_0$ [V]: | 3.17 |

In the following table 1, the application-relevant properties of the comparative mixtures C-1 to C-3, measured at 20° C. and 19 GHz are summarised.

TABLE 1

| Example | $\varepsilon_{r,\parallel}$ | $\varepsilon_{r,\perp}$ | $\tau$ | $\tan\delta_{\varepsilon\, r,\, Max.}$ | $\eta$ |
|---|---|---|---|---|---|
| C-1 | 3.35 | 2.42 | 0.278 | 0.0061 | 45.2 |
| C-2 | 3.06 | 2.66 | 0.131 | 0.0273 | 4.8 |
| C-3 | 2.57 | 2.29 | 0.107 | 0.0126 | 8.5 |

In the following table 2, the application-relevant properties of mixtures according to the invention, measured at 20° C. and 19 GHz, are summarised.

TABLE 2

| Example | $\varepsilon_{r,\parallel}$ | $\varepsilon_{r,\perp}$ | $\tan\delta_{\varepsilon\, r,\parallel}$ | $\tan\delta_{\varepsilon\, r,\perp}$ | $\tau$ | $\eta$ |
|---|---|---|---|---|---|---|
| 1 | 2.86 | 2.33 | 0.0030 | 0.0054 | 0.185 | 34.6 |
| 2 | 3.00 | 2.32 | 0.0033 | 0.0087 | 0.226 | 25.9 |
| 3 | 2.98 | 2.34 | 0.0025 | 0.0050 | 0.216 | 43.0 |
| 4 | 2.95 | 2.32 | 0.0031 | 0.0060 | 0.215 | 35.8 |
| 5 | 2.87 | 2.32 | 0.0042 | 0.0089 | 0.189 | 21.2 |
| 6 | 3.03 | 2.31 | 0.0025 | 0.0068 | 0.237 | 34.7 |
| 7 | 3.31 | 2.38 | 0.0032 | 0.0078 | 0.280 | 35.9 |
| 8 | 3.29 | 2.43 | 0.0026 | 0.0062 | 0.261 | 42.3 |
| 13 | 3.34 | 2.43 | 0.0027 | 0.0068 | 0.273 | 40.0 |
| 16 | 3.37 | 2.48 | 0.0027 | 0.0057 | 0.264 | 46.7 |
| 18 | 3.11 | 2.31 | 0.0028 | 0.0065 | 0.256 | 39.4 |
| 19 | 3.01 | 2.33 | 0.0041 | 0.0079 | 0.225 | 28.5 |
| 20 | 3.09 | 2.35 | 0.0030 | 0.0066 | 0.240 | 36.4 |
| 21 | 3.05 | 2.33 | 0.0038 | 0.0086 | 0.236 | 27.4 |
| 22 | 3.15 | 2.34 | 0.0022 | 0.0062 | 0.258 | 41.6 |
| 23 | 3.14 | 2.35 | 0.0026 | 0.0065 | 0.253 | 38.9 |
| 24 | 3.29 | 2.35 | 0.0020 | 0.0059 | 0.287 | 48.6 |

In the following table 3, the application-relevant properties of mixtures according to the invention, measured at 20° C. and 30 GHz, are summarised.

TABLE 3

| Example | $\varepsilon_{r,\parallel}$ | $\varepsilon_{r,\perp}$ | $\tan\delta_{\varepsilon_{r,\parallel}}$ | $\tan\delta_{\varepsilon_{r,\perp}}$ | $\tau$ | $\eta$ |
|---|---|---|---|---|---|---|
| 14 | 3.15 | 2.40 | 0.0017 | 0.0058 | 0.238 | 41.1 |
| 15 | 3.07 | 2.36 | 0.0027 | 0.0110 | 0.232 | 21.2 |
| 17 | 3.81 | 3.13 | 0.0084 | 0.0204 | 0.179 | 8.8 |
| 29 | 3.80 | 3.12 | 0.0078 | 0.0178 | 0.178 | 9.9 |
| 30 | 3.13 | 2.40 | 0.0015 | 0.0052 | 0.233 | 44.9 |

As can be seen from the data in tables 2 and 3, the liquid crystalline media of Mixture Examples 1 to 18 and 20 to 28 are very well suitable for microwave applications, especially for phase shifters for 'phased array' antennae, because of their low dielectric loss (tan $\delta_{\varepsilon_r}$), high tunability ($\tau$) and high figures-of-merit ($\eta$).

The comparison with the mixtures from the state of the art (table 1) shows that by using one or more compounds of formula DFS in mixtures, higher figures-of-merit and/or higher tunability and/or lower dielectric loss can be achieved while the mixtures at the same time have very broad nematic phase ranges, high clearing temperatures and very good low temperature stabilities.

The invention claimed is:

1. A compound of formula PVfU-n-S

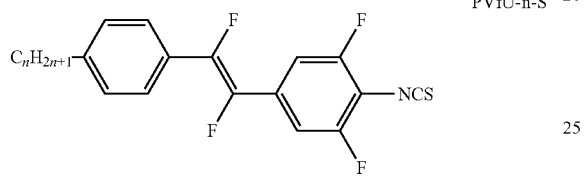

PVfU-n-S wherein n is 3.

2. A method of forming a liquid crystalline medium, which comprises incorporating the compound of formula PVfU-n-S of claim 1 into said medium.

3. A process for preparing the compound of formula PVfU n S of claim 1, which comprises converting an aniline analog of a compound of formula PVfU-n-S into a compound of formula PVfU n S, wherein said aniline analog is the following compound

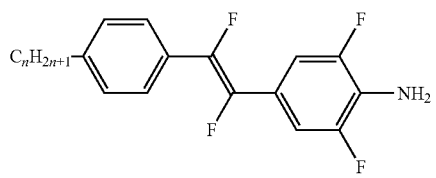

wherein n is 3.

4. A liquid crystal medium which comprises the compound of formula PVfU n S of claim 1, and further comprises one or more compounds of formula DFS-1 and optionally a compound of formula DFS-2-2

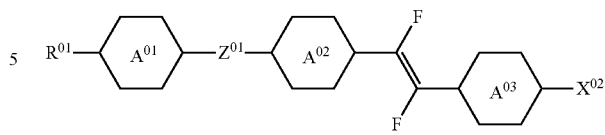

DFS-2-2 wherein:

$R^{01}$ and $R^{02}$ each independently denotes alkyl, which is straight chain or having 1 to 20 C-atoms or is branched having 3 to 20 C-atoms, and is unsubstituted, mono- or poly-substituted by F, Cl or CN, and in which one or more $CH_2$ groups are optionally replaced, in each case independently from one another, by —O—, —S—, —SiR$^a$R$^b$—, —CO—, —COO—, —OCO—, —OCO—O—, —S—CO—, —CO—S—, —CY$^{01}$=CY$^{02}$— or —C≡C— in such a way that O and/or S atoms are not linked directly to one another, $X^{02}$ denotes —NCS, $A^{03}$ denotes

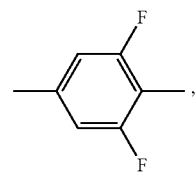

$Y^{01}$ and $Y^{02}$ identically or differently, denote H, F, Cl, or CN, alternatively one of $Y^{01}$ and $Y^{02}$ may also denote H, $R^a$ and $R^b$ identically or differently, denote alkyl having 1 to 6 C atoms, $A^{02}$ denotes

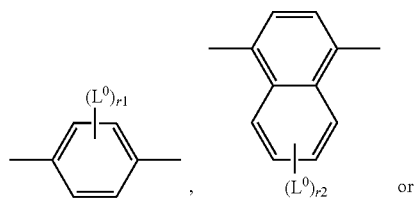

or

DFS-1

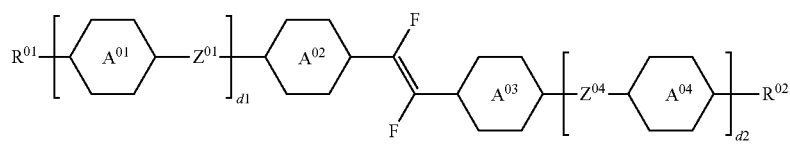

-continued

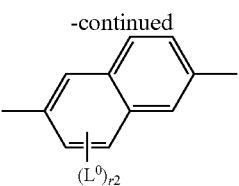

wherein, one or more of CH groups may be replaced by N, $A^{04}$ and $A^{01}$ are, each independently as defined as $A^{02}$, or alternatively denote

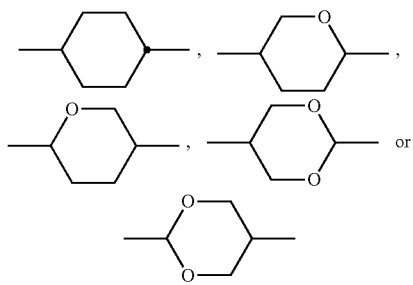 or $Z^{01}$ in formula DFS-2-2 denotes a single bond, $Z^{01}$ and $Z^{04}$ in formula DFS-1 on each occurrence, identically or differently, denote —C≡C—, —CF=CF—, —CF$_2$O—, —OCF$_2$—, —CH$_2$O—, —OCH$_2$—, —CH$_2$CH$_2$—, —CF$_2$CF$_2$—, —CH$_2$CF$_2$, —CF$_2$CH$_2$—, or a single bond, d1 and d2 are, independently from one another, 0, 1 or 2, $L^0$ denotes halogen, alkyl having 1 to 6 C atoms or alkenyl having 2 to 6 C atoms, or cycloalkyl or cycloalkenyl having 3 to 6 C atoms, where one or more H atoms can be substituted by fluorine, r1 is an integer from 0 to 4, and r2 is an integer from 0 to 6.

5. The liquid crystal medium of claim 4, wherein the total concentration of compounds of formulae PVfU-n-S and DFS-1 and optionally DFS-2-2 in the medium is 4% or more.

6. A high-frequency technology component, which contains the liquid-crystal medium according to claim 4.

7. A microwave antenna array, which comprises one or more high-frequency technology components according to claim 6.

8. A process for tuning a microwave antenna array comprising electrically addressing the high-frequency technology component according to claim 6.

* * * * *